United States Patent
McCann

(10) Patent No.: US 11,292,770 B2
(45) Date of Patent: Apr. 5, 2022

(54) PYRIDAZINONE HERBICIDES

(71) Applicant: FMC Corporation, Philadelphia, PA (US)

(72) Inventor: Stephen Frederick McCann, Newark, DE (US)

(73) Assignee: FMC Corporation, Philadelphia, PA (US)

( * ) Notice: Subject to any disclaimer, the term of this patent is extended or adjusted under 35 U.S.C. 154(b) by 386 days.

(21) Appl. No.: 16/499,248

(22) PCT Filed: Mar. 28, 2018

(86) PCT No.: PCT/US2018/024742
§ 371 (c)(1),
(2) Date: Sep. 28, 2019

(87) PCT Pub. No.: WO2018/183432
PCT Pub. Date: Oct. 4, 2018

(65) Prior Publication Data
US 2020/0109123 A1 Apr. 9, 2020

Related U.S. Application Data

(60) Provisional application No. 62/477,685, filed on Mar. 28, 2017.

(51) Int. Cl.
*C07D 237/14* (2006.01)
*A01N 43/58* (2006.01)
(Continued)

(52) U.S. Cl.
CPC .......... *C07D 237/14* (2013.01); *A01N 43/58* (2013.01); *A01P 13/00* (2021.08); *C07D 403/04* (2013.01); *C07D 405/04* (2013.01)

(58) Field of Classification Search
None
See application file for complete search history.

(56) References Cited

U.S. PATENT DOCUMENTS 8,470,738 B2   6/2013 Fusaka
8,884,010 B2   11/2014 Jachmann et al.
(Continued)

FOREIGN PATENT DOCUMENTS

GB   1130716    10/1968
WO   2005007632   1/2005
(Continued)

OTHER PUBLICATIONS

Babichev et al., "6-Amino-1-aryl-4-pyridazinones and their derivatives", Ukrainskii Khimicheskii Zhurnal (Russian Edition), vol. 49, Issue 11, pp. 1197-1202, 1983.
(Continued)

*Primary Examiner* — John Pak
(74) *Attorney, Agent, or Firm* — Reed A Coats; Xiaobin Ding; FMC Corporation

(57) ABSTRACT

Disclosed are compounds of Formula 1, including all stereoisomers, N-oxides, and salts thereof, agricultural compositions containing them and their use as herbicides (Formula 1), wherein $R^1$, $R^2$, L, G and W are as defined in the disclosure, and A is selected from (Formula A-1, A-2, A-3, A-4, A-5, A-6, A-7, A-8, A-9 and A-19) and $X^1$, $X^2$, $X^3$, $X^4$, $X^5$, $X^6$, $X^7$, $X^8$, $X^9$, $X^{10}$, Y and Y1 are as defined in the disclosure.

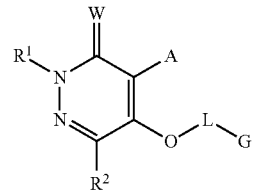

(1)

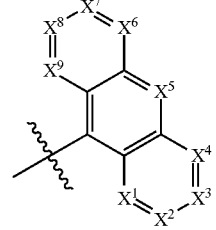

(A-1)

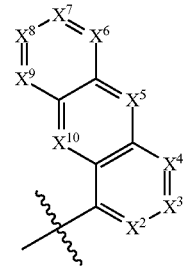

(A-2)

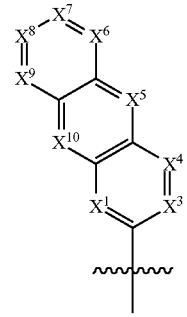

(A-3)

(Continued)

-continued

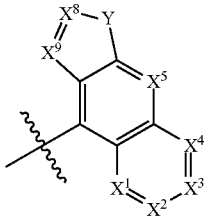
(A-4)

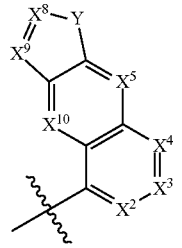

(A-5)

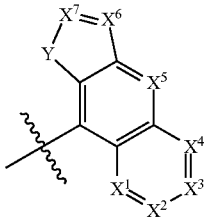

(A-6)

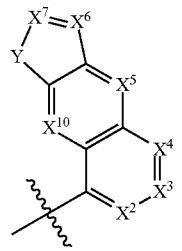

(A-7)

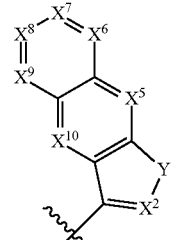

(A-8)

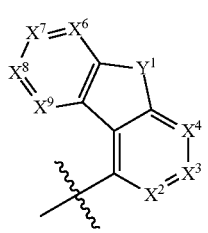

(A-9)

-continued

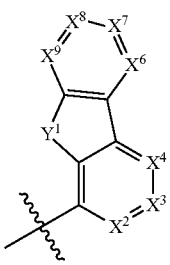
(A-10)

10 Claims, No Drawings

(51) Int. Cl.
    *C07D 405/04*     (2006.01)
    *C07D 403/04*     (2006.01)
    *A01P 13/00*     (2006.01)

(56) References Cited

U.S. PATENT DOCUMENTS

| | | |
|---|---|---|
| 9,029,295 B2 | 5/2015 | Kuragano et al. |
| 9,040,709 B2 | 5/2015 | Jachmann et al. |
| 9,049,864 B2 | 6/2015 | Burton et al. |
| 2010/0267561 A1 | 10/2010 | Stevenson et al. |
| 2018/0312467 A1 | 11/2018 | Selby et al. |
| 2018/0332851 A1 | 11/2018 | Stevenson et al. |
| 2020/0196604 A1* | 6/2020 | Marshall .............. C07D 237/16 |

FOREIGN PATENT DOCUMENTS

| | | |
|---|---|---|
| WO | 20070119434 | 10/2007 |
| WO | 2009/035150 | 3/2009 |
| WO | 20090035145 | 3/2009 |
| WO | 20090035151 | 3/2009 |
| WO | 20130050421 | 4/2013 |
| WO | 2013160126 | 10/2013 |
| WO | 2014031971 | 2/2014 |
| WO | 20150132608 | 9/2015 |
| WO | 20150168010 | 11/2015 |
| WO | 20170074992 | 5/2017 |
| WO | 2018183432 | 10/2018 |
| WO | 2019005484 | 1/2019 |
| WO | WO 2020/204112 | * 10/2020 |

OTHER PUBLICATIONS

International Search Report of corresponding PCT/US2018/024742 dated May 17, 2018.

* cited by examiner

PYRIDAZINONE HERBICIDES

FIELD OF THE INVENTION

This invention relates to certain pyridazinone herbicides, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1, including all stereoisomers, N-oxides, and salts thereof, agricultural compositions containing them and their use as herbicides

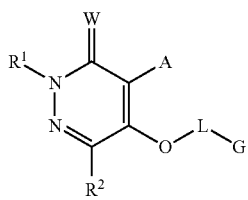

1 wherein
W is O or S;
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl; or a 5- or 6-membered saturated or partially saturated heterocyclic ring containing ring members selected from carbon and up to 1 O and 1 S;
$R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl; or phenyl optionally substituted by halogen, $C_1$-$C_4$ alkyl or $C_1$-$C_4$ haloalkyl;
L is a direct bond, $C_1$-$C_4$ alkanediyl or $C_2$-$C_4$ alkenediyl;
G is H, $C(=O)R^5$, $C(=S)R^5$, $CO_2R^6$, $C(=O)SR^6$, $S(O)_2R^5$, $CONR^7R^8$, $S(O)_2NR^7R^8$ or $P(=O)R^9R^{10}$; or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_3$-$C_6$ cycloalkyl or $C_4$-$C_7$ cycloalkylalkyl; or a 5- or 6-membered heterocyclic ring;
A is selected from

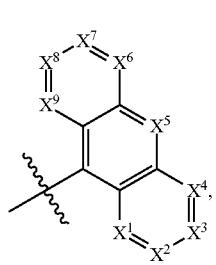

A-1

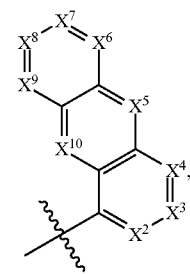

A-2

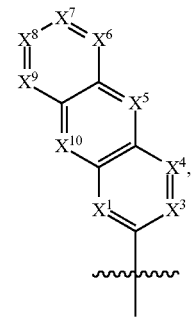

A-3

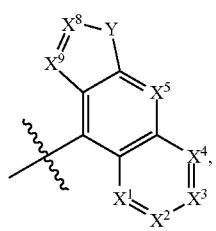

A-4

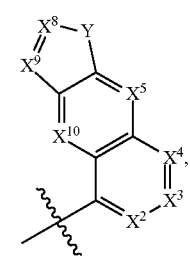

A-5

-continued

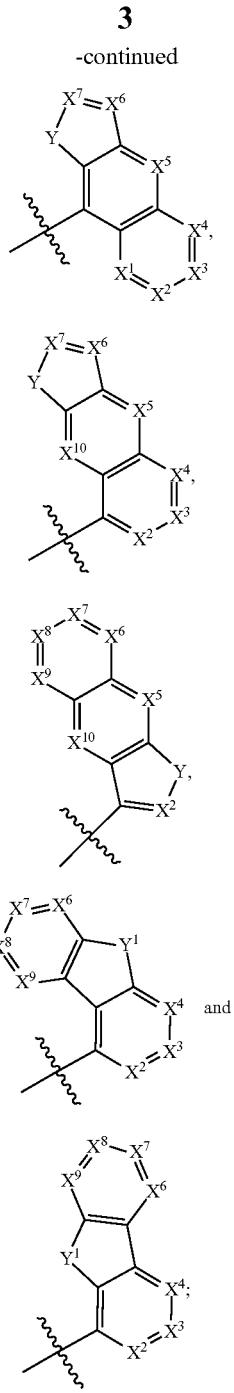

$X^1$, $X^2$, $X^3$, $X^4$, $X^5$, $X^6$, $X^7$, $X^8$, $X^9$ and $X^{10}$ are each independently N or $CR^3$; provided that no more than 4 of $X^1$, $X^2$, $X^3$, $X^4$, $X^5$, $X^6$, $X^7$, $X^8$, $X^9$ and $X^{10}$ are N;

Y is O, S or $NR^4$;

$Y^1$ is O, S, $NR^4$ or $CR^{3a}R^{3b}$;

each $R^3$ is independently H, halogen, cyano, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^{3a}$ is H, halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^{3b}$ is H, halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl; or $R^{3a}$ and $R^{3b}$ re taken together as =O; or $R^{3a}$ and $R^{3b}$ are taken together with the carbon atom to which they are bonded to form an optionally substituted 3- to 7-membered carbocyclic ring;

$R^4$ is H, $C_1$-$C_3$ alkyl or $C_1$-$C_3$ haloalkyl;

$R^5$ and $R^7$ are independently H, $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl or $C_4$-$C_7$ cycloalkylalkyl; or phenyl, benzyl, or a 5- to 6-membered heterocyclic ring, each phenyl, benzyl or heterocyclic ring optionally substituted by halogen, $C_1$-$C_4$ alkyl or $C_1$-$C_4$ haloalkyl;

$R^6$ is $C_1$-$C_7$ alkyl, $C_3$-$C_7$ alkenyl, $C_3$-$C_7$ alkynyl, $C_3$-$C_7$ cycloalkyl, $C_2$-$C_7$ haloalkyl, $C_3$-$C_7$ haloalkenyl, $C_2$-$C_7$ alkoxyalkyl or $C_4$-$C_7$ cycloalkylalkyl; or phenyl, benzyl or a 5- to 6-membered heterocyclic ring, each phenyl, benzyl or heterocyclic ring optionally substituted by halogen, $C_1$-$C_4$ alkyl or $C_1$-$C_4$ haloalkyl;

$R^8$ is H, $C_1$-$C_7$ alkyl, $C_2$-$C_7$ alkenyl, $C_2$-$C_7$ alkynyl, $C_3$-$C_7$ cycloalkyl, $C_4$-$C_7$ cycloalkylalkyl, $C_1$-$C_7$ haloalkyl or $C_2$-$C_7$ alkoxyalkyl;

$R^9$ is $C_1$-$C_7$ alkyl or $C_1$-$C_7$ alkoxy; and $R^{10}$ is $C_1$-$C_7$ alkyl or $C_1$-$C_7$ alkoxy.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating" refers reaction in which nucleophile displaces a leaving group such as halide or sulfonate from a carbon-containing radical. Unless otherwise indicated, the term "alkylating" does not limit the carbon-containing radical to alkyl.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2SCH_2$ and $CH_3CH_2SCH_2CH_2$. "Alkylsulfinyl" includes both enantiomers of an alkylsulfinyl group. Examples of "alkylsulfinyl" include $CH_3S(O)—$, $CH_3CH_2S(O)—$, $CH_3CH_2CH_2S(O)—$, $(CH_3)_2CHS(O)_2$, and the different butylsulfinyl, pentylsulfinyl and hexylsulfinyl isomers. Examples of "alkylsulfonyl" include $CH_3S(O)_2—$, $CH_3CH_2S(O)_2—$, $CH_3CH_2CH_2S(O)_2—$, $(CH_3)_2CHS(O)_2—$, and the different butylsulfonyl, pentylsulfonyl and hexylsulfonyl isomers. "Cyanoalkyl" denotes an alkyl group substituted with one cyano group. Examples of "cyanoalkyl" include $NCCH_2$ and $NCCH_2CH_2$ (alternatively identified as $CH_2CH_2CN$). "Nitroalkyl" denotes an alkyl group substituted with one nitro group. Examples of "nitroalkyl" include $O_2NCH_2$ and $O_2NCH_2CH_2$ (alternatively identified as $CH_2CH_2NO_2$). "Cyano" means $NC—$, and "formyl" means $HC(=O)—$. "Alkylamino" includes an NH radical substituted with straight-chain or branched alkyl. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "alkylcycloalkyl" denotes an alkyl group bonded to a cycloalkyl moiety.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkoxyalkyl", "haloalkylthio", "haloalkenyl", "haloalkynyl", and the like, are as defined analogously to the term "haloalkyl". Examples of "haloalkoxy" include $CF_3O—$, $CCl_3CH_2O—$, $HCF_2CH_2CH_2O—$ and $CF_3CH_2O—$. Examples of "haloalkoxyalkyl" include $CF_3OCH_2—$, $CCl_3CH_2OCH_2—$, $HCF_2CH_2CH_2OCH_2—$ and $CF_3CH_2OCH_2—$. Examples of "haloalkylthio" include $CCl_3S—$, $CF_3S—$, $CCl_3CH_2S—$ and $ClCH_2CH_2CH_2S—$. Examples of "haloalkenyl" include $(Cl)_2C=CHCH_2—$ and $CF_3CH_2CH=CHCH_2—$. Examples of "haloalkynyl" include $HC\equiv CCHCl—$, $CF_3C\equiv C—$, $CCl_3C\equiv C—C—$ and $FCH_2C\equiv C=CH_2—$.

"Alkylcarbonyl" denotes a straight-chain or branched alkyl moiety bonded to a $C(=O)$ moiety. Examples of "alkylcarbonyl" include $CH_3C(=O)—$, $CH_3CH_2C(=O)—$, $CH_3CH_2CH_2C(=O)—$, $(CH_3)_2CHC(=O)—$ and the different butoxy- or pentoxycarbonyl isomers. "Alkoxycarbonyl" denotes a straight-chain or branched alkoxy moieties bonded to a $C(=O)$ moiety. Examples of "alkoxycarbonyl" include $CH_3OC(=O)—$, $CH_3CH_2OC(=O)—$, $CH_3CH_2CH_2OC(=O)—$, $(CH_3)_2CHOC(=O)—$ and the different butoxy- or pentoxycarbonyl isomers. The term "alkoxycarbonylalkyl" denotes a denotes a straight-chain or branched alkoxy moiety bonded to through an alkyl moiety. The term "alkylcarbonylalkyl" denotes a straight or branched alkylcarbonyl moiety bonded through an alkyl moiety. The term "alkylcarbonyloxy" include donates an alkylcarbony moiety bonded through oxygen Examples of alkylcarbonyloxy include $CH_3C(=O)O—$, $CH_3CH_2C(=O)O—$, CH$_3$CH$_2$CH$_2$C(=O)O— and (CH$_3$)$_2$CHC(=O)—. The term alkanediyl or alkenediyl refers to a linear or branched alkane or alkene linking chain respectively. Examples of alkanediyl include —CH$_2$—, —CH$_2$CH(CH$_3$)— or —CH$_2$CH$_2$CH$_2$—. Examples of alkenediyl include —CH=CH—, —CH$_2$C=CH— or —CH=C(CH$_3$)—. The term "adjacent" in the context of locating a substituent means "next to" or "immediately next to".

The total number of carbon atoms in a substituent group is indicated by the "$C_i$-$C_j$" prefix where i and j are numbers from 1 to 7. For example, $C_1$-$C_4$ alkylsulfonyl designates methylsulfonyl through butylsulfonyl; $C_2$ alkoxyalkyl designates CH$_3$OCH$_2$—; $C_3$ alkoxyalkyl designates, for example, CH$_3$CH(OCH$_3$)—, CH$_3$OCH$_2$CH$_2$— or CH$_3$CH$_2$OCH$_2$—; and $C_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a group contains a substituent which can be hydrogen, for example $R^2$ or $R^4$, then when this substituent is taken as hydrogen, it is recognized that this is equivalent to said group being unsubstituted. When one or more positions on a group are said to be "not substituted" or "unsubstituted", then hydrogen atoms are attached to take up any free valency. Unless otherwise indicated as being optionally substituted, the term "phenyl" means unsubstituted phenyl. Unless otherwise indicated as being optionally substituted, the term "benzyl" means unsubstituted benzyl.

The compounds of Formula 1 wherein L is a direct bond and G is H (i.e. the "O-L-G" substituent of Formula 1 is a hydroxy moiety) are believed to be the compounds that bind to an active site on a plant enzyme or receptor causing herbicidal effect on the plant. Other compounds of Formula 1 wherein the substituents L-G form a group that can be transformed within plants or the environment to the hydroxy moiety provide similar herbicidal effects and are within the scope of the present invention. Therefore, L-G can be any derivative known in the art which does not extinguish the herbicidal activity of the compound of Formula 1 and is or can be hydrolyzed, oxidized, reduced or otherwise metabolized in plants or soil to provide the carboxylic acid function, which depending upon pH, is in the dissociated or the undissociated form. The term "ring system" denotes two or more fused rings. The term "bicyclic ring system" denotes a ring system consisting of two fused rings.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as an enolic function (e.g., when L is a direct bond and G is H), salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

When $R^5$, $R^6$ or $R^7$ is a 5- or 6-membered nitrogen-containing heterocyclic ring, it may be attached to the remainder of Formula 1 though any available carbon or nitrogen ring atom, unless otherwise described. As noted above, $R^5$, $R^6$ or $R^7$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein $R^v$ is as a substituent on $R^5$, $R^6$ or $R^7$ as defined in the Summary of the Invention, and r is an integer.

As noted above, $R^5$, $R^6$ or $R^7$ can be (among others) a 5- or 6-membered heterocyclic ring, which may be saturated or unsaturated, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention on $R^5$, $R^6$ or $R^7$ (i.e. halogen, $C_1$-$C_4$ alkyl or $C_1$-$C_4$ haloalkyl) and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

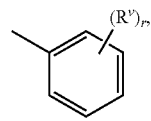
U-1

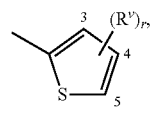
U-2

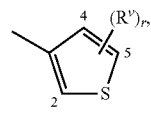
U-3

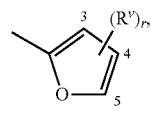
U-4

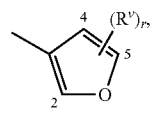
U-5

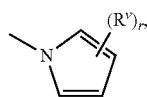
U-6

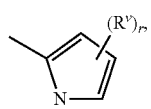
U-7

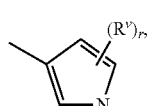
U-8

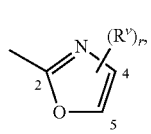
U-9

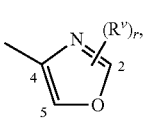
U-10

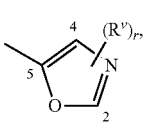
U-11

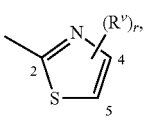
U-12

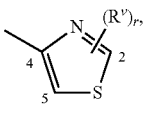
U-13

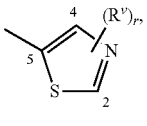
U-14

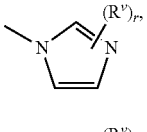
U-15

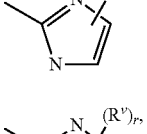
U-16

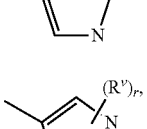
U-17

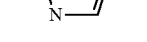
U-18

-continued
U-19 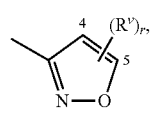
U-20 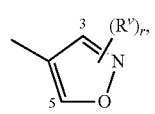
U-21 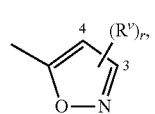
U-22 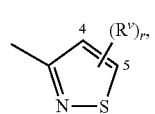
U-23 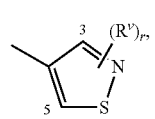
U-24 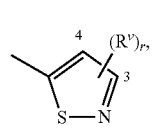
U-25 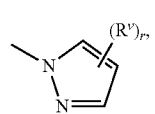
U-26 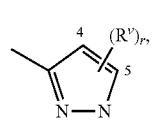
U-27 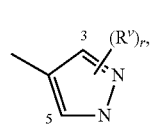
U-28 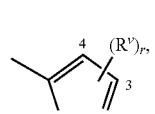
U-29 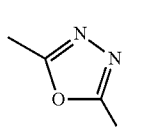
U-30 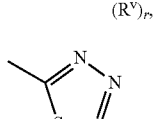
U-31 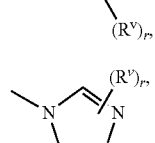
-continued
U-32 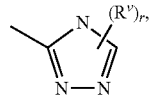
U-33 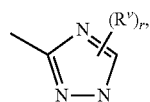
U-34 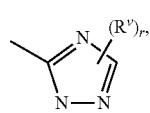
U-35 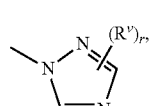
U-36 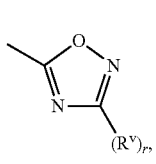
U-37 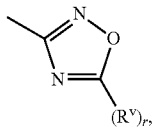
U-38 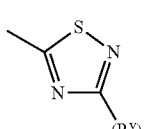
U-39 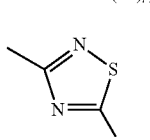
U-40 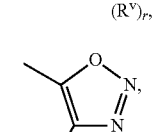
U-41 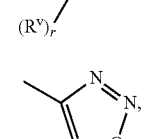
U-42 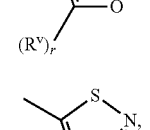
U-43 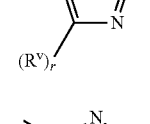
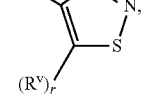

-continued

U-44 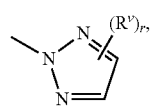

U-45 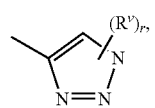

U-46 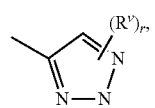

U-47 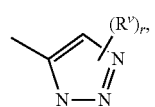

U-48 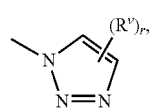

U-49 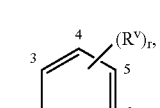

U-50 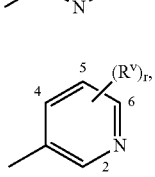

U-51 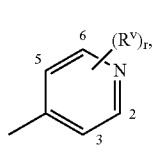

U-52 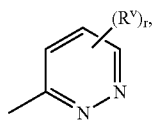

U-53 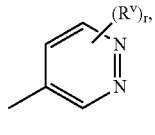

U-54 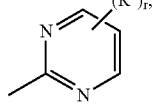

U-55 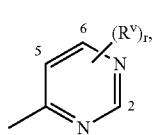

-continued

U-56 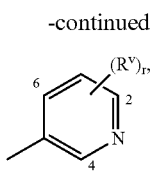

U-57 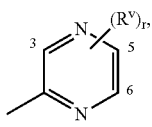

U-58 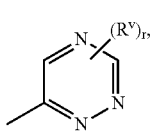

U-59 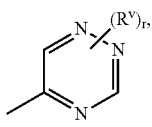

U-60 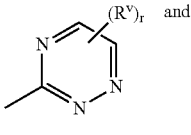

and

U-61 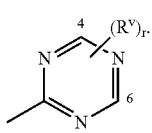

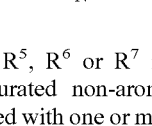

Note that when $R^5$, $R^6$ or $R^7$ is a 5- or 6-membered saturated or unsaturated non-aromatic heterocyclic ring optionally substituted with one or more substituents selected from the group of substituents as defined in the Summary of the Invention for $R^5$, $R^6$ or $R^7$, one or two carbon ring members of the heterocycle can optionally be in the oxidized form of a carbonyl moiety.

Examples of a 5- or 6-membered heterocyclic ring that is saturated or non-aromatic unsaturated heterocyclic ring containing ring members selected from up to two O atoms and up to two S atoms, and optionally substituted on carbon atom ring members with up to five halogen atoms includes the rings T-1 through T-35 as illustrated in Exhibit 2. Note that when the attachment point on the T group is illustrated as floating, the T group can be attached to the remainder of Formula 1 through any available carbon or nitrogen of the T group by replacement of a hydrogen atom. The optional substituents corresponding to $R^v$ can be attached to any available carbon or nitrogen by replacing a hydrogen atom. For these T rings, r is typically an integer from 0 to 4, limited by the number of available positions on each T group. The term "optionally substituted" means "substituted or unsubstituted". Note that when $T^2$ is N, the nitrogen atom can complete its valence by substitution with either H or the substituents corresponding to RV as defined in the Summary of the Invention on $R^5$, $R^6$ or $R^7$. Exemplary values for $R^1$ include T-1, T-2, T-7 and T-9 (i.e. when $R^1$ is, among other, a 5- or 6-membered saturated or partially saturated heterocyclic ring containing ring members selected from carbon and up to 1 O and 1 S") and T-28 through T-31 where $T^2$ is O or S.

Exhibit 2
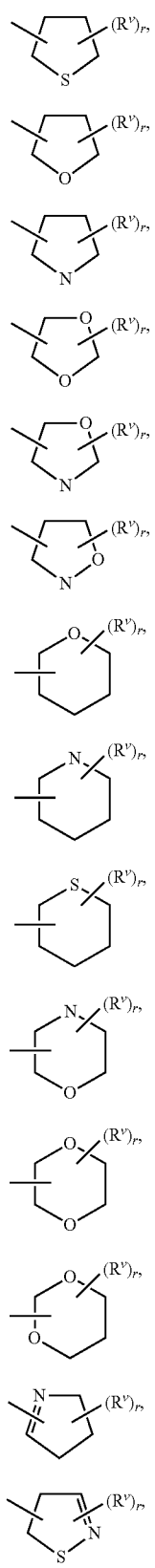
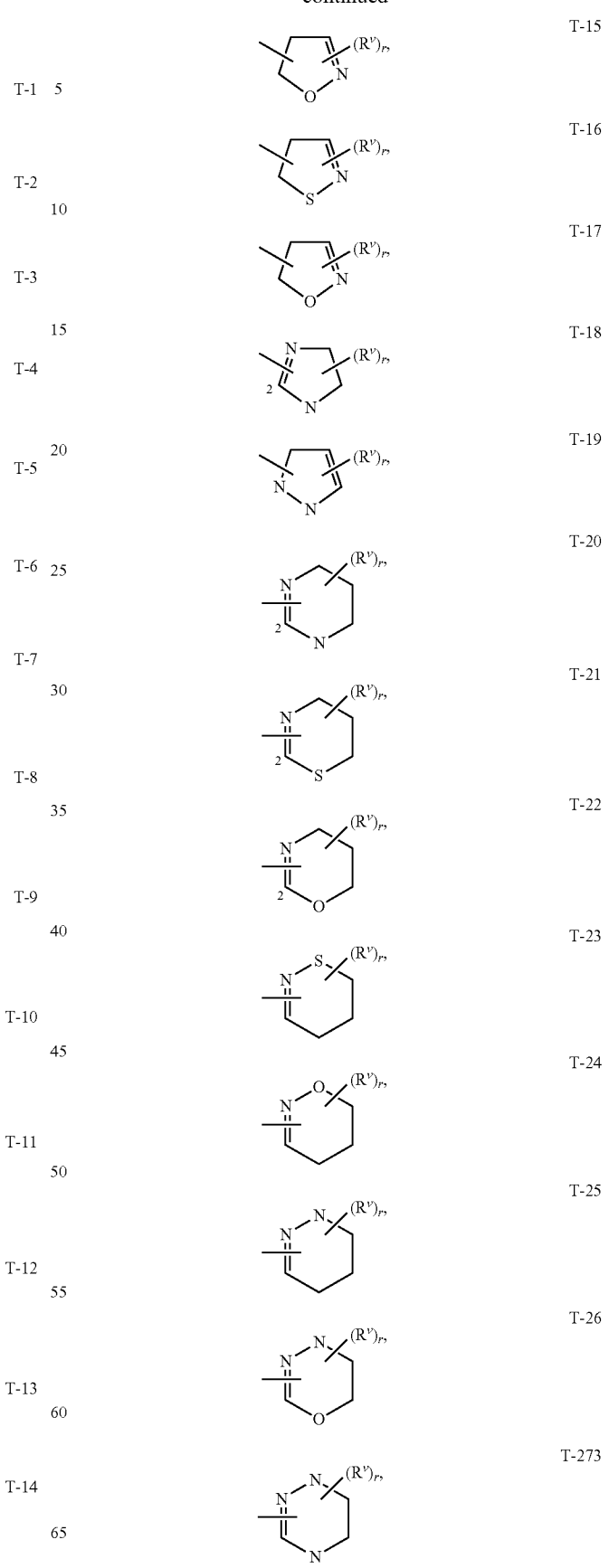

-continued

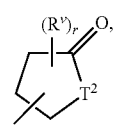
T-28

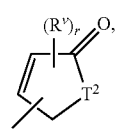
T-29

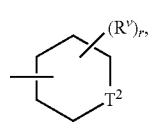
T-30

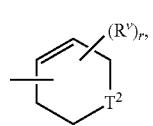
T-31

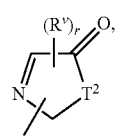
T-32

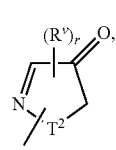
T-33

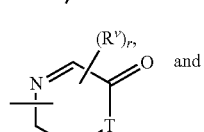 and
T-34

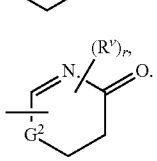
T-35

Although $R^v$ groups are shown in the structures U-1 through U-61, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Embodiments of the present invention as described in the Summary of the Invention include (where Formula 1 as used in the following Embodiments includes N-oxides and salts thereof):

Embodiment 1

A compound of Formula 1, N-oxides and salts thereof, compositions containing them, and methods of their use for controlling undesired vegetation as described in the Summary of the Invention.

Embodiment 2

A compound of Embodiment 1 wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl.

Embodiment 3

A compound of any one of Embodiments 1 or 2 wherein $R^1$ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl.

Embodiment 4

A compound of Embodiment 3 wherein $R^1$ is $C_1$-$C_4$ alkyl, $C_3$-$C_4$ cycloalkyl, $C_2$-$C_3$ cyanoalkyl, $C_1$-$C_3$ haloalkyl or $C_2$-$C_4$ alkoxyalkyl.

Embodiment 5

A compound of Embodiment 4 wherein $R^1$ is $C_1$-$C_3$ alkyl, $NCCH_2CH_2$—, $C_1$-$C_2$ haloalkyl or 2-methoxyethyl.

Embodiment 6

A compound of Embodiment 5 wherein $R^1$ is methyl, ethyl, n-propyl or 2-methoxyethyl.

Embodiment 7

A compound of Embodiment 6 wherein $R^1$ is methyl or ethyl.

Embodiment 8

A compound of Embodiment 6 wherein $R^1$ is methyl.

Embodiment 9

A compound of Embodiment 1 wherein $R^1$ is other than H.

Embodiment 10

A compound of Embodiment 1 wherein $R^1$ is other than phenyl.

Embodiment 11 compound of any one of Embodiments 1 through 10 wherein W is O.

Embodiment 12

A compound of Formula 1 or any one of Embodiments 1 through 11 wherein A is selected from A-1, A-4 and A-6.

Embodiment 13

A compound of Formula 1 or Embodiment 12 wherein A is A-1.

Embodiment 14

A compound of Formula 1 or Embodiment 12 wherein A is A-4.

Embodiment 15

A compound of Formula 1 or Embodiment 12 wherein A is A-6.

Embodiment 16

A compound of Formula 1 or Embodiment 12 wherein A is A-1 and $X^1$, $X^2$, $X^3$, $X^4$, $X^5$, $X^6$, $X^7$, $X^8$ and $X^9$ are each independently $CR^3$.

Embodiment 17

A compound of Formula 1 or Embodiment 12 wherein A is A-1 and $X^1$, $X^2$, $X^3$, $X^4$, $X^5$, $X^6$, $X^7$, $X^8$ and $X^9$ are each CH.

Embodiment 18

A compound of any one of Embodiments 1 through 17 wherein $R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy or $C_1$-$C_5$ alkylthio.

Embodiment 19

A compound of Embodiment 18 wherein $R^2$ is H, halogen, cyano, formyl, $C_1$-$C_7$ alkyl, $C_2$-$C_4$ alkylcarbonyl, $C_2$-$C_7$ alkylcarbonyloxy, $C_4$-$C_7$ alkylcycloalkyl, $C_1$-$C_4$ alkylsulfinyl, $C_1$-$C_4$ alkylsulfonyl, $C_1$-$C_4$ alkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl or $C_1$-$C_7$ alkoxy.

Embodiment 20

A compound of Embodiment 19 wherein $R^2$ is H, halogen, cyano, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy.

Embodiment 21

A compound of Embodiment 20 wherein $R^2$ is H, halogen, cyano, $C_1$-$C_3$ alkyl, cyclopropyl, $C_1$-$C_2$ haloalkyl, methoxy or ethoxy.

Embodiment 22

A compound of Embodiment 21 wherein $R^2$ is H, Cl, Br, I, cyano, methyl or methoxy.

Embodiment 23

A compound of Embodiment 22 wherein $R^2$ is H, Cl, methyl or methoxy.

Embodiment 24

A compound of Embodiment 23 wherein $R^2$ is Cl or methyl.

Embodiment 25

A compound of any one of Embodiments 1 through 23 wherein $R^2$ is other than H.

Embodiment 26

A compound of any one of Embodiments 1 through 17 wherein $R^2$ is other than phenyl.

Embodiment 27

A compound of Embodiment 18 wherein $R^2$ is halogen, $C_1$-$C_7$ alkyl, $C_1$-$C_4$ alkylamino, $C_2$-$C_8$ dialkylamino or $C_3$-$C_7$ cycloalkyl.

Embodiment 28

A compound of Embodiment 27 wherein $R^2$ is $C_1$-$C_4$ alkylamino or $C_2$-$C_8$ dialkylamino.

Embodiment 29

A compound of Formula 1 or any one of Embodiments 1 through 28 wherein L is a direct bond.

Embodiment 30

A compound of Formula 1 or any one of Embodiments 1 through 28 wherein L is a direct bond and G is H, C(=O)$R^5$, C(=S)$R^5$, $CO_2R^6$, C(=O)$SR^6$, $CONR^7R^8$ or P(=O)$R^9R^{10}$; or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_3$-$C_6$ cycloalkyl or $C_4$-$C_7$ cycloalkylalkyl.

Embodiment 31

A compound of Embodiment 30 wherein G is H, C(=O)$R^5$, $CO_2R^6$, $CONR^7R^8$ or P(=O)$R^9R^{10}$; or $C_1$-$C_4$ alkyl, $C_2$-$C_4$ alkenyl, $C_1$-$C_4$ haloalkyl, $C_2$-$C_4$ haloalkenyl, $C_2$-$C_4$ alkoxyalkyl, $C_3$-$C_6$ cycloalkyl or $C_4$-$C_7$ cycloalkylalkyl.

Embodiment 32

A compound of Embodiment 31 wherein G is H, C(=O)$R^5$, $CO_2R^6$ or P(=O)$R^9R^{10}$; or $C_1$-$C_4$ alkyl, $C_1$-$C_4$ haloalkyl, $C_2$-$C_4$ alkoxyalkyl or $C_3$-$C_6$ cycloalkyl.

Embodiment 33

A compound of Embodiment 32 wherein G is H, C(=O)$R^5$ or $CO_2R^6$; or $C_2$-$C_4$ alkoxyalkyl or $C_3$-$C_6$ cycloalkyl.

Embodiment 34

A compound of Embodiment 33 wherein G is H.

Embodiment 35

A compound of Embodiment 33 wherein G is C(=O)$R^5$.

Embodiment 36

A compound of Embodiment 33 wherein G is $CO_2R^6$.

Embodiment 37

A compound of Embodiment 33 wherein G is $C_2$-$C_4$ alkoxyalkyl.

Embodiment 38

A compound of Embodiment 33 wherein G is $C_3$-$C_6$ cycloalkyl.

Embodiment 39

A compound of Formula 1 or any one of Embodiments 1 through 28 wherein L is $C_1$-$C_2$ alkanediyl or $C_2$-$C_3$ alkenediyl.

Embodiment 40

A compound of Embodiment 39 wherein L is $C_1$-$C_2$ alkanediyl.

Embodiment 41

A compound of Embodiment 39 wherein L is $C_2$-$C_3$ alkenediyl.

Embodiment 42

A compound of Embodiment 39 wherein L is —$CH_2$— or —CH=CH—.

Embodiment 43

A compound of Embodiment 42 wherein L is —$CH_2$—.

Embodiment 44

A compound of Formula 1 or any one of Embodiments 1 through 43 wherein each $R^3$ is independently H, halogen, $C_1$-$C_3$ alkyl, $C_3$-$C_4$ cycloalkyl, $C_1$-$C_3$ haloalkyl or $C_1$-$C_3$ alkoxy.

Embodiment 45

A compound of Embodiment 44 wherein each $R^3$ is independently H, halogen, $C_1$-$C_2$ alkyl, cyclopropyl or $C_1$-$C_2$ haloalkyl.

Embodiment 46

A compound of Embodiment 45 wherein each $R^3$ is independently H, halogen, methyl, ethyl or $CF_3$.

Embodiment 47

A compound of Embodiment 46 wherein each $R^3$ is independently H, F, Cl, Br or methyl.

Embodiment 48

A compound of Embodiment 47 wherein each $R^3$ is H.

Embodiments of this invention, including Embodiments 1-48 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-48 above as well as any other embodiments described herein, and any combination thereof, pertain to the compositions and methods of the present invention.

Embodiment A

A compound of Formula 1, N-oxides and salts thereof, compositions containing them, and methods of their use for controlling undesired vegetation wherein
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl;
W is O;
A is selected from A-1, A-4 and A-6;
L is a direct bond;
G is H, C(=O)$R^5$, C(=S)$R^5$, $CO_2R^6$, C(=O)$SR^6$, $CONR^7R^8$ or P(=O)$R^9R^{10}$; or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_3$-$C_6$ cycloalkyl or $C_4$-$C_7$ cycloalkylalkyl;
$R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy or $C_1$-$C_5$ alkylthio; and
each $R^3$ is independently H, halogen, $C_1$-$C_3$ alkyl, $C_3$-$C_4$ cycloalkyl, $C_1$-$C_3$ haloalkyl or $C_1$-$C_3$ alkoxy.

Embodiment B

A compound of Embodiment A wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl;

A is A-1;
G is H, C(=O)R$^5$, CO$_2$R$^6$, CONR$^7$R$^8$ or P(=O)R$^9$R$^{10}$; or C$_1$-C$_4$ alkyl, C$_2$-C$_4$ alkenyl, C$_1$-C$_4$ haloalkyl, C$_2$-C$_4$ haloalkenyl, C$_2$-C$_4$ alkoxyalkyl, C$_3$-C$_6$ cycloalkyl or C$_4$-C$_7$ cycloalkylalkyl;
R$^2$ is H, halogen, cyano, formyl, C$_1$-C$_7$ alkyl, C$_2$-C$_4$ alkylcarbonyl, C$_2$-C$_7$ alkylcarbonyloxy, C$_4$-C$_7$ alkylcycloalkyl, C$_1$-C$_4$ alkylsulfinyl, C$_1$-C$_4$ alkylsulfonyl, C$_1$-C$_4$ alkylamino, C$_3$-C$_7$ cycloalkyl, C$_4$-C$_7$ cycloalkylalkyl, C$_2$-C$_3$ cyanoalkyl, C$_1$-C$_4$ nitroalkyl, C$_2$-C$_7$ haloalkoxyalkyl, C$_1$-C$_7$ haloalkyl, C$_2$-C$_7$ alkoxyalkyl or C$_1$-C$_7$ alkoxy; and
each R$^3$ is independently H, halogen, C$_1$-C$_2$ alkyl, cyclopropyl or C$_1$-C$_2$ haloalkyl.

Embodiment C

A compound of Embodiment B wherein
R$^1$ is C$_1$-C$_4$ alkyl, C$_3$-C$_4$ cycloalkyl, C$_2$-C$_3$ cyanoalkyl, C$_1$-C$_3$ haloalkyl or C$_2$-C$_4$ alkoxyalkyl;
G is H, C(=O)R$^5$, CO$_2$R$^6$ or P(=O)R$^9$R$^{10}$; or C$_1$-C$_4$ alkyl, C$_1$-C$_4$ haloalkyl, C$_2$-C$_4$ alkoxyalkyl or C$_3$-C$_6$ cycloalkyl;
R$^2$ is H, halogen, cyano, C$_1$-C$_4$ alkyl, C$_3$-C$_5$ cycloalkyl, C$_1$-C$_3$ haloalkyl, C$_2$-C$_4$ alkoxyalkyl or C$_1$-C$_3$ alkoxy; and
each R$^3$ is independently H, halogen, methyl, ethyl or CF$_3$.

Embodiment D

A compound of Embodiment C wherein
R$^1$ is methyl, ethyl, n-propyl or 2-methoxyethyl;
G is H, C(=O)R$^5$ or CO$_2$R$^6$; or C$_2$-C$_4$ alkoxyalkyl or C$_3$-C$_6$ cycloalkyl;
R$^2$ is H, Cl, Br, I, —CN, methyl or methoxy; and
each R$^3$ is independently H, F, Cl, Br or methyl.

Specific embodiments include compounds of Formula 1 selected from the group consisting of:
4-(9-anthracenyl)-6-chloro-5-hydroxy-2-methyl-3(2H)-pyridazinone (Compound 1);
6-chloro-4-(10-chloro-9-anthracenyl)-5-hydroxy-2-methyl-3(2H)-pyridazinone (Compound 2); and
4-(10-bromo-9-anthracenyl)-6-chloro-5-hydroxy-2-methyl-3(2H)-pyridazinone (Compound 3).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimehyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thiol]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)-N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenylpyruvate dioxygenase. Examples of HPPD inhibitors include benzobicyclon, benzofenap, bicyclopyrone (4-hydroxy-3-[[2-[2-methoxyethoxy)methyl]-6-(trifluoromethyl)-3-pyridinyl]carbonyl]bicyclo[3.2.1oct-3-en-2-one), fenquinotrione (2-[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[2-hydroxy-6-oxo-1-cyclohexen-1-yl) carbonyl]-2-methyl-1,2,4-triazine-3,5(2H,4H)-dione, 5-[2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include cyclopyrimorate (6-chloro-3-(2-cyclopropyl-6-methylphenoxy)-4-pyridazinyl 4-morpholinecarboxylate), haloxydine, pyriclor, 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

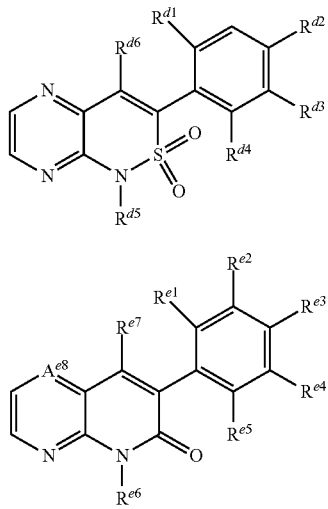

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or $-OC(=O)$-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or $C\equiv CH$; $R^{e7}$ is OH, $-OC(=O)Et$, $-OC(=O)$-i-Pr or $-OC(=O)$-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[2,6-difluorophenyl)methoxy]methyl]-4,5-dihydro-5-methyl-3-(methyl-2-thienyl)isoxazole.

"Other herbicides" (b15) also include a compound of Formula (b15A)

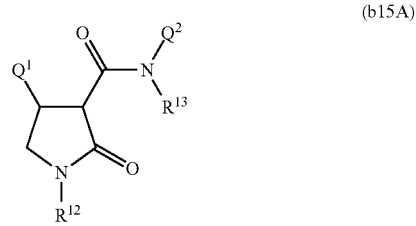

wherein
$R^{12}$ is H, $C_1$-$C_6$ alkyl, $C_1$-$C_6$ haloalkyl or $C_4$-$C_8$ cycloalkyl;
$R^{13}$ is H, $C_1$-$C_6$ alkyl or $C_1$-$C_6$ alkoxy;
$Q^1$ is an optionally substituted ring system selected from the group consisting of phenyl, thienyl, pyridinyl, benzodioxolyl, naphthyl, naphthalenyl, benzofuranyl, furanyl, benzothiophenyl and pyrazolyl, wherein when substituted said ring system is substituted by 1 to 3 $R^{14}$;
$Q^2$ is an optionally substituted ring system selected from the group consisting of phenyl, pyridinyl, benzodioxolyl, pyridinonyl, thiadiazolyl, thiazolyl, and oxazolyl, wherein when substituted said ring system is substituted by 1 to 3 $R^{15}$;
each $R^{14}$ is independently halogen, $C_1$-$C_6$ alkyl, $C_1$-$C_6$ haloalkyl, $C_1$-$C_6$ alkoxy, $C_1$-$C_6$ haloalkoxy, $C_3$-$C_8$ cyaloalkyl, cyano, $C_1$-$C_6$ alkylthio, $C_1$-$C_6$ alkylsulfinyl, $C_1$-$C_6$ alkylsulfonyl, $SF_5$, $NHR^{17}$; or phenyl optionally substituted by 1 to 3 $R^{16}$; or pyrazolyl optionally substituted by 1 to 3 $R^{16}$;
each $R^{15}$ is independently halogen, $C_1$-$C_6$ alkyl, $C_1$-$C_6$ haloalkyl, $C_1$-$C_6$ alkoxy, $C_1$-$C_6$ haloalkoxy, cyano, nitro, $C_1$-$C_6$ alkylthio, $C_1$-$C_6$ alkylsulfinyl, $C_1$-$C_6$ alkylsulfonyl;
each $R^{16}$ is independently halogen, $C_1$-$C_6$ alkyl or $C_1$-$C_6$ haloalkyl;
$R^{17}$ is $c_1c_4$ alkoxycarbonyl.

In one Embodiment wherein "other herbicides" (b15) also include a compound of Formula (b15A), it is preferred that $R^{12}$ is H or $C_1$-$C_6$ alkyl; more preferably $R^{12}$ is H or methyl. Preferably $R^{13}$ is H. Preferably $Q^1$ is either a phenyl ring or a pyridinyl ring, each ring substituted by 1 to 3 $R^{14}$; more preferably $Q^1$ is a phenyl ring substituted by 1 to 2 $R^{14}$. Preferably $Q^2$ is a phenyl ring substituted by 1 to 3 $R^{15}$; more preferably $Q^2$ is a phenyl ring substituted by 1 to 2 $R^{15}$. Preferably each $R^{14}$ is independently halogen, $C_1$-$C_4$ alkyl, $C_1$-$C_3$ haloalkyl, $C_1$-$C_3$ alkoxy or $C_1$-$C_3$ haloalkoxy; more preferably each $R^{14}$ is independently chloro, fluoro, bromo, $C_1$-$C_2$ haloalkyl, $C_1$-$C_2$ haloalkoxy or $C_1$-$C_2$ alkoxy. Preferably each $R^{15}$ is independently halogen, $C_1$-$C_4$ alkyl, $C_1$-$C_3$ haloalkoxy; more preferably each $R^{15}$ is independently chloro, fluoro, bromo, $C_1$-$C_2$ haloalkyl, $C_1$-$C_2$ haloalkoxy or $C_1$-$C_2$ alkoxy. Specifically preferred as "other herbicides" (b15) include any one of the following (b15A-1) through (b15A-15):

(b15A-1)
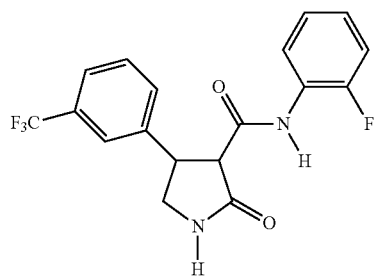
(b15A-2)
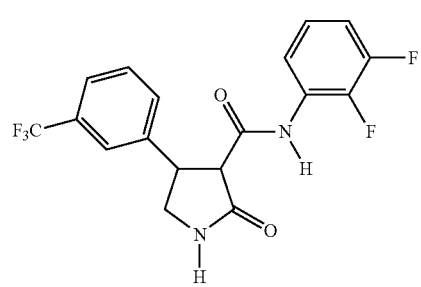
(b15A-3)
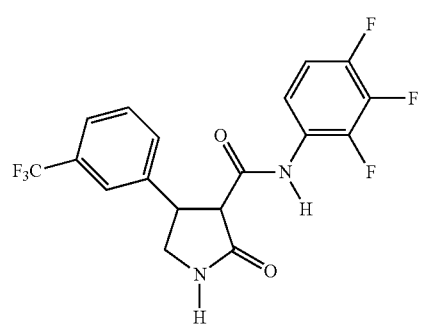
(b15A-4)
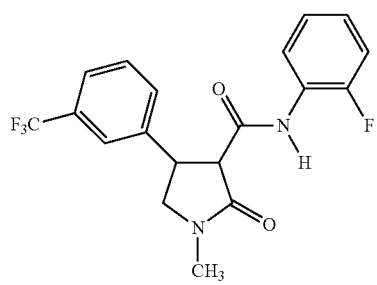
(b15A-5)
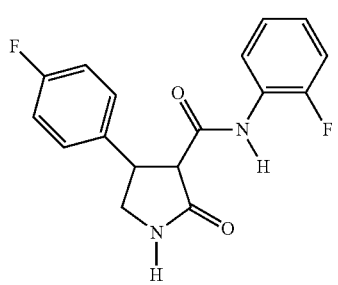
-continued
(b15A-6)
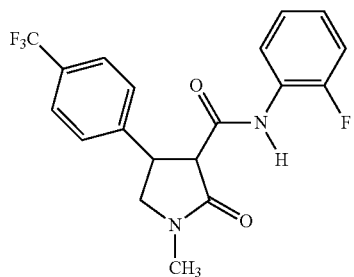
(b15A-7)
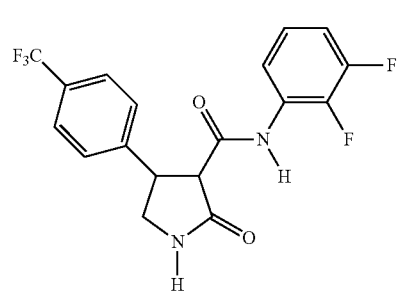
(b15A-8)
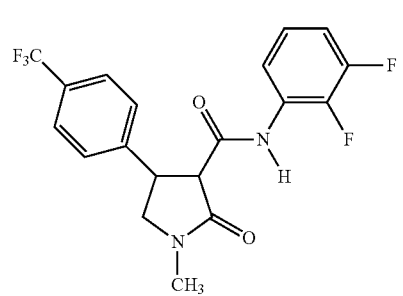
(b15A-9)
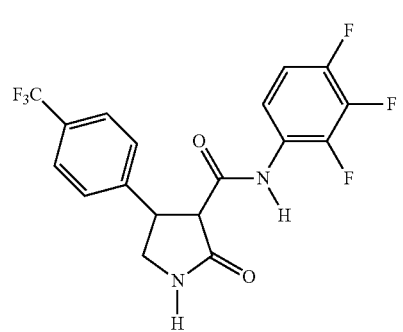
(b15A-10)
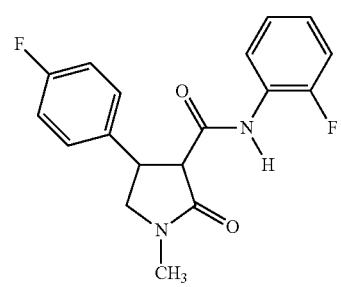

(b15A-11) 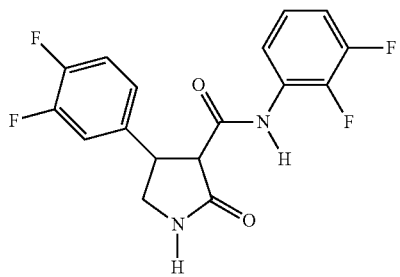

(b15A-12) 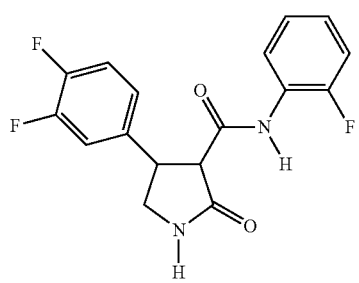

(b15A-13) 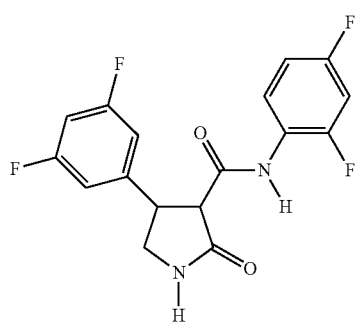

(b15A-14) 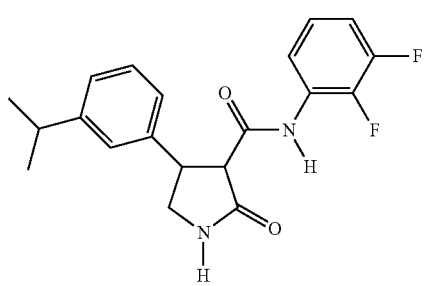

(b15A-15) 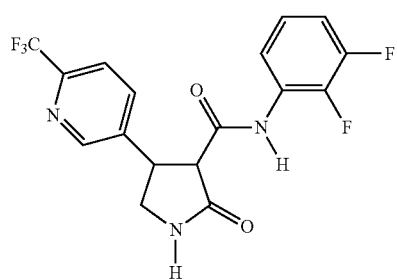

"Other herbicides" (b15) also include a compound of Formula (b15B)

(b15B) 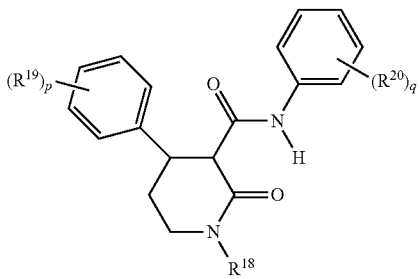

wherein $R^{18}$ is H, $C_1$-$C_6$ alkyl, $C_1$-$C_6$ haloalkyl or $C_4$-$C_8$ cycloalkyl;

each $R^{19}$ is independently halogen, $C_1$-$C_6$ haloalkyl or $C_1$-$C_6$ haloalkoxy;

p is an integer of 0, 1, 2 or 3;

each $R^{20}$ is independently halogen, $C_1$-$C_6$ haloalkyl or $C_1$-$C_6$ haloalkoxy; and q is an integer of 0, 1, 2 or 3.

In one Embodiment wherein "other herbicides" (b15) also include a compound of Formula (b15B), it is preferred that $R^{18}$ is H, methyl, ethyl or propyl; more preferably $R^{18}$ is H or methyl; most preferably $R^{18}$ is H. Preferably each $R^{19}$ is independently chloro, fluoro, $C_1$-$C_3$ haloalkyl or $C_1$-$C_3$ haloalkoxy; more preferably each $R^{19}$ is independently chloro, fluoro, $C_1$ fluoroalkyl (i.e. fluoromethyl, difluoromethyl or trifluoromethyl) or $C_1$ fluoroalkoxy (i.e. trifluoromethoxy, difluoromethoxy or fluoromethoxy). Preferably each $R^{20}$ is independently chloro, fluoro, $C_1$ haloalkyl or $C_1$ haloalkoxy; more preferably each $R^{20}$ is independently chloro, fluoro, $C_1$ fluoroalkyl (i.e. fluoromethyl, difluororm- ethyl or trifluoromethyl) or $C_1$ fluroalkoxy (i.e. trifluoromethoxy, difluoromethoxy or fluoromethoxy). Specifically preferred as "other herbicides" (b15) include any one of the following (b15B-1) through (b15B-19):

(b15B-1) 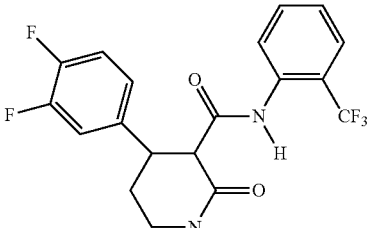

(b15B-2) 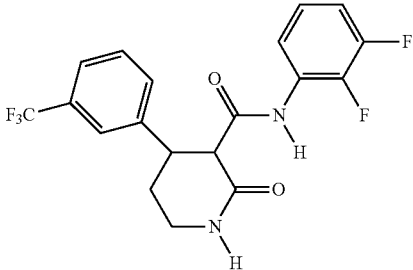

-continued
(b15B-3)
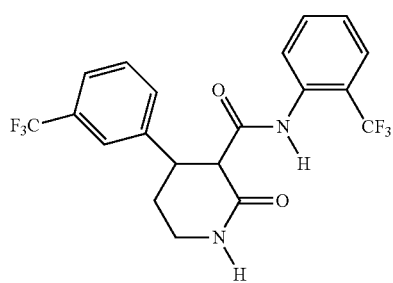
(b15B-4)
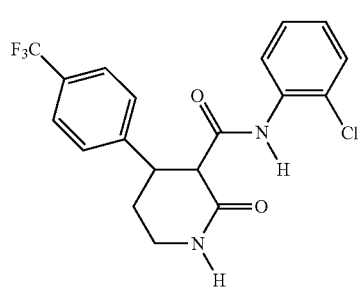
(b15B-5)
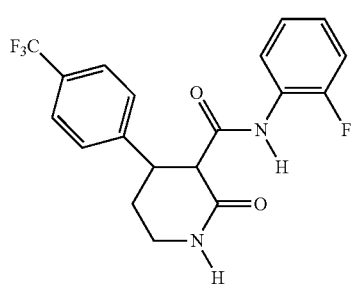
(b15B-6)
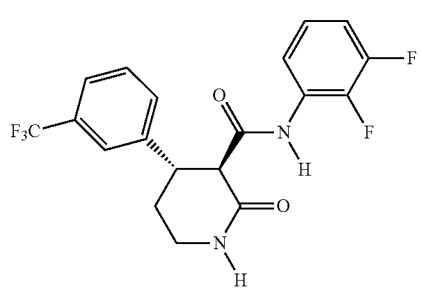
(b15B-7)
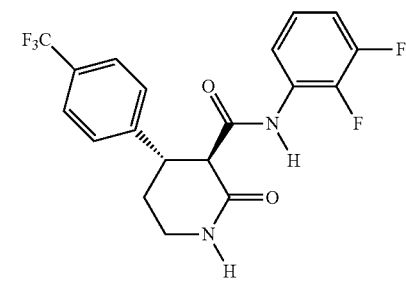
-continued
(b15B-8)
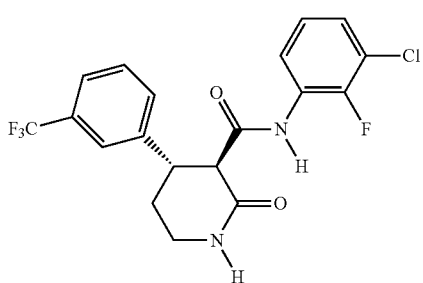
(b15B-9)
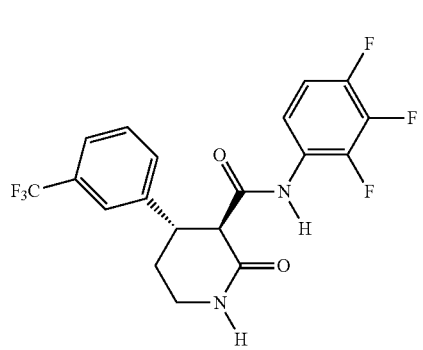
(b15B-10)
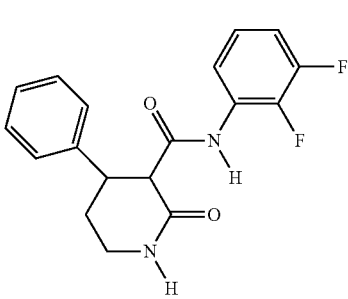
(b15B-11)
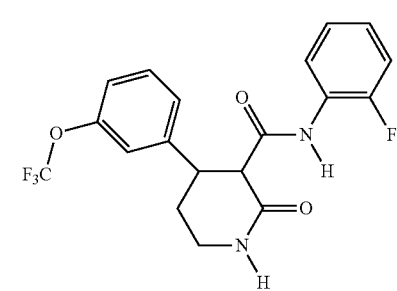
(b15B-12)
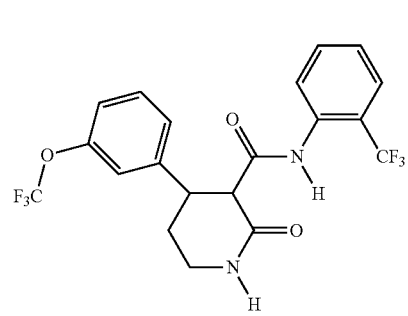

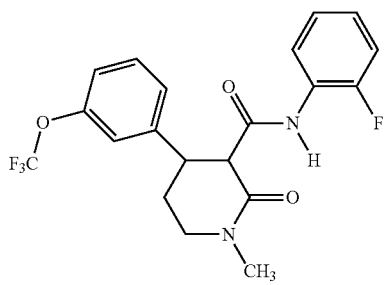 (b15B-13)

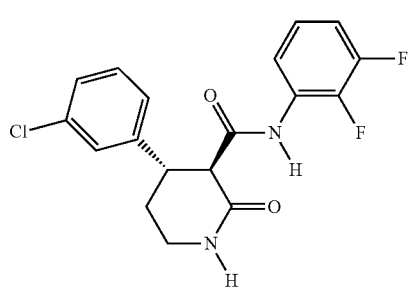 (b15B-14)

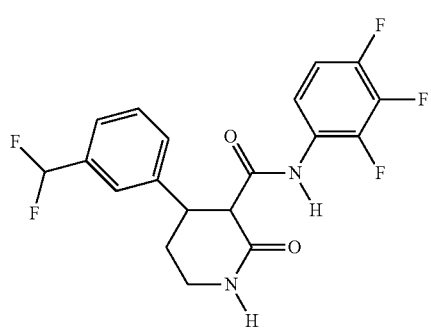 (b15B-15)

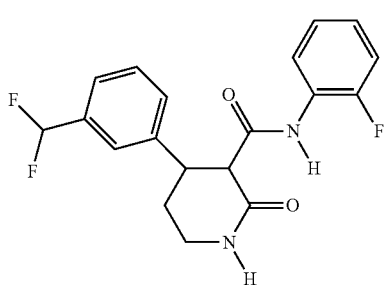 (b15B-16)

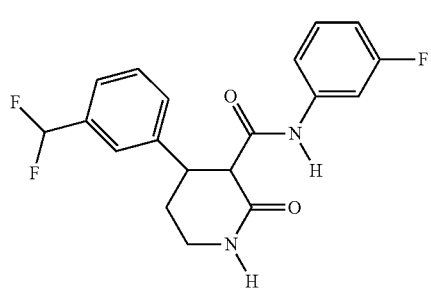 (b15B-17)

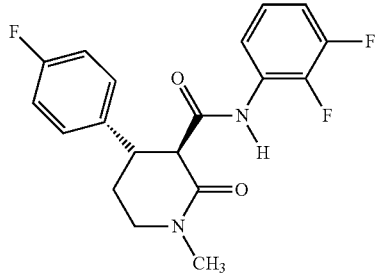 (b15B-18)

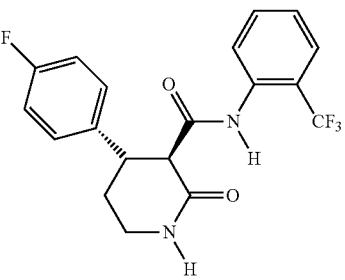 (b15B-19)

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro [4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide.

Another Embodiment wherein "other herbicides" (b15) also include a compound of Formula (b15-C),

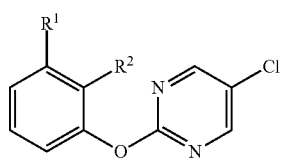 (b15C)

wherein $R^1$ is Cl, Br or CN; and $R^2$ is C(=O)CH$_2$CH$_2$CF$_3$, CH$_2$CH$_2$CH$_2$CH$_2$CF$_3$ or 3-CHF$_2$-isoxazol-5-yl.

Preferred for better control of undesired vegetation (e.g., lower use rate such as from greater-than-additive effects, broader spectrum of weeds controlled, or enhanced crop safety) or for preventing the development of resistant weeds are mixtures of a compound of this invention with a herbicide selected from the group consisting of atrazine, azimsulfuron, beflubutamid, S-beflubutamid, benzisothiazolinone, carfentrazone-ethyl, chlorimuron-ethyl, chlorsulfuron-methyl, clomazone, clopyralid potassium, cloransulam-methyl, 2-[(2,4-dichlorophenyl)methyl]-4,4-dimethyl-isoxazolidinone, 2-[2,5-dichlorophenyl)methyl]-4,4-dimethyl-isoxazolidinone, ethametsulfuron-methyl, flumetsulam, 4-(4-fluorophenyl)-6-[(2-hydroxy-6-oxo-1-cyclohexen-1-yl)carbonyl]-2-methyl-1,2,4-triazine-3,5-(2H, 4H)-dione, flupyrsulfuron-methyl, fluthiacet-methyl, fomesafen, imazethapyr, lenacil, mesotrione, metribuzin, metsulfuron-methyl, pethoxamid, picloram, pyroxasulfone, quinclorac, rimsulfuron, S-metolachlor, sulfentrazone, thifensulfuron-methyl, triflusulfuron-methyl and tribenuron-methyl.

One or more of the following methods and variations as described in Schemes 1-16 can be used to prepare compounds of Formula 1. The definitions of groups $R^1$, $R^2$, W, A, L and G in the compounds of Formulae 1-29 are as defined above in the Summary of the Invention unless otherwise noted. Formulae 1a, 1b and 1c are subsets of compounds of Formula 1, and all substituents for Formulae 1a, 1b and 1c are as defined above for Formula 1 unless otherwise noted.

As shown in Scheme 1, pyridazinones of Formula 1a (a subset of compounds of Formula 1 where W is O, and L and G are as defined above, but L is other than a direct bond and G is other than hydrogen) can be made by reacting substituted 5-hydroxy-3(2H)-pyridazinones of Formula 1b (i.e. Formula 1 wherein W is O, L is a direct bond and G is H) with a suitable electrophilic reagent of Formula 2 (i.e. $Z^1$-L-G where $Z^1$ is a leaving group, alternatively known as a nucleofuge, such as a halogen) in the presence of base in an appropriate solvent. Some examples of reagent classes representing Formula 2 wherein $Z^1$ is Cl and L is a direct bond include acid chlorides (G is —C(=O)$R^5$), chloroformates (G is —CO$_2$$R^6$), carbamoyl chlorides (G is —CONR$^7$R$^8$), sulfonyl chlorides (G is —S(O)$_2$$R^5$) and chlorosulfonamides (G is —S(O)$_2$NR$^7$R$^8$). Examples of suitable bases for this reaction include, but are not limited to, potassium carbonate, sodium hydroxide, potassium hydroxide, sodium hydride or potassium tert-butoxide and, depending on the specific base used, appropriate solvents can be protic or aprotic and used anhydrous or as aqueous mixtures. Preferred solvents for this reaction include acetonitrile, methanol, ethanol, tetrahydrofuran, diethyl ether, 1,2-dimethoxyethane, dioxane, dichloromethane or N,N-dimethylformamide. The reaction can be performed at a range of temperatures, typically ranging from 0° C. to the reflux temperature of the solvent.

Scheme 1

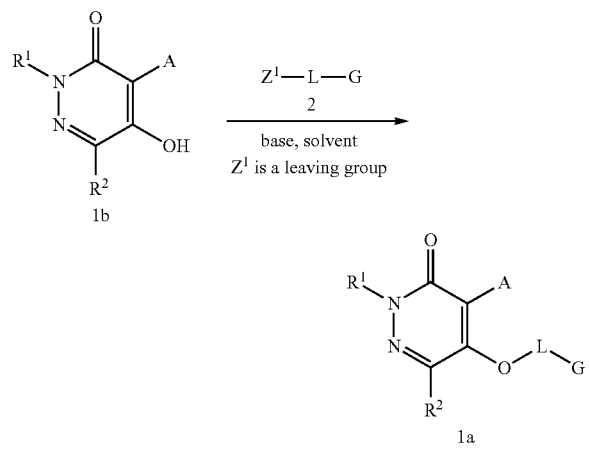

Substituted 5-hydroxy-3(2H)-pyridazinones of Formula 1b can be prepared as outlined in Scheme 2 by cyclization of hydrazide esters of Formula 3 (where $R^a$ is alkyl, typically methyl or ethyl) in the presence of base and solvent. Suitable bases for this reaction include but are not limited to potassium carbonate, sodium hydroxide, potassium hydroxide, sodium hydride, potassium t-butoxide or 1,8-diazabicyclo[5.4.0]undec-7-ene. Depending on the specific base used, appropriate solvents can be protic or aprotic and used anhydrous or as aqueous mixtures. Solvents for this cyclization include acetonitrile, methanol, ethanol, tetrahydrofuran, diethyl ether, dioxane, 1,2-dimethoxyethane, dichloromethane or N,N-dimethylformamide Temperatures for this cyclization generally range from 0° C. to the reflux temperature of the solvent. Literature methods for cyclizing hydrazide ester intermediates of formula CH$_3$(CO$_2$C$_2$H$_5$)C=NNCH$_3$C(=O)CH$_2$Ar (where Ar is a substituted phenyl instead of the bicyclic ring system shown in Formula 3) to the corresponding 4-aryl-5-hydroxy-pyridazinones are disclosed in U.S. Pat. Nos. 8,541,414 and 8,470,738. The same conditions reported in these patents are applicable to cyclizing hydrazone esters of Formula 3 to pyridazinones of Formula 1b.

Scheme 2

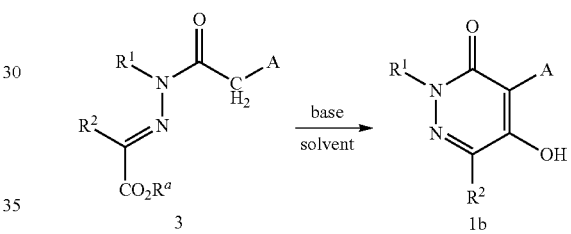

Substituted hydrazide esters of Formula 3 can be prepared as outlined in Scheme 3 by coupling a hydrazone ester of Formula 4 (where $R^a$ is alkyl, typically methyl or ethyl) with an acid chloride of Formula 5 in the presence of base and solvent. Preferred bases for this reaction are usually tertiary amines such as triethylamine or Hunig's base, but other bases can also be used, including N,N-dimethylaminopyridine, potassium carbonate, sodium hydroxide, potassium hydroxide, sodium hydride or potassium t-butoxide. Depending on the specific base used, appropriate solvents can be protic or aprotic where the reaction takes place under anhydrous conditions or as aqueous mixtures under Schotten-Baumann conditions. Solvents that are used for this acylation on nitrogen include acetonitrile, tetrahydrofuran, diethyl ether, dioxane, toluene, 1,2-dimethoxyethane, dichloromethane or N,N-dimethylformamide Temperatures for this reaction can range from 0° C. to the reflux temperature of the solvent. Methods to make related hydrazide ester intermediates of formula CH$_3$(CO$_2$C$_2$H$_5$)C=NNCH$_3$C(=O)Ar (where Ar is a substituted phenyl) have been published in the patent literature, see U.S. Pat. Nos. 8,541,414 and 8,470,738, and U.S. Patent Application Publication 2010/0267561. The procedures disclosed in these patent publications are directly applicable to making intermediates useful for preparing the present compounds as depicted in Scheme 3.

Scheme 3

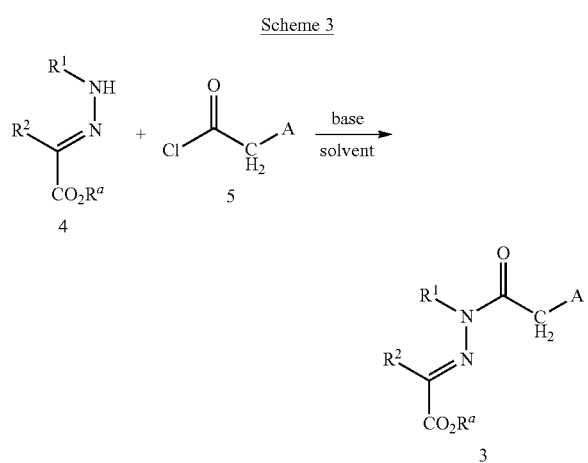

Hydrazone esters of Formula 4 are readily accessible by reaction of an appropriately substituted hydrazine of formula $R^1NHNH_2$ with a ketone or aldehyde ester of formula $R^2(C=O)CO_2R^a$ (where $R^a$ is typically methyl or ethyl) in a suitable solvent such as ethanol, methanol, acetonitrile or dioxane or dichloromethane at temperatures generally ranging from 0 to 80° C. U.S. Patent Application Publications 2007/0112038 and 2005/0256123 disclose procedures for forming the hydrazone from methylhydrazine and the keto ester $CH_3(C=O)CO_2C_2H_5$.

As shown in Scheme 4, acetyl chlorides of Formula 5 can be prepared from the corresponding acetic acid esters of Formula 6 wherein $R^b$ is typically methyl or ethyl via ester hydrolysis and acid chloride formation. Standard methods for this transformation are known in the literature. For example, ester hydrolysis can be achieved by heating an alcoholic solution of an ester of Formula 6 with an aqueous solution of an alkali metal hydroxide, following by acidification with a mineral acid. The carboxylic acid of Formula 7 formed can then be converted to the corresponding acyl chloride of Formula 5 by treatment with oxalyl chloride and a catalytic amount of N,N-dimethylformamide in an inert solvent such as dichloromethane. *J. Heterocyclic Chem.* 1983, 20(6), 1697-1703; *J. Med. Chem.* 2007, 50(1), 40-64; and PCT Patent Publications WO 2005/012291, WO 98/49141 and WO 98/49158 disclose hydrolysis of benzofuran- and benzothiophene-acetate esters to the corresponding acetic acids. *Monatshefte für Chemie* 1968, 99(2) 715-720 and patent publications WO 2004046122, WO 2009/038974 and JP09077767 disclose conversion of benzofuran- and benzothiophene-acetic acids to the corresponding acid chlorides.

Scheme 4

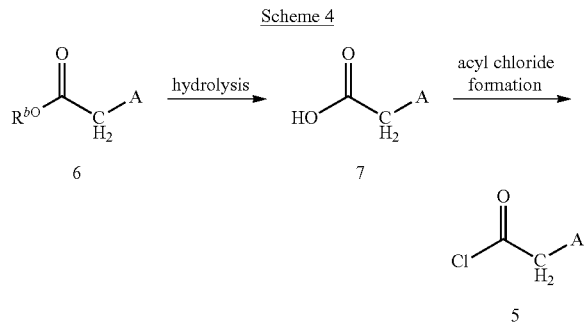

As shown in Scheme 5, heteroarylacetic acid derivatives of Formula 6c can be prepared from appropriately substituted heteroaryl amines of Formula 8. According to this method, amines of Formula 8 are diazotized (preferably with t-butyl nitrite in the presence of cupric chloride in acetonitrile) in the presence of 1,1-dichloroethene (9) to give the corresponding trichloroethylheterocycle of Formula 10. The trichloroethylheterocycle of Formula 10 are then heated with an appropriate alkali or alkaline earth alkoxide such as a sodium alkoxide of Formula 11, in a suitable solvent such as an alcohol of Formula 12, followed by acidification such as with concentrated sulfuric acid to provide the heterocyclic acetic acid esters of Formula 6c. This method is taught in *Pest. Manag. Sci.* 2011, 67, 1499-1521 and U.S. Pat. No. 5,376,677.

Scheme 5

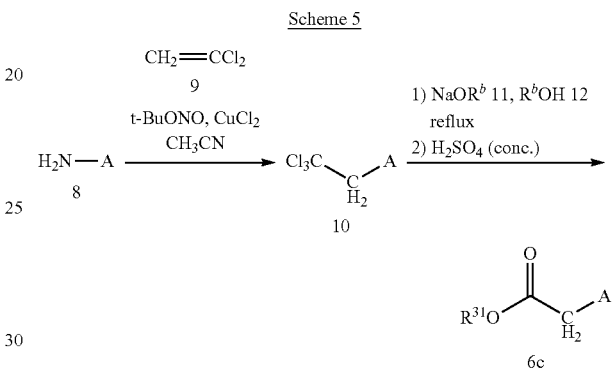

An alternative method for making heteroaryl acetic acid esters of Formula 6c is outlined in Scheme 6. As taught by the method in *Pest. Manag. Sci.* 2011, 67, 1499-1521, methyl heterocycles of Formula 13 can be brominated with N-bromosuccinimide (NBS) under free radical conditions (e.g., benzoyl peroxide as catalyst) in an inert solvent such as dichloromethane, dichloroethane or tetrachloromethane to give heteroaryl methyl bromides of Formula 14. Displacement of the bromine with cyanide by reacting compounds of Formula 14 with an alkali or alkaline cyanide (e.g., potassium cyanide) affords the heteroaryl acetonitriles of Formula 15 that can be hydrolyzed with esterification to the acetates of Formula 6c by heating in acidic alcohol (e.g., HCl in methanol or ethanol), generally at the reflux temperature of the solvent. Alcohol $R^bOH$ is a lower alkanol.

Scheme 6

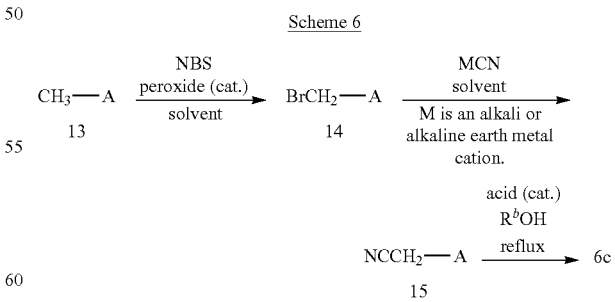

Hydrolysis of leaving groups at the 5-position of the pyridazinone ring can be accomplished as shown in Scheme 7. When the X group is lower alkoxy, lower alkylsulfide (sulfoxide or sulfone), halide or N-linked azole, it can be removed by hydrolysis with basic reagents such as tetrabutylammonium hydroxide in solvents such as tetrahydrofuran, dimethoxyethane or dioxane at temperatures from 0 to 120° C. Other hydroxide reagents useful for this hydrolysis include potassium, lithium and sodium hydroxide (see, for example, WO 2009/086041). When the X group is lower alkoxy, hydrolysis of the X group can also be accomplished with dealkylation reagents such as boron tribromide or morpholine (see, for example, WO 2009/086041, WO 2013/160126 and WO 2013/050421).

Scheme 7

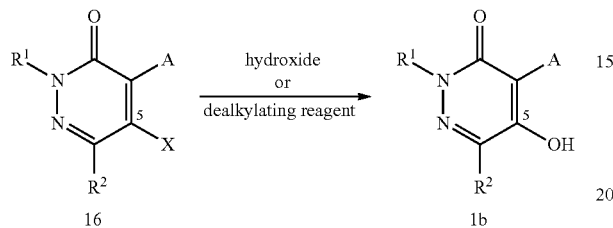

Introduction of a halogen at the 6-position of the pyridazinone can be accomplished by zincation followed by halogenation. For conditions, reagents and examples of zincation of pyridazinones, see Verhelst, T., Ph.D. thesis, University of Antwerp, 2012. Typically the pyridazinone of Formula 17 is treated in tetrahydrofuran with a solution of Zn(TMP)-LiCl or Zn(TMP)$_2$—MgCl$_2$—LiCl (i.e. 2,2,6,6-Bis(tetramethylpiperidine)zinc, magnesium chloride, lithium chloride complex in toluene/tetrahydrofuran) at –20 to 30° C. to form a zinc reagent. Subsequent addition of bromine, N-bromosuccinimide or iodine provides compounds of Formula 18 (wherein R$^2$ is Br or I, respectively). Reagents such as trichloroisocyanuric acid or 1,3-dichloro-5,5-dimethylhydantoin give a compound of Formula 18 (wherein R$^2$ is Cl). This method is shown in Scheme 8. For preparation of a variety of appropriate zincation reagents, see Wunderlich, S. Ph.D. thesis, University of Munich, 2010 and references cited therein, as well as WO 2008/138946 and WO 2010/092096. Zincation at the 6-position of the pyridazinone ring can be accomplished in the presence of aromatic/heteroaromatic substituents, alkoxy substituents or halogen at the 4-position of the pyridazinone ring, or in the presence of halogen or alkoxy substituents at the 5-position of the pyridazinone ring.

Scheme 8

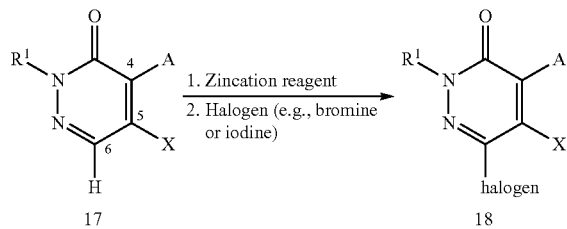

The R$^2$ substituent of compounds of Formula 19 (wherein R$^2$ is halogen or sulfonate) can be further transformed into other functional groups. Compounds wherein R$^2$ is alkyl, cycloalkyl or substituted alkyl can be prepared by transition metal catalyzed reactions of compounds of Formula 19 as shown in Scheme 9. For reviews of these types of reactions, see: E. Negishi, *Handbook of Organopalladium Chemistry for Organic Synthesis*, John Wiley and Sons, Inc., New York, 2002, N. Miyaura, *Cross-Coupling Reactions: A Practical Guide*, Springer, New York, 2002, H. C. Brown et al., *Organic Synthesis via Boranes*, Aldrich Chemical Co., Milwaukee, Vol. 3, 2002, Suzuki et al., *Chemical Reviews* 1995, 95, 2457-2483 and Molander et al., *Accounts of Chemical Research* 2007, 40, 275-286. Also see Tetrahedron Organic Chemistry Series Vol. 26: *Palladium in Heterocyclic Chemistry*, 2$^{nd}$ Ed., Gribble and Li, editors, Elsevier, Amsterdam, 2007. For a review of Buchwald-Hartwig chemistry see Yudin and Hartwig, *Catalyzed Carbon-Heteroatom Bond Formation*, 2010, Wiley, New York.

Scheme 9

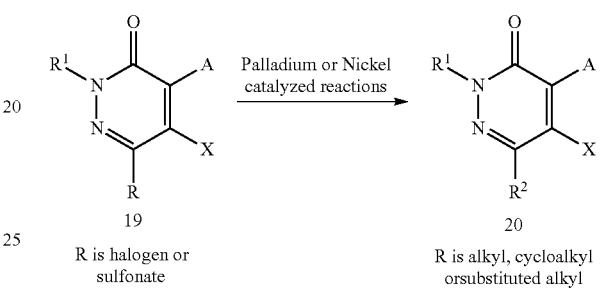

R is halogen or sulfonate    R is alkyl, cycloalkyl orsubstituted alkyl

Related synthetic methods for the introduction of other functional groups at the R$^2$ position of Formula 21 are known in the art. Copper catalyzed reactions are useful for introducing the CF$_3$ group. For a comprehensive recent review of reagents for this reaction see Wu, Neumann and Beller in *Chemistry: An Asian Journal*, 2012, ASAP, and references cited therein. For introduction of a sulfur containing substituent at this position, see methods disclosed in WO 2013/160126. For introduction of a cyano group, see WO 2014/031971. For introduction of a nitro group, see *J. Am. Chem. Soc.* 2009, 12898. For introduction of a fluoro substituent, see *J. Am. Chem. Soc.* 2014, 3792.

Compounds of Formula 19 can be prepared by reaction of organometallic reagents of Formula 22 with pyridazinones of Formula 21 with a reactive group at the 4-position, as shown in Scheme 10. Depending upon the leaving group a transition metal catalyst may be desirable. When the leaving group is lower alkoxy, N-linked azole (such as pyrazole or triazole) or sulfonate, no catalyst is required, and reaction directly with a magnesium reagent or lithium reagent can take place at the 4-position. This reaction can be done in a variety of solvents which do not react with organomagnesium reagents. Typical reaction conditions include tetrahydrofuran as the solvent, a reaction temperature of –20 to 65° C., and an excess of the organomagnesium or organolithium reagent. When the reactive group at the 4-position is halogen, a transition metal catalyst and ligand are helpful. A variety of different coupling partners can be used, including boron (Suzuki Reaction), tin (Stille Reaction), and zinc (Negishi reaction); these reactions can be catalyzed by palladium and nickel catalysts with a wide variety of ligands. Conditions for these reactions are known in the art; see, for example, *Palladium-Catalyzed Coupling Reactions: Practical Aspects and Future Development* Edited by Arpad Molnar, Wiley, 2013 and references cited within. The organomagnesium reagents used in the non-catalyzed process can be prepared by direct insertion of magnesium into a carbon-halogen bond (optionally in the presence of a lithium halide), by a Grignard exchange reaction with an i-propylmagnesium halide (optionally in the presence of a lithium halide), or by transformation of an organolithium reagent by reaction with a magnesium salt such as magnesium bromide etherate. A variety of groups which are inert toward the organomagnesium reagents can be present at $R^2$ and at the 5-position of the pyridazinone in these reactions. Compounds of Formula 21 can be prepared according to methods found in Knochel et al. *Angew.* 2011, 50, 9794-9824, and *Heterocycles* 2014, 88, 827-844.

Scheme 10

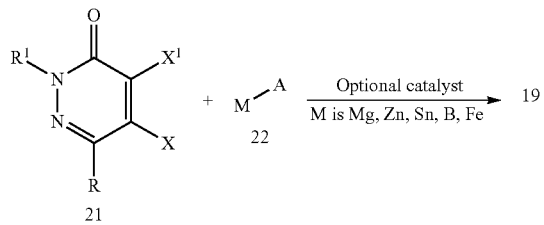

Compounds of Formula 21 are known in the art or can be prepared by methods described by Maes and Lemiere in *Comprehensive Heterocyclic Chemistry III Volume 8*, Katritsky, Ramsden, Scriven and Taylor editors and references cited therein. See also Verhelst, Ph.D. thesis University of Antwerp and references cited therein. Functional group transformations on pyridazinones are also described in Stevenson et. al. *J. Heterocyclic Chem.* 2005, 42, 427; U.S. Pat. No. 6,077,953; WO 2009/086041 and references cited therein; U.S. Pat. No. 2,782,195; WO 2013/160126; and WO 2013/050421.

Compounds of Formula 1b can also be prepared by hydrolysis of sulfones of Formula 23 in aqueous base. Suitable bases include sodium, potassium or tetrabutylammonium hydroxide. Typical reaction temperatures range from 0 to 80° C., and typical reaction times are 1-12 hours. This method is shown in Scheme 11.

Scheme 11

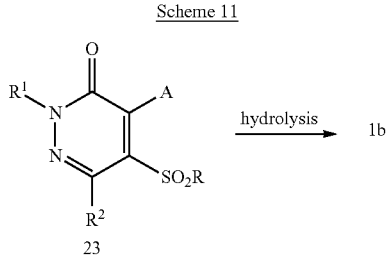

Compounds of Formula 23 can be prepared by the alkylation of compounds of Formula 24 wherein $R^1$ is H with alkyl halides and sulfonates. Typical bases useful in this method include potassium, sodium or cesium carbonate. Typical solvents include acetonitrile, tetrahydrofuran or N,N-dimethylformamide as shown in Scheme 12.

Scheme 12

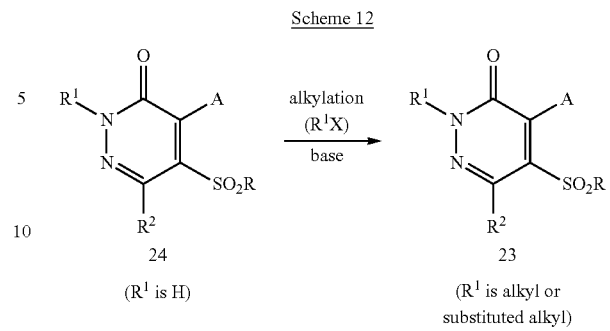

Compounds of Formula 24 can be prepared by the cyclization of compounds of Formula 25 by treatment with base. Typical bases useful in this method include potassium, sodium or cesium carbonate. Typical solvents include acetonitrile, tetrahydrofuran or N,N-dimethylformamide as shown in Scheme 13.

Scheme 13

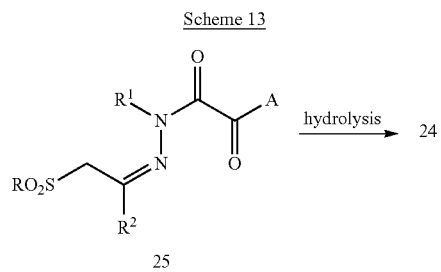

Compounds of Formula 25 can be prepared by the method shown in Scheme 14. In this method, compounds of Formula 26 are coupled with compounds of Formula 27 in the presence of a base. Bases useful in this method include triethylamine, sodium or potassium carbonate, pyridine or diisopropylethylamine.

Scheme 14

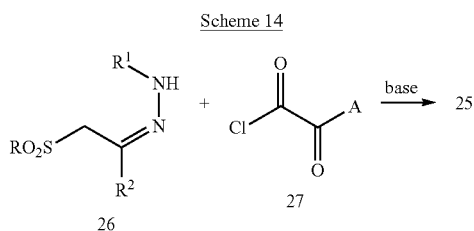

Compounds of Formula 26 can be prepared by methods known in the art.

Compounds of Formula 16 can be prepared by coupling reactions of organometallic pyridazinone coupling partners of Formula 28 with heteroaryl halides and sulfonates of Formula 29. The organometallic coupling partner can be, for example, an organozinc, organomagnesium, organotin, or organoboron reagent. Palladium catalysts such as palladium tetrakis (triphenylphosphine) and those generated from other palladium sources, such as $Pd_2dba_3$ and $Pd(OAc)_2$, and a phosphine or N-heterocyclic carbene ligand can be used in the coupling procedures (Maes et al. *J. Org. Chem.* 2011, 76, 9648-9659). Palladium precatalysts based on dialkyl biarylphosphine ligands, such as X-Phos, S-Phos and Ru- Phos (Buchwald et al. *Angew. Chem. Int. Ed.*, 2013, 52(2), 615-619), or precatalysts derived from N-heterocyclic carbene ligands such as PEPPSI-i-Pr and PEPPSI-i-Pent (Organ et al. *Eur. J. Org. Chem.* 2010, 4343-4354) can effect this coupling as well. The reaction can be carried out in solvents such as tetrahydrofuran, dimethoxyethane, N-Methyl-2-pyrrolidone and dioxane. Coupling partners may be either heterocyclic halides or sulfonates. A particularly useful class of coupling partners for the reaction are those based on nonaflates ($OSO_2C_4F_9$) of heteroaromatic compounds. Halogenated heterocyclic coupling partners are commercially available or known in the literature. Other useful classes of heterocyclic halides and synthetic routes are given in Tetrahedron Organic Chemistry Series Vol. 26: *Palladium in Heterocyclic Chemistry*, 2nd Ed., Gribble and Li, editors, Elsevier, Amsterdam, 2007.

Scheme 15

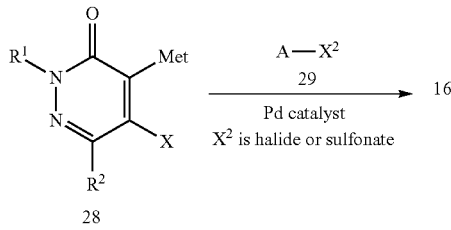

Zincation of the 4-position of a pyridazinone can be accomplished with zincation reagents such as 2,2,6,6-Bis(tetramethylpiperidine)zinc, magnesium chloride, lithium chloride complex in toluene/tetrahydrofuran (i.e. Zn(TMP)-LiCl or Zn(TMP)$_2$—MgCl$_2$—LiCl).

Magnesiation of this position can also be accomplished by treatment with Mg(TMP)-LiCl. See Verhelst, T., Ph.D. thesis, University of Antwerp, 2012 for conditions for pyridazinone metallation and for palladium catalyzed cross-coupling of 4-zincated and 4-magnesiated pyridazinones. The synthesis and cross-coupling conditions for 4-stannylpyridazinones are known from Stevenson et. al. *J. Heterocyclic Chem.* 2005, 42, 427.

As shown in Scheme 16, pyridazinones of Formula 1a (a subset of compounds of Formula 1 where W is O) can be thionated to give the corresponding thiones of Formula 1c (i.e. Formula 1 wherein W is S) with a thionation reagent that is generally phosphorus pentasulfide in pyridine or Lawesson's reagent (2,4-bis-(4-methoxyphenyl)-1,3-dithia-2,4-diphosphetane 2,4-disulfide) in an appropriate solvent (e.g., toluene, tetrahydrofuran or dioxane) at temperatures generally ranging 0° C. to room temperature.

Scheme 16

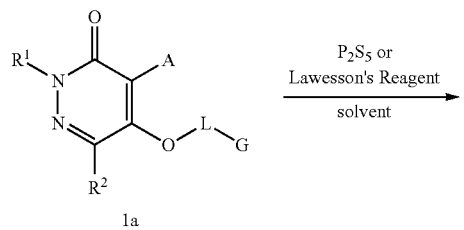

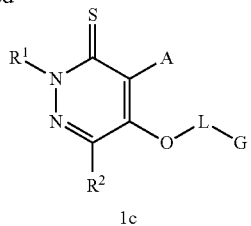

Compounds of Formula 6c, wherein A=A-1 and $R^{31}$=Et, can be prepared by the reaction of di-aryl acetic acids of Formula 30 with ethyl acrylate in the presence of palladium (II) acetate, benzoquinone, N-acetyl-isoleucine, and potassium carbonate in tert-amyl alcohol under an oxygen atmosphere, using procedures described in *Angew. Chem. Int. Ed.*, 2016, 55, 8652-8655 and as depicted in Scheme 17.

Scheme 17

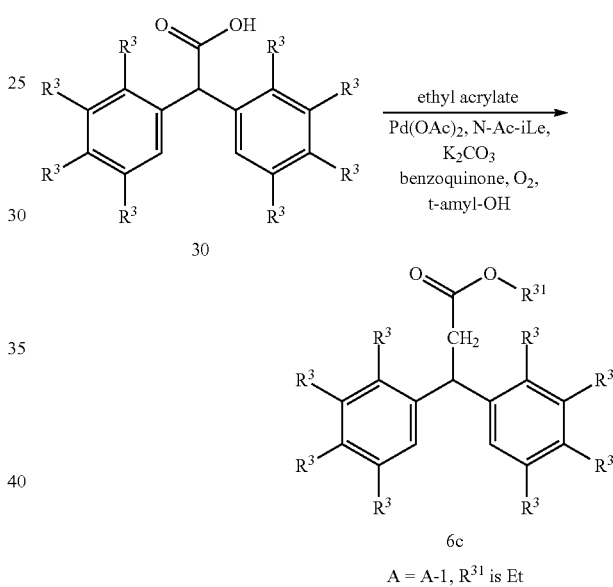

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective*

Groups in Organic Synthesis, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. All NMR spectra are reported in $CDCl_3$ downfield from tetramethylsilane at 500 MHz unless otherwise indicated where s means singlet, brs means broad singlet, d means doublet, t means triplet and m means multiplet.

SYNTHESIS EXAMPLE 1

Preparation of 4-(9-anthracenyl)-6-chloro-5-hydroxy-2-methyl-3(2H)-pyridazinone (Compound 1)

Step A: Preparation of 4-(9-anthracenyl)-6-chloro-5-methoxy-2-methyl-3(2H)-pyridazinone To a solution of 2,2,6,6-tetramethylpiperidinylmagnesium chloride lithium chloride complex solution (1.0 M in tetrahydrofuran/toluene, 38.0 mL, 38.0 mmol) was added a solution of zinc chloride (10 mL of a 1.9 M solution in 2-methyltetrahydrofuran, 19.0 mmol) at a temperature below 15° C. using an ice-water cooling bath. The resulting solution was stirred at 5° C. for 15 min and at 25° C. for 45 min. The resulting solution of bis(2,2,6,6-tetramethylpiperidinyl)zinc, lithium chloride, magnesium chloride complex was then transferred to an addition funnel and added dropwise to a suspension of 6-chloro-5-methoxy-2-methyl-3(2H)-pyridazinone (3.0 g, 17.2 mmol) and tetrahydrofuran (86 mL) at −40° C. The resulting solution was stirred at −40° C. for 15 min, warmed to 5° C., and stirred at 5° C. for 45 min. The solution was treated successively with 9-bromoanthracene (4.2 g, 16.3 mmol), and SPhos pre-catalyst-G2 (chloro(2-dicyclohexylphosphino-2',6'-dimethoxy-1,1'-biphenyl)[2-(2'-amino-1,1'-biphenyl)]palladium(II), 1.2 g, 1.7 mmol). The resulting dark brown solution was heated at the reflux temperature of the solvent for 3 h, cooled to ambient temperature, and concentrated. The residue was partitioned between ethyl acetate and saturated aqueous ammonium chloride solution, the resulting aqueous layer was extracted with ethyl acetate, and the combined organic layers were washed successively with water and brine, dried over anhydrous $MgSO_4$, filtered and concentrated to give 8.63 g of a yellow oil. The oil was purified by silica gel (330 g) column chromatography eluting with a gradient of 0% to 100% ethyl acetate in hexanes to provide 3.35 g of the title compound as an oily solid.

$^1$H NMR δ 8.57 (s, 1H), 8.08-8.03 (m, 2H), 7.69-7.63 (m, 2H), 7.53-7.45 (m, 4H), 3.82 (s, 3H), 3.05 (s, 3H).

Step B: Preparation of 4-(9-anthracenyl)-6-chloro-5-hydroxy-2-methyl-3(2H)-pyridazinone A mixture of 2.15 g (6.1 mmol) of the product from Step A and morpholine (12 mL) was heated at 100° C. for 2 h. The resulting reaction mixture was concentrated and the residue was triturated with diethyl ether. After filtration, the resulting solid was washed with diethyl ether and dried on a fitted funnel. The resulting solid was suspended in aqueous 1 N hydrochloric acid (ca. 30 mL), stirred for 2 h at ambient temperature, and filtered. The solid was washed with water and dried under vacuum to give 1.50 g of the title compound, a compound of this invention, as a light yellow solid.

$^1$H NMR (DMSO-$d_6$) δ 8.70 (s, 1H), 8.15 (d, 2H), 7.68 (d, 2H), 7.52 (t, 2H), 7.45 (t, 2H), 5.75 (s, 1H), 3.67 (s, 3H).

SYNTHESIS EXAMPLE 2

Preparation of 6-chloro-4-(10-chloro-9-anthracenyl)-5-hydroxy-2-methyl-3(2H)-pyridazinone (Compound 2)

Step A: Preparation of 6-chloro-4-(10-chloro-9-anthracenyl)-5-methoxy-2-methyl-3(2H)-pyridazinone A solution of the product of Step A of Synthesis Example 1 (143 mg, 0.41 mmol), N-chlorosuccinimide (65 mg, 0.49 mmol) and chloroform (4 mL) was stirred at room temperature for 15 h. The resulting solution was diluted with dichloromethane and washed twice with water, the organic layer was dried over anhydrous $MgSO_4$, filtered and concentrated to give 160 mg of the title compound as a yellow glass. The crude product was used in the next step without further purification.

$^1$H NMR δ 8.60 (d, 2H), 7.69 (d, 2H), 7.62 (distorted t, 2H), 7.53 (distorted t, 2H), 3.82 (s, 3H), 3.09 (s, 3H).

Step B: Preparation of 6-chloro-4-(10-chloro-9-anthracenyl)-5-hydroxy-2-methyl-3(2H)-pyridazinone A suspension of 155 mg of the product of Step A and morpholine (1 mL) was heated at 100° C. for 2 h. The resulting mixture was diluted with diethyl ether (5 mL), stirred for 30 min, and the resulting supernatant liquid was decanted away from the solid product. The solid product was partitioned between dichloromethane and aqueous 1 N hydrochloric acid, the organic layer was dried over anhydrous $MgSO_4$, filtered, and concentrated to give 120 mg of the title compound, a compound of this invention, as a yellow solid.

$^1$H NMR (DMSO-$d_6$) δ 8.52 (d, 2H), 7.61 (d, 2H), 7.74 (distorted t, 2H), 7.56 (distorted t, 2H), 3.67 (s, 3H).

By the procedures described herein together with methods known in the art, the following compounds of Tables 1 to (960) can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, c-Pr means cyclopropyl, t-Bu means tertiary butyl, Ph means phenyl, OMe means methoxy, OEt means ethoxy, SMe means methylthio, —CN means cyano, —$NO_2$ means nitro, TMS means trimethylsilyl, SOMe means methylsulfinyl, $C_2F_5$ means $CF_2CF_3$ and $SO_2Me$ means methylsulfonyl.

TABLE 1

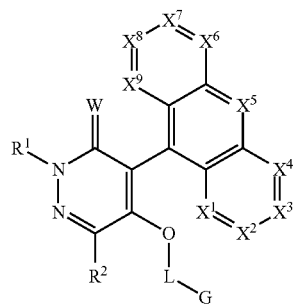

| X¹ | X² | X³ | X⁴ | X⁵ | X⁶ | X⁷ | X⁸ | X⁹ |
|---|---|---|---|---|---|---|---|---|
| CH | CH | CH | CH | CH | CH | CH | CH | CH |
| CH | CH | CH | CH | CF | CH | CH | CH | CH |
| CH | CH | CH | CH | CCl | CH | CH | CH | CH |
| CH | CH | CH | CH | CBr | CH | CH | CH | CH |
| CH | CH | CH | CH | CI | CH | CH | CH | CH |
| CH | CH | CH | CH | COCH₃ | CH | CH | CH | CH |
| CH | CH | CH | CH | CCF₃ | CH | CH | CH | CH |
| CH | CH | CH | CH | COCF₂H | CH | CH | CH | CH |
| CH | CH | CH | CH | COCF₃ | CH | CH | CH | CH |
| CH | CH | CH | CH | CCH₃ | CH | CH | CH | CH |
| CH | CH | CH | CH | CCCH₂CH₃ | CH | CH | CH | CH |
| CH | CH | CH | CH | CNO₂ | CH | CH | CH | CH |
| CH | CH | CH | CH | N | CH | CH | CH | CH |
| CH | CF | CH | CH | CH | CH | CH | CH | CH |
| CH | CCl | CH | CH | CH | CH | CH | CH | CH |
| CH | CBr | CH | CH | CH | CH | CH | CH | CH |
| CH | CI | CH | CH | CH | CH | CH | CH | CH |
| CH | COCH₃ | CH | CH | CH | CH | CH | CH | CH |
| CH | CCF₃ | CH | CH | CH | CH | CH | CH | CH |
| CH | COCF₂H | CH | CH | CH | CH | CH | CH | CH |
| CH | COCF₃ | CH | CH | CH | CH | CH | CH | CH |
| CH | CCH₃ | CH | CH | CH | CH | CH | CH | CH |
| CH | CCCH₂CH₃ | CH | CH | CH | CH | CH | CH | CH |
| CH | CNO₂ | CH | CH | CH | CH | CH | CH | CH |
| CH | N | CH | CH | CH | CH | CH | CH | CH |
| CH | CH | CH | CF | CH | CH | CH | CH | CH |
| CH | CH | CH | CCl | CH | CH | CH | CH | CH |
| CH | CH | CH | CBr | CH | CH | CH | CH | CH |
| CH | CH | CH | CI | CH | CH | CH | CH | CH |
| CH | CH | CH | COCH₃ | CH | CH | CH | CH | CH |
| CH | CH | CH | CCF₃ | CH | CH | CH | CH | CH |
| CH | CH | CH | COCF₂H | CH | CH | CH | CH | CH |
| CH | CH | CH | COCF₃ | CH | CH | CH | CH | CH |
| CH | CH | CH | CCH₃ | CH | CH | CH | CH | CH |
| CH | CH | CH | CCCH₂CH₃ | CH | CH | CH | CH | CH |
| CH | CH | CH | CNO₂ | CH | CH | CH | CH | CH |
| CH | CH | CH | N | CH | CH | CH | CH | CH |
| CH | CF | CH | CH | CH | CH | CH | CF | CH |
| CH | CF | CH | CH | CH | CH | CH | CCl | CH |
| CH | CF | CH | CH | CH | CH | CH | CBr | CH |
| CH | CF | CH | CH | CH | CH | CH | CI | CH |
| CH | CF | CH | CH | CH | CH | CH | COCH₃ | CH |
| CH | CF | CH | CH | CH | CH | CH | CCF₃ | CH |
| CH | CF | CH | CH | CH | CH | CH | COCF₂H | CH |
| CH | CF | CH | CH | CH | CH | CH | COCF₃ | CH |
| CH | CF | CH | CH | CH | CH | CH | CCH₃ | CH |
| CH | CF | CH | CH | CH | CH | CH | CCCH₂CH₃ | CH |
| CH | CF | CH | CH | CH | CH | CH | CNO₂ | CH |
| CH | CF | CH | CH | CH | CH | CH | N | CH |
| CH | CCl | CH | CH | CH | CH | CH | CCl | CH |
| CH | CCl | CH | CH | CH | CH | CH | CBr | CH |
| CH | CCl | CH | CH | CH | CH | CH | CI | CH |
| CH | CCl | CH | CH | CH | CH | CH | COCH₃ | CH |
| CH | CCl | CH | CH | CH | CH | CH | CCF₃ | CH |
| CH | CCl | CH | CH | CH | CH | CH | COCF₂H | CH |
| CH | CCl | CH | CH | CH | CH | CH | COCF₃ | CH |
| CH | CCl | CH | CH | CH | CH | CH | CCH₃ | CH |
| CH | CCl | CH | CH | CH | CH | CH | CCCH₂CH₃ | CH |
| CH | CCl | CH | CH | CH | CH | CH | CNO₂ | CH |
| CH | CCl | CH | CH | CH | CH | CH | N | CH |
| CH | CBr | CH | CH | CH | CH | CH | CBr | CH |
| CH | CBr | CH | CH | CH | CH | CH | CI | CH |
| CH | CBr | CH | CH | CH | CH | CH | COCH₃ | CH |

TABLE 1-continued

| X¹ | X² | X³ | X⁴ | X⁵ | X⁶ | X⁷ | X⁸ | X⁹ |
|---|---|---|---|---|---|---|---|---|
| CH | CBr | CH | CH | CH | CH | CH | CCF$_3$ | CH |
| CH | CBr | CH | CH | CH | CH | CH | COCF$_2$H | CH |
| CH | CBr | CH | CH | CH | CH | CH | COCF$_3$ | CH |
| CH | CBr | CH | CH | CH | CH | CH | CCH$_3$ | CH |
| CH | CBr | CH | CH | CH | CH | CH | CCH$_2$CH$_3$ | CH |
| CH | CBr | CH | CH | CH | CH | CH | CNO$_2$ | CH |
| CH | CBr | CH | CH | CH | CH | CH | N | CH |
| CH | CI | CH | CH | CH | CH | CH | CI | CH |
| CH | CI | CH | CH | CH | CH | CH | COCH$_3$ | CH |
| CH | CI | CH | CH | CH | CH | CH | CCF$_3$ | CH |
| CH | CI | CH | CH | CH | CH | CH | COCF$_2$H | CH |
| CH | CI | CH | CH | CH | CH | CH | COCF$_3$ | CH |
| CH | CI | CH | CH | CH | CH | CH | CCH$_3$ | CH |
| CH | CI | CH | CH | CH | CH | CH | CCCH$_2$CH$_3$ | CH |
| CH | CI | CH | CH | CH | CH | CH | CNO$_2$ | CH |
| CH | CI | CH | CH | CH | CH | CH | N | CH |
| CH | COCH$_3$ | CH | CH | CH | CH | CH | COCH$_3$ | CH |
| CH | COCH$_3$ | CH | CH | CH | CH | CH | CCF$_3$ | CH |
| CH | COCH$_3$ | CH | CH | CH | CH | CH | COCF$_2$H | CH |
| CH | COCH$_3$ | CH | CH | CH | CH | CH | COCF$_3$ | CH |
| CH | COCH$_3$ | CH | CH | CH | CH | CH | CCH$_3$ | CH |
| CH | COCH$_3$ | CH | CH | CH | CH | CH | CCCH$_2$CH$_3$ | CH |
| CH | COCH$_3$ | CH | CH | CH | CH | CH | CNO$_2$ | CH |
| CH | COCH$_3$ | CH | CH | CH | CH | CH | N | CH |
| CH | CCF$_3$ | CH | CH | CH | CH | CH | CCF$_3$ | CH |
| CH | CCF$_3$ | CH | CH | CH | CH | CH | COCF$_2$H | CH |
| CH | CCF$_3$ | CH | CH | CH | CH | CH | COCF$_3$ | CH |
| CH | CCF$_3$ | CH | CH | CH | CH | CH | CCH$_3$ | CH |
| CH | CCF$_3$ | CH | CH | CH | CH | CH | CCCH$_2$CH$_3$ | CH |
| CH | CCF$_3$ | CH | CH | CH | CH | CH | CNO$_2$ | CH |
| CH | CCF$_3$ | CH | CH | CH | CH | CH | N | CH |
| CH | COCF$_2$H | CH | CH | CH | CH | CH | COCF$_2$H | CH |
| CH | COCF$_2$H | CH | CH | CH | CH | CH | COCF$_3$ | CH |
| CH | COCF$_2$H | CH | CH | CH | CH | CH | CCH$_3$ | CH |
| CH | COCF$_2$H | CH | CH | CH | CH | CH | CCCH$_2$CH$_3$ | CH |
| CH | COCF$_2$H | CH | CH | CH | CH | CH | CNO$_2$ | CH |
| CH | COCF$_2$H | CH | CH | CH | CH | CH | N | CH |
| CH | COCF$_3$ | CH | CH | CH | CH | CH | COCF$_3$ | CH |
| CH | COCF$_3$ | CH | CH | CH | CH | CH | CCH$_3$ | CH |
| CH | COCF$_3$ | CH | CH | CH | CH | CH | CCCH$_2$CH$_3$ | CH |
| CH | COCF$_3$ | CH | CH | CH | CH | CH | CNO$_2$ | CH |
| CH | COCF$_3$ | CH | CH | CH | CH | CH | N | CH |
| CH | CCH$_3$ | CH | CH | CH | CH | CH | CCH$_3$ | CH |
| CH | CCH$_3$ | CH | CH | CH | CH | CH | CCCH$_2$CH$_3$ | CH |
| CH | CCH$_3$ | CH | CH | CH | CH | CH | CNO$_2$ | CH |
| CH | CCH$_3$ | CH | CH | CH | CH | CH | N | CH |
| CH | CCCH$_2$CH$_3$ | CH | CH | CH | CH | CH | CCCH$_2$CH$_3$ | CH |
| CH | CCCH$_2$CH$_3$ | CH | CH | CH | CH | CH | CNO$_2$ | CH |
| CH | CCCH$_2$CH$_3$ | CH | CH | CH | CH | CH | N | CH |
| CH | CNO$_2$ | CH | CH | CH | CH | CH | CNO$_2$ | CH |
| CH | CNO$_2$ | CH | CH | CH | CH | CH | N | CH |
| CH | N | CH | CH | CH | CH | CH | N | CH |
| CH | CF | CH | CH | CCl | CH | CH | CH | CH |
| CH | CCl | CH | CH | CCl | CH | CH | CH | CH |
| CH | CBr | CH | CH | CCl | CH | CH | CH | CH |
| CH | CI | CH | CH | CCl | CH | CH | CH | CH |
| CH | COCH$_3$ | CH | CH | CCl | CH | CH | CH | CH |
| CH | CCF$_3$ | CH | CH | CCl | CH | CH | CH | CH |
| CH | COCF$_2$H | CH | CH | CCl | CH | CH | CH | CH |
| CH | COCF$_3$ | CH | CH | CCl | CH | CH | CH | CH |
| CH | CCH$_3$ | CH | CH | CCl | CH | CH | CH | CH |
| CH | CCCH$_2$CH$_3$ | CH | CH | CCl | CH | CH | CH | CH |
| CH | CNO$_2$ | CH | CH | CCl | CH | CH | CH | CH |

TABLE 1-continued

| X¹ | X² | X³ | X⁴ | X⁵ | X⁶ | X⁷ | X⁸ | X⁹ |
|---|---|---|---|---|---|---|---|---|
| CH | N | CH | CH | CCl | CH | CH | CH | CH |
| CH | CF | CH | CH | CBr | CH | CH | CH | CH |
| CH | CCl | CH | CH | CBr | CH | CH | CH | CH |
| CH | CBr | CH | CH | CBr | CH | CH | CH | CH |
| CH | CI | CH | CH | CBr | CH | CH | CH | CH |
| CH | COCH₃ | CH | CH | CBr | CH | CH | CH | CH |
| CH | CCF₃ | CH | CH | CBr | CH | CH | CH | CH |
| CH | COCF₂H | CH | CH | CBr | CH | CH | CH | CH |
| CH | COCF₃ | CH | CH | CBr | CH | CH | CH | CH |
| CH | CCH₃ | CH | CH | CBr | CH | CH | CH | CH |
| CH | CCCH₂CH₃ | CH | CH | CBr | CH | CH | CH | CH |
| CH | CNO₂ | CH | CH | CBr | CH | CH | CH | CH |
| CH | N | CH | CH | CBr | CH | CH | CH | CH |
| CH | CF | CH | CH | CCl | CH | CH | CF | CH |
| CH | CF | CH | CH | CCl | CH | CH | CCl | CH |
| CH | CF | CH | CH | CCl | CH | CH | CBr | CH |
| CH | CF | CH | CH | CCl | CH | CH | CI | CH |
| CH | CF | CH | CH | CCl | CH | CH | COCH₃ | CH |
| CH | CF | CH | CH | CCl | CH | CH | CCF₃ | CH |
| CH | CF | CH | CH | CCl | CH | CH | COCF₂H | CH |
| CH | CF | CH | CH | CCl | CH | CH | COCF₃ | CH |
| CH | CF | CH | CH | CCl | CH | CH | CCH₃ | CH |
| CH | CF | CH | CH | CCl | CH | CH | CCCH₂CH₃ | CH |
| CH | CF | CH | CH | CCl | CH | CH | CNO₂ | CH |
| CH | CF | CH | CH | CCl | CH | CH | N | CH |
| CH | CCl | CH | CH | CCl | CH | CH | CCl | CH |
| CH | CCl | CH | CH | CCl | CH | CH | CBr | CH |
| CH | CCl | CH | CH | CCl | CH | CH | CI | CH |
| CH | CCl | CH | CH | CCl | CH | CH | COCH₃ | CH |
| CH | CCl | CH | CH | CCl | CH | CH | CCF₃ | CH |
| CH | CCl | CH | CH | CCl | CH | CH | COCF₂H | CH |
| CH | CCl | CH | CH | CCl | CH | CH | COCF₃ | CH |
| CH | CCl | CH | CH | CCl | CH | CH | CCH₃ | CH |
| CH | CCl | CH | CH | CCl | CH | CH | CCCH₂CH₃ | CH |
| CH | CCl | CH | CH | CCl | CH | CH | CNO₂ | CH |
| CH | CCl | CH | CH | CCl | CH | CH | N | CH |
| CH | CBr | CH | CH | CCl | CH | CH | CBr | CH |
| CH | CBr | CH | CH | CCl | CH | CH | CI | CH |
| CH | CBr | CH | CH | CCl | CH | CH | COCH₃ | CH |
| CH | CBr | CH | CH | CCl | CH | CH | CCF₃ | CH |
| CH | CBr | CH | CH | CCl | CH | CH | COCF₂H | CH |
| CH | CBr | CH | CH | CCl | CH | CH | COCF₃ | CH |
| CH | CBr | CH | CH | CCl | CH | CH | CCH₃ | CH |
| CH | CBr | CH | CH | CCl | CH | CH | CCCH₂CH₃ | CH |
| CH | CBr | CH | CH | CCl | CH | CH | CNO₂ | CH |
| CH | CBr | CH | CH | CCl | CH | CH | N | CH |
| CH | CI | CH | CH | CCl | CH | CH | CI | CH |
| CH | CI | CH | CH | CCl | CH | CH | COCH₃ | CH |
| CH | CI | CH | CH | CCl | CH | CH | CCF₃ | CH |
| CH | CI | CH | CH | CCl | CH | CH | COCF₂H | CH |
| CH | CI | CH | CH | CCl | CH | CH | COCF₃ | CH |
| CH | CI | CH | CH | CCl | CH | CH | CCH₃ | CH |
| CH | CI | CH | CH | CCl | CH | CH | CCCH₂CH₃ | CH |
| CH | CI | CH | CH | CCl | CH | CH | CNO₂ | CH |
| CH | CI | CH | CH | CCl | CH | CH | N | CH |
| CH | COCH₃ | CH | CH | CCl | CH | CH | COCH₃ | CH |
| CH | COCH₃ | CH | CH | CCl | CH | CH | CCF₃ | CH |
| CH | COCH₃ | CH | CH | CCl | CH | CH | COCF₂H | CH |
| CH | COCH₃ | CH | CH | CCl | CH | CH | COCF₃ | CH |
| CH | COCH₃ | CH | CH | CCl | CH | CH | CCH₃ | CH |
| CH | COCH₃ | CH | CH | CCl | CH | CH | CCCH₂CH₃ | CH |
| CH | COCH₃ | CH | CH | CCl | CH | CH | CNO₂ | CH |
| CH | COCH₃ | CH | CH | CCl | CH | CH | N | CH |

TABLE 1-continued

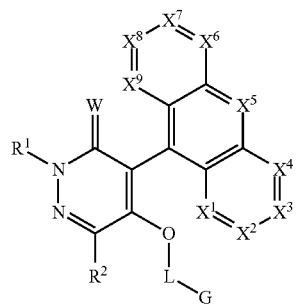

| X¹ | X² | X³ | X⁴ | X⁵ | X⁶ | X⁷ | X⁸ | X⁹ |
|---|---|---|---|---|---|---|---|---|
| CH | CCF₃ | CH | CH | CCl | CH | CH | CCF₃ | CH |
| CH | CCF₃ | CH | CH | CCl | CH | CH | COCF₂H | CH |
| CH | CCF₃ | CH | CH | CCl | CH | CH | COCF₃ | CH |
| CH | CCF₃ | CH | CH | CCl | CH | CH | CCH₃ | CH |
| CH | CCF₃ | CH | CH | CCl | CH | CH | CCCH₂CH₃ | CH |
| CH | CCF₃ | CH | CH | CCl | CH | CH | CNO₂ | CH |
| CH | CCF₃ | CH | CH | CCl | CH | CH | N | CH |
| CH | COCF₂H | CH | CH | CCl | CH | CH | COCF₂H | CH |
| CH | COCF₂H | CH | CH | CCl | CH | CH | COCF₃ | CH |
| CH | COCF₂H | CH | CH | CCl | CH | CH | CCH₃ | CH |
| CH | COCF₂H | CH | CH | CCl | CH | CH | CCCH₂CH₃ | CH |
| CH | COCF₂H | CH | CH | CCl | CH | CH | CNO₂ | CH |
| CH | COCF₂H | CH | CH | CCl | CH | CH | N | CH |
| CH | COCF₃ | CH | CH | CCl | CH | CH | COCF₃ | CH |
| CH | COCF₃ | CH | CH | CCl | CH | CH | CCH₃ | CH |
| CH | COCF₃ | CH | CH | CCl | CH | CH | CCCH₂CH₃ | CH |
| CH | COCF₃ | CH | CH | CCl | CH | CH | CNO₂ | CH |
| CH | COCF₃ | CH | CH | CCl | CH | CH | N | CH |
| CH | CCH₃ | CH | CH | CCl | CH | CH | CCH₃ | CH |
| CH | CCH₃ | CH | CH | CCl | CH | CH | CCCH₂CH₃ | CH |
| CH | CCH₃ | CH | CH | CCl | CH | CH | CNO₂ | CH |
| CH | CCH₃ | CH | CH | CCl | CH | CH | N | CH |
| CH | CCCH₂CH₃ | CH | CH | CCl | CH | CH | CCCH₂CH₃ | CH |
| CH | CCCH₂CH₃ | CH | CH | CCl | CH | CH | CNO₂ | CH |
| CH | CCCH₂CH₃ | CH | CH | CCl | CH | CH | N | CH |
| CH | C—NO₂ | CH | CH | CCl | CH | CH | CNO₂ | CH |
| CH | C—NO₂ | CH | CH | CCl | CH | CH | N | CH |
| CH | N | CH | CH | CCl | CH | CH | N | CH |
| CH | CF | CH | CH | CBr | CH | CH | CF | CH |
| CH | CF | CH | CH | CBr | CH | CH | CCl | CH |
| CH | CF | CH | CH | CBr | CH | CH | CBr | CH |
| CH | CF | CH | CH | CBr | CH | CH | CI | CH |
| CH | CF | CH | CH | CBr | CH | CH | COCH₃ | CH |
| CH | CF | CH | CH | CBr | CH | CH | CCF₃ | CH |
| CH | CF | CH | CH | CBr | CH | CH | COCF₂H | CH |
| CH | CF | CH | CH | CBr | CH | CH | COCF₃ | CH |
| CH | CF | CH | CH | CBr | CH | CH | CCH₃ | CH |
| CH | CF | CH | CH | CBr | CH | CH | CCCH₂CH₃ | CH |
| CH | CF | CH | CH | CBr | CH | CH | CNO₂ | CH |
| CH | CF | CH | CH | CBr | CH | CH | N | CH |
| CH | CCl | CH | CH | CBr | CH | CH | CCl | CH |
| CH | CCl | CH | CH | CBr | CH | CH | CBr | CH |
| CH | CCl | CH | CH | CBr | CH | CH | CI | CH |
| CH | CCl | CH | CH | CBr | CH | CH | COCH₃ | CH |
| CH | CCl | CH | CH | CBr | CH | CH | CCF₃ | CH |
| CH | CCl | CH | CH | CBr | CH | CH | COCF₂H | CH |
| CH | CCl | CH | CH | CBr | CH | CH | COCF₃ | CH |
| CH | CCl | CH | CH | CBr | CH | CH | CCH₃ | CH |
| CH | CCl | CH | CH | CBr | CH | CH | CCCH₂CH₃ | CH |
| CH | CCl | CH | CH | CBr | CH | CH | CNO₂ | CH |
| CH | CCl | CH | CH | CBr | CH | CH | N | CH |
| CH | CBr | CH | CH | CBr | CH | CH | CBr | CH |
| CH | CBr | CH | CH | CBr | CH | CH | CI | CH |
| CH | CBr | CH | CH | CBr | CH | CH | COCH₃ | CH |
| CH | CBr | CH | CH | CBr | CH | CH | CCF₃ | CH |
| CH | CBr | CH | CH | CBr | CH | CH | COCF₂H | CH |
| CH | CBr | CH | CH | CBr | CH | CH | COCF₃ | CH |
| CH | CBr | CH | CH | CBr | CH | CH | CCH₃ | CH |
| CH | CBr | CH | CH | CBr | CH | CH | CCCH₂CH₃ | CH |
| CH | CBr | CH | CH | CBr | CH | CH | CNO₂ | CH |
| CH | CBr | CH | CH | CBr | CH | CH | N | CH |
| CH | CI | CH | CH | CBr | CH | CH | CI | CH |
| CH | CI | CH | CH | CBr | CH | CH | COCH₃ | CH |

TABLE 1-continued

| X¹ | X² | X³ | X⁴ | X⁵ | X⁶ | X⁷ | X⁸ | X⁹ |
|---|---|---|---|---|---|---|---|---|
| CH | CI | CH | CH | CBr | CH | CH | CCF$_3$ | CH |
| CH | CI | CH | CH | CBr | CH | CH | COCF$_2$H | CH |
| CH | CI | CH | CH | CBr | CH | CH | COCF$_3$ | CH |
| CH | CI | CH | CH | CBr | CH | CH | CCH$_3$ | CH |
| CH | CI | CH | CH | CBr | CH | CH | CCCH$_2$CH$_3$ | CH |
| CH | CI | CH | CH | CBr | CH | CH | CNO$_2$ | CH |
| CH | CI | CH | CH | CBr | CH | CH | N | CH |
| CH | COCH$_3$ | CH | CH | CBr | CH | CH | COCH$_3$ | CH |
| CH | COCH$_3$ | CH | CH | CBr | CH | CH | CCF$_3$ | CH |
| CH | COCH$_3$ | CH | CH | CBr | CH | CH | COCF$_2$H | CH |
| CH | COCH$_3$ | CH | CH | CBr | CH | CH | COCF$_3$ | CH |
| CH | COCH$_3$ | CH | CH | CBr | CH | CH | CCH$_3$ | CH |
| CH | COCH$_3$ | CH | CH | CBr | CH | CH | CCCH$_2$CH$_3$ | CH |
| CH | COCH$_3$ | CH | CH | CBr | CH | CH | CNO$_2$ | CH |
| CH | COCH$_3$ | CH | CH | CBr | CH | CH | N | CH |
| CH | CCF$_3$ | CH | CH | CBr | CH | CH | CCF$_3$ | CH |
| CH | CCF$_3$ | CH | CH | CBr | CH | CH | COCF$_2$H | CH |
| CH | CCF$_3$ | CH | CH | CBr | CH | CH | COCF$_3$ | CH |
| CH | CCF$_3$ | CH | CH | CBr | CH | CH | CCH$_3$ | CH |
| CH | CCF$_3$ | CH | CH | CBr | CH | CH | CCCH$_2$CH$_3$ | CH |
| CH | CCF$_3$ | CH | CH | CBr | CH | CH | CNO$_2$ | CH |
| CH | CCF$_3$ | CH | CH | CBr | CH | CH | N | CH |
| CH | COCF$_2$H | CH | CH | CBr | CH | CH | COCF$_2$H | CH |
| CH | COCF$_2$H | CH | CH | CBr | CH | CH | COCF$_3$ | CH |
| CH | COCF$_2$H | CH | CH | CBr | CH | CH | CCH$_3$ | CH |
| CH | COCF$_2$H | CH | CH | CBr | CH | CH | CCCH$_2$CH$_3$ | CH |
| CH | COCF$_2$H | CH | CH | CBr | CH | CH | CNO$_2$ | CH |
| CH | COCF$_2$H | CH | CH | CBr | CH | CH | N | CH |
| CH | COCF$_3$ | CH | CH | CBr | CH | CH | COCF$_3$ | CH |
| CH | COCF$_3$ | CH | CH | CBr | CH | CH | CCH$_3$ | CH |
| CH | COCF$_3$ | CH | CH | CBr | CH | CH | CCCH$_2$CH$_3$ | CH |
| CH | COCF$_3$ | CH | CH | CBr | CH | CH | CNO$_2$ | CH |
| CH | COCF$_3$ | CH | CH | CBr | CH | CH | N | CH |
| CH | CCH$_3$ | CH | CH | CBr | CH | CH | CCH$_3$ | CH |
| CH | CCH$_3$ | CH | CH | CBr | CH | CH | CCCH$_2$CH$_3$ | CH |
| CH | CCH$_3$ | CH | CH | CBr | CH | CH | CNO$_2$ | CH |
| CH | CCH$_3$ | CH | CH | CBr | CH | CH | N | CH |
| CH | CCCH$_2$CH$_3$ | CH | CH | CBr | CH | CH | CCCH$_2$CH$_3$ | CH |
| CH | CCCH$_2$CH$_3$ | CH | CH | CBr | CH | CH | CNO$_2$ | CH |
| CH | CCCH$_2$CH$_3$ | CH | CH | CBr | CH | CH | N | CH |
| CH | CNO$_2$ | CH | CH | CBr | CH | CH | CNO$_2$ | CH |
| CH | CNO$_2$ | CH | CH | CBr | CH | CH | N | CH |
| CH | N | CH | CH | CBr | CH | CH | N | CH |
| CH | CH | CH | CF | CH | CF | CH | CH | CH |
| CH | CH | CH | CCl | CH | CF | CH | CH | CH |
| CH | CH | CH | CBr | CH | CF | CH | CH | CH |
| CH | CH | CH | CI | CH | CF | CH | CH | CH |
| CH | CH | CH | COCH$_3$ | CH | CF | CH | CH | CH |
| CH | CH | CH | CCF$_3$ | CH | CF | CH | CH | CH |
| CH | CH | CH | COCF$_2$H | CH | CF | CH | CH | CH |
| CH | CH | CH | COCF$_3$ | CH | CF | CH | CH | CH |
| CH | CH | CH | CCH$_3$ | CH | CF | CH | CH | CH |
| CH | CH | CH | CCCH$_2$CH$_3$ | CH | CF | CH | CH | CH |
| CH | CH | CH | CNO$_2$ | CH | CF | CH | CH | CH |
| CH | CH | CH | N | CH | CF | CH | CH | CH |
| CH | CH | CH | CCl | CH | CCl | CH | CH | CH |
| CH | CH | CH | CBr | CH | CCl | CH | CH | CH |
| CH | CH | CH | CI | CH | CCl | CH | CH | CH |
| CH | CH | CH | COCH$_3$ | CH | CCl | CH | CH | CH |
| CH | CH | CH | CCF$_3$ | CH | CCl | CH | CH | CH |
| CH | CH | CH | COCF$_2$H | CH | CCl | CH | CH | CH |
| CH | CH | CH | COCF$_3$ | CH | CCl | CH | CH | CH |
| CH | CH | CH | CCH$_3$ | CH | CCl | CH | CH | CH |

TABLE 1-continued

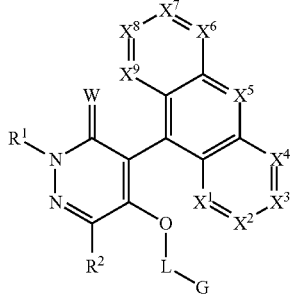

| X¹ | X² | X³ | X⁴ | X⁵ | X⁶ | X⁷ | X⁸ | X⁹ |
|---|---|---|---|---|---|---|---|---|
| CH | CH | CH | CCCH$_2$CH$_3$ | CH | CCl | CH | CH | CH |
| CH | CH | CH | CNO$_2$ | CH | CCl | CH | CH | CH |
| CH | CH | CH | N | CH | CCl | CH | CH | CH |
| CH | CH | CH | CBr | CH | CBr | CH | CH | CH |
| CH | CH | CH | CI | CH | CBr | CH | CH | CH |
| CH | CH | CH | COCH$_3$ | CH | CBr | CH | CH | CH |
| CH | CH | CH | CCF$_3$ | CH | CBr | CH | CH | CH |
| CH | CH | CH | COCF$_2$H | CH | CBr | CH | CH | CH |
| CH | CH | CH | COCF$_3$ | CH | CBr | CH | CH | CH |
| CH | CH | CH | CCH$_3$ | CH | CBr | CH | CH | CH |
| CH | CH | CH | CCCH$_2$CH$_3$ | CH | CBr | CH | CH | CH |
| CH | CH | CH | CNO$_2$ | CH | CBr | CH | CH | CH |
| CH | CH | CH | N | CH | CBr | CH | CH | CH |
| CH | CH | CH | CI | CH | CI | CH | CH | CH |
| CH | CH | CH | COCH$_3$ | CH | CI | CH | CH | CH |
| CH | CH | CH | CCF$_3$ | CH | CI | CH | CH | CH |
| CH | CH | CH | COCF$_2$H | CH | CI | CH | CH | CH |
| CH | CH | CH | COCF$_3$ | CH | CI | CH | CH | CH |
| CH | CH | CH | CCH$_3$ | CH | CI | CH | CH | CH |
| CH | CH | CH | CCCH$_2$CH$_3$ | CH | CI | CH | CH | CH |
| CH | CH | CH | CNO$_2$ | CH | CI | CH | CH | CH |
| CH | CH | CH | N | CH | CI | CH | CH | CH |
| CH | CH | CH | COCH$_3$ | CH | COCH$_3$ | CH | CH | CH |
| CH | CH | CH | CCF$_3$ | CH | COCH$_3$ | CH | CH | CH |
| CH | CH | CH | COCF$_2$H | CH | COCH$_3$ | CH | CH | CH |
| CH | CH | CH | COCF$_3$ | CH | COCH$_3$ | CH | CH | CH |
| CH | CH | CH | CCH$_3$ | CH | COCH$_3$ | CH | CH | CH |
| CH | CH | CH | CCCH$_2$CH$_3$ | CH | COCH$_3$ | CH | CH | CH |
| CH | CH | CH | CNO$_2$ | CH | COCH$_3$ | CH | CH | CH |
| CH | CH | CH | N | CH | COCH$_3$ | CH | CH | CH |
| CH | CH | CH | CCF$_3$ | CH | CCF$_3$ | CH | CH | CH |
| CH | CH | CH | COCF$_2$H | CH | CCF$_3$ | CH | CH | CH |
| CH | CH | CH | COCF$_3$ | CH | CCF$_3$ | CH | CH | CH |
| CH | CH | CH | CCH$_3$ | CH | CCF$_3$ | CH | CH | CH |
| CH | CH | CH | CCCH$_2$CH$_3$ | CH | CCF$_3$ | CH | CH | CH |
| CH | CH | CH | CNO$_2$ | CH | CCF$_3$ | CH | CH | CH |
| CH | CH | CH | N | CH | CCF$_3$ | CH | CH | CH |
| CH | CH | CH | COCF$_2$H | CH | COCF$_2$H | CH | CH | CH |
| CH | CH | CH | COCF$_3$ | CH | COCF$_2$H | CH | CH | CH |
| CH | CH | CH | CCH$_3$ | CH | COCF$_2$H | CH | CH | CH |
| CH | CH | CH | CCCH$_2$CH$_3$ | CH | COCF$_2$H | CH | CH | CH |
| CH | CH | CH | CNO$_2$ | CH | COCF$_2$H | CH | CH | CH |
| CH | CH | CH | N | CH | COCF$_2$H | CH | CH | CH |
| CH | CH | CH | COCF$_3$ | CH | COCF$_3$ | CH | CH | CH |
| CH | CH | CH | CCH$_3$ | CH | COCF$_3$ | CH | CH | CH |
| CH | CH | CH | CCCH$_2$CH$_3$ | CH | COCF$_3$ | CH | CH | CH |
| CH | CH | CH | CNO$_2$ | CH | COCF$_3$ | CH | CH | CH |
| CH | CH | CH | N | CH | COCF$_3$ | CH | CH | CH |
| CH | CH | CH | CCH$_3$ | CH | CCH$_3$ | CH | CH | CH |
| CH | CH | CH | CCCH$_2$CH$_3$ | CH | CCH$_3$ | CH | CH | CH |
| CH | CH | CH | CNO$_2$ | CH | CCH$_3$ | CH | CH | CH |
| CH | CH | CH | N | CH | CCH$_3$ | CH | CH | CH |
| CH | CH | CH | CCCH$_2$CH$_3$ | CH | CCCH$_2$CH$_3$ | CH | CH | CH |
| CH | CH | CH | CNO$_2$ | CH | CCCH$_2$CH$_3$ | CH | CH | CH |
| CH | CH | CH | N | CH | CCCH$_2$CH$_3$ | CH | CH | CH |
| CH | CH | CH | CNO$_2$ | CH | CNO$_2$ | CH | CH | CH |
| CH | CH | CH | N | CH | CNO$_2$ | CH | CH | CH |
| CH | CH | CH | N | CH | N | CH | CH | CH |
| CH | CF | CH | CH | CH | CF | CH | CH | CH |
| CH | CCl | CH | CH | CH | CF | CH | CH | CH |
| CH | CBr | CH | CH | CH | CF | CH | CH | CH |
| CH | CI | CH | CH | CH | CF | CH | CH | CH |
| CH | COCH$_3$ | CH | CH | CH | CF | CH | CH | CH |

TABLE 1-continued

| X¹ | X² | X³ | X⁴ | X⁵ | X⁶ | X⁷ | X⁸ | X⁹ |
|---|---|---|---|---|---|---|---|---|
| CH | CCF₃ | CH | CH | CH | CF | CH | CH | CH |
| CH | COCF₂H | CH | CH | CH | CF | CH | CH | CH |
| CH | COCF₃ | CH | CH | CH | CF | CH | CH | CH |
| CH | CCH₃ | CH | CH | CH | CF | CH | CH | CH |
| CH | CCCH₂CH₃ | CH | CH | CH | CF | CH | CH | CH |
| CH | CNO₂ | CH | CH | CH | CF | CH | CH | CH |
| CH | N | CH | CH | CH | CF | CH | CH | CH |
| CH | CCl | CH | CH | CH | CCl | CH | CH | CH |
| CH | CBr | CH | CH | CH | CCl | CH | CH | CH |
| CH | CI | CH | CH | CH | CCl | CH | CH | CH |
| CH | COCH₃ | CH | CH | CH | CCl | CH | CH | CH |
| CH | CCF₃ | CH | CH | CH | CCl | CH | CH | CH |
| CH | COCF₂H | CH | CH | CH | CCl | CH | CH | CH |
| CH | COCF₃ | CH | CH | CH | CCl | CH | CH | CH |
| CH | CCH₃ | CH | CH | CH | CCl | CH | CH | CH |
| CH | CCCH₂CH₃ | CH | CH | CH | CCl | CH | CH | CH |
| CH | CNO₂ | CH | CH | CH | CCl | CH | CH | CH |
| CH | N | CH | CH | CH | CCl | CH | CH | CH |
| CH | CBr | CH | CH | CH | CBr | CH | CH | CH |
| CH | CI | CH | CH | CH | CBr | CH | CH | CH |
| CH | COCH₃ | CH | CH | CH | CBr | CH | CH | CH |
| CH | CCF₃ | CH | CH | CH | CBr | CH | CH | CH |
| CH | COCF₂H | CH | CH | CH | CBr | CH | CH | CH |
| CH | COCF₃ | CH | CH | CH | CBr | CH | CH | CH |
| CH | CCH₃ | CH | CH | CH | CBr | CH | CH | CH |
| CH | CCCH₂CH₃ | CH | CH | CH | CBr | CH | CH | CH |
| CH | CNO₂ | CH | CH | CH | CBr | CH | CH | CH |
| CH | N | CH | CH | CH | CBr | CH | CH | CH |
| CH | CI | CH | CH | CH | CI | CH | CH | CH |
| CH | COCH₃ | CH | CH | CH | CI | CH | CH | CH |
| CH | CCF₃ | CH | CH | CH | CI | CH | CH | CH |
| CH | COCF₂H | CH | CH | CH | CI | CH | CH | CH |
| CH | COCF₃ | CH | CH | CH | CI | CH | CH | CH |
| CH | CCH₃ | CH | CH | CH | CI | CH | CH | CH |
| CH | CCCH₂CH₃ | CH | CH | CH | CI | CH | CH | CH |
| CH | CNO₂ | CH | CH | CH | CI | CH | CH | CH |
| CH | N | CH | CH | CH | CI | CH | CH | CH |
| CH | COCH₃ | CH | CH | CH | COCH₃ | CH | CH | CH |
| CH | CCF₃ | CH | CH | CH | COCH₃ | CH | CH | CH |
| CH | COCF₂H | CH | CH | CH | COCH₃ | CH | CH | CH |
| CH | COCF₃ | CH | CH | CH | COCH₃ | CH | CH | CH |
| CH | CCH₃ | CH | CH | CH | COCH₃ | CH | CH | CH |
| CH | CCCH₂CH₃ | CH | CH | CH | COCH₃ | CH | CH | CH |
| CH | CNO₂ | CH | CH | CH | COCH₃ | CH | CH | CH |
| CH | N | CH | CH | CH | COCH₃ | CH | CH | CH |
| CH | CCF₃ | CH | CH | CH | CCF₃ | CH | CH | CH |
| CH | COCF₂H | CH | CH | CH | CCF₃ | CH | CH | CH |
| CH | COCF₃ | CH | CH | CH | CCF₃ | CH | CH | CH |
| CH | CCH₃ | CH | CH | CH | CCF₃ | CH | CH | CH |
| CH | CCCH₂CH₃ | CH | CH | CH | CCF₃ | CH | CH | CH |
| CH | CNO₂ | CH | CH | CH | CCF₃ | CH | CH | CH |
| CH | N | CH | CH | CH | CCF₃ | CH | CH | CH |
| CH | COCF₂H | CH | CH | CH | COCF₂H | CH | CH | CH |
| CH | COCF₃ | CH | CH | CH | COCF₂H | CH | CH | CH |
| CH | CCH₃ | CH | CH | CH | COCF₂H | CH | CH | CH |
| CH | CCCH₂CH₃ | CH | CH | CH | COCF₂H | CH | CH | CH |
| CH | CNO₂ | CH | CH | CH | COCF₂H | CH | CH | CH |
| CH | N | CH | CH | CH | COCF₂H | CH | CH | CH |
| CH | COCF₃ | CH | CH | CH | COCF₃ | CH | CH | CH |
| CH | CCH₃ | CH | CH | CH | COCF₃ | CH | CH | CH |
| CH | CCCH₂CH₃ | CH | CH | CH | COCF₃ | CH | CH | CH |
| CH | CNO₂ | CH | CH | CH | COCF₃ | CH | CH | CH |
| CH | N | CH | CH | CH | COCF₃ | CH | CH | CH |

TABLE 1-continued

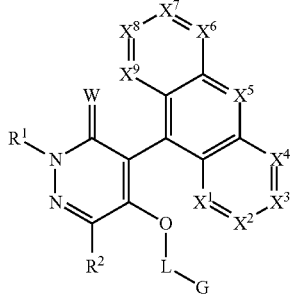

| $X^1$ | $X^2$ | $X^3$ | $X^4$ | $X^5$ | $X^6$ | $X^7$ | $X^8$ | $X^9$ |
|---|---|---|---|---|---|---|---|---|
| CH | CCH$_3$ | CH | CH | CH | CCH$_3$ | CH | CH | CH |
| CH | CCH$_2$CH$_3$ | CH | CH | CH | CCH$_3$ | CH | CH | CH |
| CH | CNO$_2$ | CH | CH | CH | CCH$_3$ | CH | CH | CH |
| CH | N | CH | CH | CH | CCH$_3$ | CH | CH | CH |
| CH | CCCH$_2$CH$_3$ | CH | CH | CH | CCCH$_2$CH$_3$ | CH | CH | CH |
| CH | CNO$_2$ | CH | CH | CH | CCCH$_2$CH$_3$ | CH | CH | CH |
| CH | N | CH | CH | CH | CCCH$_2$CH$_3$ | CH | CH | CH |
| CH | CNO$_2$ | CH | CH | CH | CNO$_2$ | CH | CH | CH |
| CH | N | CH | CH | CH | CNO$_2$ | CH | CH | CH |
| CH | N | CH | CH | CH | N | CH | CH | CH |
| CH | CF | CH | CF | CH | CH | CH | CH | CH |
| CH | CCl | CH | CF | CH | CH | CH | CH | CH |
| CH | CBr | CH | CF | CH | CH | CH | CH | CH |
| CH | CI | CH | CF | CH | CH | CH | CH | CH |
| CH | COCH$_3$ | CH | CF | CH | CH | CH | CH | CH |
| CH | CCF$_3$ | CH | CF | CH | CH | CH | CH | CH |
| CH | COCF$_2$H | CH | CF | CH | CH | CH | CH | CH |
| CH | COCF$_3$ | CH | CF | CH | CH | CH | CH | CH |
| CH | CCH$_3$ | CH | CF | CH | CH | CH | CH | CH |
| CH | CCCH$_2$CH$_3$ | CH | CF | CH | CH | CH | CH | CH |
| CH | CNO$_2$ | CH | CF | CH | CH | CH | CH | CH |
| CH | N | CH | CF | CH | CH | CH | CH | CH |
| CH | CF | CH | CCl | CH | CH | CH | CH | CH |
| CH | CCl | CH | CCl | CH | CH | CH | CH | CH |
| CH | CBr | CH | CCl | CH | CH | CH | CH | CH |
| CH | CI | CH | CCl | CH | CH | CH | CH | CH |
| CH | COCH$_3$ | CH | CCl | CH | CH | CH | CH | CH |
| CH | CCF$_3$ | CH | CCl | CH | CH | CH | CH | CH |
| CH | COCF$_2$H | CH | CCl | CH | CH | CH | CH | CH |
| CH | COCF$_3$ | CH | CCl | CH | CH | CH | CH | CH |
| CH | CCH$_3$ | CH | CCl | CH | CH | CH | CH | CH |
| CH | CCCH$_2$CH$_3$ | CH | CCl | CH | CH | CH | CH | CH |
| CH | CNO$_2$ | CH | CCl | CH | CH | CH | CH | CH |
| CH | N | CH | CCl | CH | CH | CH | CH | CH |
| CH | CF | CH | COCH$_3$ | CH | CH | CH | CH | CH |
| CH | CCl | CH | COCH$_3$ | CH | CH | CH | CH | CH |
| CH | CBr | CH | COCH$_3$ | CH | CH | CH | CH | CH |
| CH | CI | CH | COCH$_3$ | CH | CH | CH | CH | CH |
| CH | COCH$_3$ | CH | COCH$_3$ | CH | CH | CH | CH | CH |
| CH | CCF$_3$ | CH | COCH$_3$ | CH | CH | CH | CH | CH |
| CH | COCF$_2$H | CH | COCH$_3$ | CH | CH | CH | CH | CH |
| CH | COCF$_3$ | CH | COCH$_3$ | CH | CH | CH | CH | CH |
| CH | CCH$_3$ | CH | COCH$_3$ | CH | CH | CH | CH | CH |
| CH | CCCH$_2$CH$_3$ | CH | COCH$_3$ | CH | CH | CH | CH | CH |
| CH | CNO$_2$ | CH | COCH$_3$ | CH | CH | CH | CH | CH |
| CH | N | CH | COCH$_3$ | CH | CH | CH | CH | CH |
| CH | CF | CH | CCH$_3$ | CH | CH | CH | CH | CH |
| CH | CCl | CH | CCH$_3$ | CH | CH | CH | CH | CH |
| CH | CBr | CH | CCH$_3$ | CH | CH | CH | CH | CH |
| CH | CI | CH | CCH$_3$ | CH | CH | CH | CH | CH |
| CH | COCH$_3$ | CH | CCH$_3$ | CH | CH | CH | CH | CH |
| CH | CCF$_3$ | CH | CCH$_3$ | CH | CH | CH | CH | CH |
| CH | COCF$_2$H | CH | CCH$_3$ | CH | CH | CH | CH | CH |
| CH | COCF$_3$ | CH | CCH$_3$ | CH | CH | CH | CH | CH |
| CH | CCH$_3$ | CH | CCH$_3$ | CH | CH | CH | CH | CH |
| CH | CCCH$_2$CH$_3$ | CH | CCH$_3$ | CH | CH | CH | CH | CH |
| CH | CNO$_2$ | CH | CCH$_3$ | CH | CH | CH | CH | CH |
| CH | N | CH | CCH$_3$ | CH | CH | CH | CH | CH |
| CH | CF | CH | CCF$_3$ | CH | CH | CH | CH | CH |
| CH | CCl | CH | CCF$_3$ | CH | CH | CH | CH | CH |
| CH | CBr | CH | CCF$_3$ | CH | CH | CH | CH | CH |
| CH | CI | CH | CCF$_3$ | CH | CH | CH | CH | CH |
| CH | COCH$_3$ | CH | CCF$_3$ | CH | CH | CH | CH | CH |

TABLE 1-continued

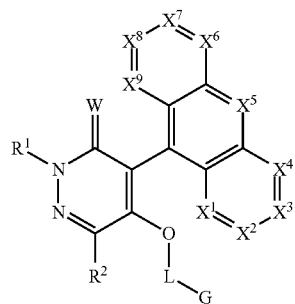

| X¹ | X² | X³ | X⁴ | X⁵ | X⁶ | X⁷ | X⁸ | X⁹ |
|---|---|---|---|---|---|---|---|---|
| CH | CCF₃ | CH | CCF₃ | CH | CH | CH | CH | CH |
| CH | COCF₂H | CH | CCF₃ | CH | CH | CH | CH | CH |
| CH | COCF₃ | CH | CCF₃ | CH | CH | CH | CH | CH |
| CH | CCH₃ | CH | CCF₃ | CH | CH | CH | CH | CH |
| CH | CCCH₂CH₃ | CH | CCF₃ | CH | CH | CH | CH | CH |
| CH | CNO₂ | CH | CCF₃ | CH | CH | CH | CH | CH |
| CH | N | CH | CCF₃ | CH | CH | CH | CH | CH |
| CF | CH | CH | CH | CH | CH | CH | CH | CH |
| CH | CH | CF | CH | CH | CH | CH | CH | CH |
| CCl | CH | CH | CH | CH | CH | CH | CH | CH |
| CH | CH | C—Cl | CH | CH | CH | CH | CH | CH |
| CCH₃ | CH | CH | CH | CH | CH | CH | CH | CH |
| CH | CH | CCH₃ | CH | CH | CH | CH | CH | CH |
| CF | CCH₃ | CH | CH | CH | CH | CH | CH | CH |
| CH | CCH₃ | CF | CH | CH | CH | CH | CH | CH |
| CCl | CCH₃ | CH | CH | CH | CH | CH | CH | CH |
| CH | CCH₃ | CCl | CH | CH | CH | CH | CH | CH |
| CBr | CCH₃ | CH | CH | CH | CH | CH | CH | CH |
| CCl | CCH₃ | CH | CH | CH | CH | CH | CCH₃ | CH |
| CCl | CCH₃ | CH | CH | CH | CH | CH | CCl | CH |
| CCl | CCH₃ | CH | CH | CH | CH | CH | CF | CH |
| CCl | CCl | CH | CH | CH | CH | CH | CCH₃ | CH |
| CCl | CF | CH | CH | CH | CH | CH | CCH₃ | CH |
| CBr | CCH₃ | CH | CH | CH | CH | CH | CCH₃ | CH |
| CBr | CCH₃ | CH | CH | CH | CH | CH | CCl | CH |
| CBr | CCH₃ | CH | CH | CH | CH | CH | CF | CH |
| CBr | CCl | CH | CH | CH | CH | CH | CCH₃ | CH |
| CBr | CF | CH | CH | CH | CH | CH | CCH₃ | CH |
| CF | CH | CH | CH | CCl | CH | CH | CH | CH |
| CH | CH | CF | CH | CCl | CH | CH | CH | CH |
| CCl | CH | CH | CH | CCl | CH | CH | CH | CH |
| CH | CH | C—Cl | CH | CCl | CH | CH | CH | CH |
| CCH₃ | CH | CH | CH | CCl | CH | CH | CH | CH |
| CH | CH | CCH₃ | CH | CCl | CH | CH | CH | CH |
| CF | CCH₃ | CH | CH | CCl | CH | CH | CH | CH |
| CH | CCH₃ | CF | CH | CCl | CH | CH | CH | CH |
| CCl | CCH₃ | CH | CH | CCl | CH | CH | CH | CH |
| CH | CCH₃ | CCl | CH | CCl | CH | CH | CH | CH |
| CBr | CCH₃ | CH | CH | CCl | CH | CH | CH | CH |
| CCl | CCH₃ | CH | CH | CCl | CH | CH | CCH₃ | CH |
| CCl | CCH₃ | CH | CH | CCl | CH | CH | CCl | CH |
| CCl | CCH₃ | CH | CH | CCl | CH | CH | CF | CH |
| CCl | CCl | CH | CH | CCl | CH | CH | CCH₃ | CH |
| CCl | CF | CH | CH | CCl | CH | CH | CCH₃ | CH |
| CBr | CCH₃ | CH | CH | CCl | CH | CH | CCH₃ | CH |
| CBr | CCH₃ | CH | CH | CCl | CH | CH | CCl | CH |
| CBr | CCH₃ | CH | CH | CCl | CH | CH | CF | CH |
| CBr | CCl | CH | CH | CCl | CH | CH | CCH₃ | CH |
| CBr | CF | CH | CH | CCl | CH | CH | CCH₃ | CH |
| CF | CH | CH | CH | CBr | CH | CH | CH | CH |
| CH | CH | CF | CH | CBr | CH | CH | CH | CH |
| CCl | CH | CH | CH | CBr | CH | CH | CH | CH |
| CH | CH | C—Cl | CH | CBr | CH | CH | CH | CH |
| CCH₃ | CH | CH | CH | CBr | CH | CH | CH | CH |
| CH | CH | CCH₃ | CH | CBr | CH | CH | CH | CH |
| CF | CCH₃ | CH | CH | CBr | CH | CH | CH | CH |
| CH | CCH₃ | CF | CH | CBr | CH | CH | CH | CH |
| CCl | CCH₃ | CH | CH | CBr | CH | CH | CH | CH |
| CH | CCH₃ | CCl | CH | CBr | CH | CH | CH | CH |
| CBr | CCH₃ | CH | CH | CBr | CH | CH | CH | CH |
| CCl | CCH₃ | CH | CH | CBr | CH | CH | CCH₃ | CH |
| CCl | CCH₃ | CH | CH | CBr | CH | CH | CCl | CH |
| CCl | CCH₃ | CH | CH | CBr | CH | CH | CF | CH |

TABLE 1-continued

| $X^1$ | $X^2$ | $X^3$ | $X^4$ | $X^5$ | $X^6$ | $X^7$ | $X^8$ | $X^9$ |
|---|---|---|---|---|---|---|---|---|
| CCl | CCl | CH | CH | CBr | CH | CH | CCH$_3$ | CH |
| CCl | CF | CH | CH | CBr | CH | CH | CCH$_3$ | CH |
| CBr | CCH$_3$ | CH | CH | CBr | CH | CH | CCH$_3$ | CH |
| CBr | CCH$_3$ | CH | CH | CBr | CH | CH | CCl | CH |
| CBr | CCH$_3$ | CH | CH | CBr | CH | CH | CF | CH |
| CBr | CCl | CH | CH | CBr | CH | CH | CCH$_3$ | CH |
| CBr | CF | CH | CH | CBr | CH | CH | CCH$_3$ | CH |

W=O, $R^1$=Me, $R^2$=Me, L-G=H and the remaining variables are defined below

This disclosure also includes TABLES 2 through 48 wherein the Header Row Phrase in TABLE 1 (i.e. "W=O, $R^1$=Me, $R^2$=Me, L-G=H") is replaced with the Header Row Phrase listed in the respective TABLE, and the remaining variables are as defined in TABLE 1.

| TABLE | Header Row Phrase |
|---|---|
| 2 | W = O, $R^1$ = Me, $R^2$ = Cl, L-G = H |
| 3 | W = O, $R^1$ = Me, $R^2$ = BR, L-G = H |
| 4 | W = O, $R^1$ = Me, $R^2$ = OCH$_3$, L-G = H |
| 5 | W = O, $R^1$ = Et, $R^2$ = CH$_3$, L-G = H |
| 6 | W = O, $R^1$ = Et, $R^2$ = Cl, L-G = H |
| 7 | W = O, $R^1$ = Et, $R^2$ = Br, L-G = H |
| 8 | W = O, $R^1$ = Et, $R^2$ = OCH$_3$, L-G = H |
| 9 | W = O, $R^1$ = CH$_2$CH$_2$OCH$_3$, $R^2$ = CH$_3$, L-G = H |
| 10 | W = O, $R^1$ = CH$_2$CH$_2$OCH$_3$, $R^2$ = Cl, L-G = H |
| 11 | W = O, $R^1$ = CH$_2$CH$_2$OCH$_3$, $R^2$ = Br, L-G = H |
| 12 | W = O, $R^1$ = CH$_2$CH$_2$OCH$_3$, $R^2$ = OCH$_3$, L-G = H |
| 13 | W = O, $R^1$ = Me, $R^2$ = CH$_3$, L-G = C(O)CH$_3$ |
| 14 | W = O, $R^1$ = Me, $R^2$ = Cl, L-G = C(O)CH$_3$ |
| 15 | W = O, $R^1$ = Me, $R^2$ = Br, L-G = C(O)CH$_3$ |
| 16 | W = O, $R^1$ = Me, $R^2$ = OCH$_3$, L-G = C(O)CH$_3$ |
| 17 | W = O, $R^1$ = Et, $R^2$ = CH$_3$, L-G = C(O)CH$_3$ |
| 18 | W = O, $R^1$ = Et, $R^2$ = Cl, L-G = C(O)CH$_3$ |
| 19 | W = O, $R^1$ = Et, $R^2$ = Br, L-G = C(O)CH$_3$ |
| 20 | W = O, $R^1$ = Et, $R^2$ = OCH$_3$, L-G = C(O)CH$_3$ |
| 21 | W = O, $R^1$ = CH$_2$CH$_2$OCH$_3$, $R^2$ = CH$_3$, L-G = C(O)CH$_3$ |
| 22 | W = O, $R^1$ = CH$_2$CH$_2$OCH$_3$, $R^2$ = Cl, L-G = C(O)CH$_3$ |
| 23 | W = O, $R^1$ = CH$_2$CH$_2$OCH$_3$, $R^2$ = Br, L-G = C(O)CH$_3$ |
| 24 | W = O, $R^1$ = CH$_2$CH$_2$OCH$_3$, $R^2$ = OCH$_3$, L-G = C(O)CH$_3$ |
| 25 | W = O, $R^1$ = Me, $R^2$ = CH$_3$, L-G = C(O)CH$_2$CH$_3$ |
| 26 | W = O, $R^1$ = Me, $R^2$ = Cl, L-G = C(O)CH$_2$CH$_3$ |
| 27 | W = O, $R^1$ = Me, $R^2$ = Br, L-G = C(O)CH$_2$CH$_3$ |
| 28 | W = O, $R^1$ = Me, $R^2$ = OCH$_3$, L-G = C(O)CH$_2$CH$_3$ |
| 29 | W = O, $R^1$ = Et, $R^2$ = CH$_3$, L-G = C(O)CH$_2$CH$_3$ |
| 30 | W = O, $R^1$ = Et, $R^2$ = Cl L-G = C(O)CH$_2$CH$_3$ |
| 31 | W = O, $R^1$ = Et, $R^2$ = Br, L-G = C(O)CH$_2$CH$_3$ |
| 32 | W = O, $R^1$ = Et, $R^2$ = OCH$_3$, L-G = C(O)CH$_2$CH$_3$ |
| 33 | W = O, $R^1$ = CH$_2$CH$^2$OCH$_3$, $R^2$ = CH$_3$, L-G = C(O)CH$_2$CH$_3$ |
| 34 | W = O, $R^1$ = CH$_2$CH$_2$OCH$_3$, $R^2$ = Cl, L-G = C(O)CH$_2$CH$_3$ |
| 35 | W = O, $R^1$ = CH$_2$CH$_2$OCH$_3$, $R^2$ = Br, L-G = C(O)CH$_2$CH$_3$ |
| 36 | W = O, $R^1$ = CH$_2$CH$_2$OCH$_3$, $R^2$ = OCH$_3$, L-G = C(O)CH$_2$CH$_3$ |
| 37 | W = O, $R^1$ = Me, $R^2$ = CH$_3$, L-G = C(O)OCH$_3$ |
| 38 | W = O, $R^1$ = Me, $R^2$ = Cl, L-G = C(O)OCH$_3$ |
| 39 | W = O, $R^1$ = Me, $R^2$ = Br, L-G = C(O)OCH$_3$ |
| 40 | W = O, $R^1$ = Me, $R^2$ = OCH$_3$, L-G = C(O)OCH$_3$ |
| 41 | W = O, $R^1$ = Et, $R^2$ = CH$_3$, L-G = C(O)OCH$_3$ |
| 42 | W = O, $R^1$ = Et, $R^2$ = Cl, L-G = C(O)OCH$_3$ |
| 43 | W = O, $R^1$ = Et, $R^2$ = Br, L-G = C(O)OCH$_3$ |
| 44 | W = O, $R^1$ = Et, $R^2$ = OCH$_3$, L-G = C(O)OCH$_3$ |
| 45 | W = O, $R^1$ = CH$_2$CH$_2$OCH$_3$, $R^2$ = CH$_3$, L-G = C(O)OCH$_3$ |
| 46 | W = O, $R^1$ = CH$_2$CH$_2$OCH$_3$, $R^2$ = Cl, L-G = C(O)OCH$_3$ |
| 47 | W = O, $R^1$ = CH$_2$CH$_2$OCH$_3$, $R^2$ = Br, L-G = C(O)OCH$_3$ |
| 48 | W = O, $R^1$ = CH$_2$CH$_2$OCH$_3$, $R^2$ = OCH$_3$, L-G = C(O)OCH$_3$ |

TABLE 49

W=O, $R^1$=CH$_3$, $R^2$=CH$_3$, L—G=H and the remaining variables are defined below

| $X^2$ | $X^3$ | $X^4$ | $X^5$ | $X^6$ | $X^7$ | $X^8$ | $X^9$ | $X^{10}$ |
|---|---|---|---|---|---|---|---|---|
| CH | CH | CH | CH | CH | CH | CH | CH | CH |
| CF | CH | CH | CH | CH | CH | CH | CH | CH |
| CCl | CH | CH | CH | CH | CH | CH | CH | CH |
| CCH$_3$ | CH | CH | CH | CH | CH | CH | CH | CH |
| CH | CH | CCl | CH | CH | CH | CH | CH | CH |
| CF | CH | CCl | CH | CH | CH | CH | CH | CH |
| CCl | CH | CCl | CH | CH | CH | CH | CH | CH |
| CCH$_3$ | CH | CCl | CH | CH | CH | CH | CH | CH |
| CH | CH | CBr | CH | CH | CH | CH | CH | CH |
| CF | CH | CBr | CH | CH | CH | CH | CH | CH |
| CCl | CH | CBr | CH | CH | CH | CH | CH | CH |
| CCH$_3$ | CH | CBr | CH | CH | CH | CH | CH | CH |
| CCH$_3$ | CCH$_3$ | CH | CH | CH | CH | CH | CH | CH |
| CCH$_3$ | CH | CCH$_3$ | CH | CH | CH | CH | CH | CH |
| CCH$_3$ | CH | CH | CCl | CH | CH | CH | CH | CH |
| CCH$_3$ | CH | CH | CBr | CH | CH | CH | CH | CH |

TABLE 49-continued

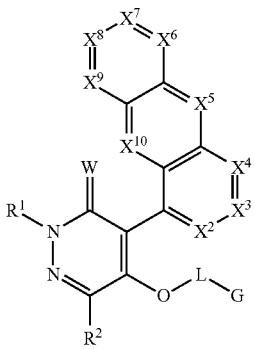

W=O, R¹=CH₃, R²=CH₃, L—G=H and the remaining variables are defined below

| X² | X³ | X⁴ | X⁵ | X⁶ | X⁷ | X⁸ | X⁹ | X¹⁰ |
|---|---|---|---|---|---|---|---|---|
| CCH₃ | CH | CH | CH | CCl | CH | CH | CH | CH |
| CCH₃ | CH | CH | CH | CH | CBr | CH | CH | CH |
| CCH₃ | CH | CH | CH | CH | CCl | CH | CH | CH |
| CCH₃ | CH | CH | CH | CH | CH | CBr | CH | CH |
| CCH₃ | CH | CH | CH | CH | CH | CCl | CH | CH |
| CCH₃ | CH | CH | CH | CH | CH | CH | CBr | CH |
| CCH₃ | CH | CH | CH | CH | CH | CH | CCl | CH |
| CCH₃ | CH | CH | CH | CH | CH | CH | CH | CBr |
| CCH₃ | CH | CH | CH | CH | CH | CH | CH | CCl |

This disclosure also includes TABLES 50 through 56 wherein the specific variable listed in each TABLE replaces the corresponding variable in the Header Row Phrase of TABLE 49. For example, in TABLE 50, the Header Row Phrase is "W=O, R¹=CH₃, R²=Cl, L-G=H" and the remaining variables are defined below".

| TABLE | Header Row Variable |
|---|---|
| 50 | R² = Cl |
| 51 | R² = OCH₃ |
| 52 | R¹ = CH₂CH₃ |
| 53 | R¹ = CH₂CH₃, R² = Cl |
| 54 | R¹ = CH₂CH₃, R² = OCH₃ |
| 55 | R¹ = CH₂CH₂OCH₃ |
| 56 | R¹ = CH₂CH₂OCH₃, R² = Cl |

TABLE 57

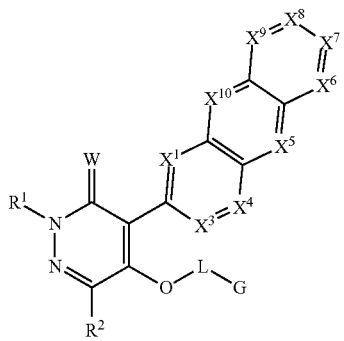

W=O, R¹=CH₃, R²=CH₃, L—G=H and the remaining variables are defined below

| X¹ | X³ | X⁴ | X⁵ | X⁶ | X⁷ | X⁸ | X⁹ | X¹⁰ |
|---|---|---|---|---|---|---|---|---|
| CH | CH | CH | CH | CH | CH | CH | CH | CH |
| CF | CH | CH | CH | CH | CH | CH | CH | CH |

TABLE 57-continued

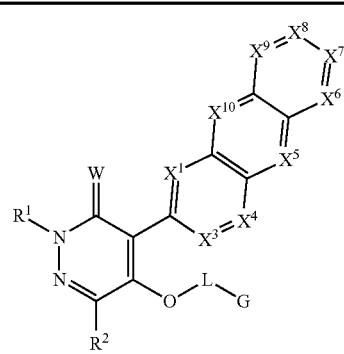

W=O, R¹=CH₃, R²=CH₃, L—G=H and the remaining variables are defined below

| X¹ | X³ | X⁴ | X⁵ | X⁶ | X⁷ | X⁸ | X⁹ | X¹⁰ |
|---|---|---|---|---|---|---|---|---|
| CCl | CH | CH | CH | CH | CH | CH | CH | CH |
| CCH₃ | CH | CH | CH | CH | CH | CH | CH | CH |
| CH | CH | CCl | CH | CH | CH | CH | CH | CH |
| CF | CH | CCl | CH | CH | CH | CH | CH | CH |
| CCl | CH | CCl | CH | CH | CH | CH | CH | CH |
| CCH₃ | CH | CCl | CH | CH | CH | CH | CH | CH |
| CH | CH | CBr | CH | CH | CH | CH | CH | CH |
| CF | CH | CBr | CH | CH | CH | CH | CH | CH |
| CCl | CH | CBr | CH | CH | CH | CH | CH | CH |
| CCH₃ | CH | CBr | CH | CH | CH | CH | CH | CH |
| CCH₃ | CCH₃ | CH | CH | CH | CH | CH | CH | CH |
| CCH₃ | CH | CCH₃ | CH | CH | CH | CH | CH | CH |
| CCH₃ | CH | CH | CCl | CH | CH | CH | CH | CH |
| CCH₃ | CH | CH | CH | CBr | CH | CH | CH | CH |
| CCH₃ | CH | CH | CH | CCl | CH | CH | CH | CH |
| CCH₃ | CH | CH | CH | CH | CBr | CH | CH | CH |
| CCH₃ | CH | CH | CH | CH | CCl | CH | CH | CH |
| CCH₃ | CH | CH | CH | CH | CH | CBr | CH | CH |
| CCH₃ | CH | CH | CH | CH | CH | CCl | CH | CH |
| CCH₃ | CH | CH | CH | CH | CH | CH | CBr | CH |
| CCH₃ | CH | CH | CH | CH | CH | CH | CCl | CH |
| CCH₃ | CH | CH | CH | CH | CH | CH | CH | CBr |
| CCH₃ | CH | CH | CH | CH | CH | CH | CH | CCl |

This disclosure also includes TABLES 58 through 65 wherein the specific variable listed in each TABLE replaces the corresponding variable in the Header Row Phrase of TABLE 57. For example, in TABLE 58, the Header Row Phrase is "W=O, R¹=CH₃, R²=Cl, L-G=H and the remaining variables are defined below".

| TABLE | Header Row Variable |
|---|---|
| 58 | R² = Cl |
| 59 | R² = OCH₃ |
| 60 | R¹ = CH₂CH₃ |
| 61 | R¹ = CH₂CH₃, R² = Cl |
| 62 | R¹ = CH₂CH₃, R² = OCH₃ |
| 63 | R¹ = CH₂CH₂OCH₃ |
| 64 | R¹ = CH₂CH₂OCH₃, R² = Cl |
| 65 | R¹ = CH₂CH₂OCH₃, R² = OCH₃ |

TABLE 66

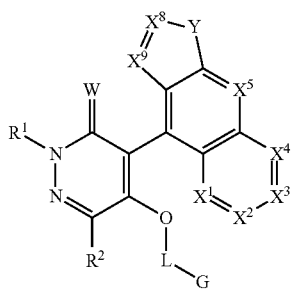

W=O, R¹=CH₃, R²=CH₃, Y=O, L—G=H and the remaining variables are defined below

| X¹ | X² | X³ | X⁴ | X⁵ | X⁸ | X⁹ |
|---|---|---|---|---|---|---|
| CH | CH | CH | CH | CH | CH | CH |
| CH | CF | CH | CH | CH | CH | CH |
| CH | CCl | CH | CH | CH | CH | CH |
| CH | CCH₃ | CH | CH | CH | CH | CH |
| CH₃ | CH | CH | CH | CH | CH | CH |
| CH₃ | CF | CH | CH | CH | CH | CH |
| CH₃ | CCl | CH | CH | CH | CH | CH |
| CH₃ | CCH₃ | CH | CH | CH | CH | CH |
| Cl | CH | CH | CH | CH | CH | CH |
| Cl | CF | CH | CH | CH | CH | CH |
| Cl | CCl | CH | CH | CH | CH | CH |
| Cl | CCH₃ | CH | CH | CH | CH | CH |
| CH | CH | CH | CH | CCl | CH | CH |
| CH | CF | CH | CH | CCl | CH | CH |
| CH | CCl | CH | CH | CCl | CH | CH |
| CH | CCH₃ | CH | CH | CCl | CH | CH |
| CH | CH | CH | CH | CBr | CH | CH |
| CH | CF | CH | CH | CBr | CH | CH |
| CH | CCl | CH | CH | CBr | CH | CH |
| CH | CCH₃ | CH | CH | CBr | CH | CH |
| CH | CCH₃ | CCH₃ | CH | CH | CH | CH |
| CH | CCH₃ | CH | CH | CCH₃ | CH | CH |
| CH | CCH₃ | CH | CCH₃ | CH | CH | CH |
| CH | CCH₃ | CH | CH | CH | CCH₃ | CH |
| CH | CCH₃ | CH | CH | CH | CBr | CH |
| CH | CCH₃ | CH | CH | CH | CCl | CH |
| CH | CCH₃ | CH | CH | CH | CH | CBr |
| CH | CCH₃ | CH | CH | CH | CH | CCl |
| CH | CCH₃ | CH | CH | CH | CH | CCH₃ |

This disclosure also includes TABLE 67 through 74 wherein the specific variable listed in each TABLE replaces the corresponding variable in the Header Row Phrase of TABLE 66. For example, the Header Row Phrase in TABLE 67 is "W=O, R¹=CH₃, R²=CH₃, Y=S, L-G=H and the remaining variable are defined below".

| TABLE | Header Row Variable |
|---|---|
| 67 | Y = S |
| 68 | Y = NCH₃ |
| 69 | R² = Cl |
| 70 | R² = Cl, Y = S |
| 71 | R² = Cl, Y = NCH₃ |
| 72 | R² = OCH₃ |
| 73 | R² = OCH₃, Y = S |
| 74 | R² = OCH₃, Y = NCH₃ |

TABLE 75

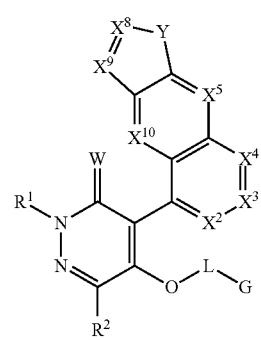

W=O, R¹=CH₃, R²=CH₃, Y=O, L—G=H and the remaining variables are defined below

| X² | X³ | X⁴ | X⁵ | X⁸ | X⁹ | X¹⁰ |
|---|---|---|---|---|---|---|
| CH | CH | CH | CH | CH | CH | CH |
| CF | CH | CH | CH | CH | CH | CH |
| CCl | CH | CH | CH | CH | CH | CH |
| CCH₃ | CH | CH | CH | CH | CH | CH |
| CH | CH | CH | CCl | CH | CH | CH |
| CF | CH | CH | CCl | CH | CH | CH |
| CCl | CH | CH | CCl | CH | CH | CH |
| CCH₃ | CH | CH | CCl | CH | CH | CH |
| CH | CH | CH | CBr | CH | CH | CH |
| CF | CH | CH | CBr | CH | CH | CH |
| CCl | CH | CH | CBr | CH | CH | CH |
| CCH₃ | CH | CH | CBr | CH | CH | CH |
| CCH₃ | CCH₃ | CH | CH | CH | CH | CH |
| CCH₃ | CH | CH | CCH₃ | CH | CH | CH |
| CCH₃ | CH | CCH₃ | CH | CH | CH | CH |
| CCH₃ | CH | CH | CH | CCH₃ | CH | CH |
| CCH₃ | CH | CH | CH | CBr | CH | CH |
| CCH₃ | CH | CH | CH | CCl | CH | CH |
| CCH₃ | CH | CH | CH | CH | CBr | CH |
| CCH₃ | CH | CH | CH | CH | CCl | CH |
| CCH₃ | CH | CH | CH | CH | CCH₃ | CH |
| CCH₃ | CH | CH | CH | CH | CH | CBr |
| CCH₃ | CH | CH | CH | CH | CH | CCl |
| CCH₃ | CH | CH | CH | CH | CH | CCH₃ |

This disclosure also includes TABLE 76 through 83 wherein the specific variable listed in each TABLE replaces the corresponding variable in the Header Row Phrase of TABLE 75. For example, the Header Row Phrase in TABLE 76 is "W=O, R¹=CH₃, R²=CH₃, Y=S, L-G=H) and the remaining variables are defined below".

| TABLE | Header Row Variable |
|---|---|
| 76 | Y = S |
| 77 | Y = NCH₃ |
| 78 | R² = Cl |
| 79 | R² = Cl, Y = S |
| 80 | R² = Cl, Y = NCH₃ |
| 81 | R² = OCH₃ |
| 82 | R² = OCH₃, Y = S |
| 83 | R² = OCH₃, Y = NCH₃ |

TABLE 84

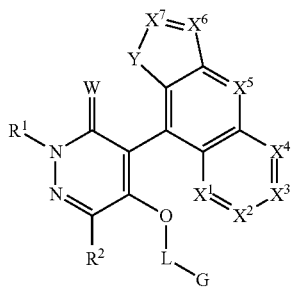

W=O, R¹=CH₃, R²=CH₃, Y=O, L—G=H and the remaining variables are defined below

| X¹ | X² | X³ | X⁴ | X⁵ | X⁶ | X⁷ |
|---|---|---|---|---|---|---|
| CH | CH | CH | CH | CH | CH | CH |
| CH | CF | CH | CH | CH | CH | CH |
| CH | CCl | CH | CH | CH | CH | CH |
| CH | CCH₃ | CH | CH | CH | CH | CH |
| CH₃ | CH | CH | CH | CH | CH | CH |
| CH₃ | CF | CH | CH | CH | CH | CH |
| CH₃ | CCl | CH | CH | CH | CH | CH |
| CH₃ | CCH₃ | CH | CH | CH | CH | CH |
| Cl | CH | CH | CH | CH | CH | CH |
| Cl | CF | CH | CH | CH | CH | CH |
| Cl | CCl | CH | CH | CH | CH | CH |
| Cl | CCH₃ | CH | CH | CH | CH | CH |
| CH | CH | CH | CH | CCl | CH | CH |
| CH | CF | CH | CH | CCl | CH | CH |
| CH | CCl | CH | CH | CCl | CH | CH |
| CH | CCH₃ | CH | CH | CCl | CH | CH |
| CH | CH | CH | CH | CBr | CH | CH |
| CH | CF | CH | CH | CBr | CH | CH |
| CH | CCl | CH | CH | CBr | CH | CH |
| CH | CCH₃ | CH | CH | CBr | CH | CH |
| CH | CCH₃ | CCH₃ | CH | CH | CH | CH |
| CH | CCH₃ | CH | CH | CCH₃ | CH | CH |
| CH | CCH₃ | CH | CCH₃ | CH | CH | CH |
| CH | CCH₃ | CH | CH | CH | CCH₃ | CH |
| CH | CCH₃ | CH | CH | CH | CBr | CH |
| CH | CCH₃ | CH | CH | CH | CCl | CH |
| CH | CCH₃ | CH | CH | CH | CH | CBr |
| CH | CCH₃ | CH | CH | CH | CH | CCl |
| CH | CCH₃ | CH | CH | CH | CH | CCH₃ |

This disclosure also includes TABLES 85 through 92 wherein the specific variable listed in each TABLE replaces the corresponding variable in the Header Row Phrase of TABLE 84. For example, the Header Row Phrase in TABLE 85 is "W=O, R¹=CH₃, R²=CH₃, Y=S, L-G=H) and the remaining variables are defined below".

| TABLE | Header Row Varaiable |
|---|---|
| 85 | Y=S |
| 86 | Y=NCH₃ |
| 87 | R²=Cl |
| 88 | R²=Cl, Y=S |
| 89 | R²=Cl, Y=NCH₃ |
| 90 | R²=OCH₃ |
| 91 | R²=OCH₃, Y=S |
| 92 | R²=OCH₃, Y=NCH₃ |

TABLE 93

W=O, R¹=CH₃, R²=CH₃, L—G=H, Y=O and the remaining variables are defined below

| X² | X³ | X⁴ | X⁵ | X⁶ | X⁷ | X¹⁰ |
|---|---|---|---|---|---|---|
| CH | CH | CH | CH | CH | CH | CH |
| CF | CH | CH | CH | CH | CH | CH |
| CCl | CH | CH | CH | CH | CH | CH |
| CCH₃ | CH | CH | CH | CH | CH | CH |
| CH | CH | CH | CCl | CH | CH | CH |
| CF | CH | CH | CCl | CH | CH | CH |
| CCl | CH | CH | CCl | CH | CH | CH |
| CCH₃ | CH | CH | CCl | CH | CH | CH |
| CH | CH | CH | CBr | CH | CH | CH |
| CF | CH | CH | CBr | CH | CH | CH |
| CCl | CH | CH | CBr | CH | CH | CH |
| CCH₃ | CH | CH | CBr | CH | CH | CH |
| CCH₃ | CCH₃ | CH | CH | CH | CH | CH |
| CCH₃ | CH | CH | CCH₃ | CH | CH | CH |
| CCH₃ | CH | CCH₃ | CH | CH | CH | CH |
| CCH₃ | CH | CH | CH | CCH₃ | CH | CH |
| CCH₃ | CH | CH | CH | CBr | CH | CH |
| CCH₃ | CH | CH | CH | CCl | CH | CH |
| CCH₃ | CH | CH | CH | CH | CBr | CH |
| CCH₃ | CH | CH | CH | CH | CCl | CH |
| CCH₃ | CH | CH | CH | CH | CCH₃ | CH |
| CCH₃ | CH | CH | CH | CH | CH | CBr |
| CCH₃ | CH | CH | CH | CH | CH | CCl |
| CCH₃ | CH | CH | CH | CH | CH | CCH₃ |

This disclosure also includes TABLES 94 through 101 wherein the specific variable listed in each TABLE replaces the corresponding variable in the Header Row Phrase of TABLE 93. For example, the Header Row Phrase in TABLE 94 is "W=O, R¹=CH₃, R²=CH₃, L-G=H, Y=S) and the remaining variables are defined below".

| TABLE | Header Row Variable |
|---|---|
| 94 | Y=S |
| 95 | Y=NCH₃ |
| 96 | R²=Cl |
| 97 | R²=Cl, Y=S |
| 98 | R²=Cl, Y=NCH₃ |
| 99 | R²=OCH₃ |
| 100 | R²=OCH₃, Y=S |
| 101 | R²=OCH₃, Y=NCH₃ |

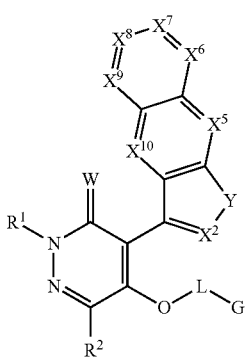

W=O, R¹=CH₃, R²=CH₃, L—G=H, Y=O and the remaining variables are defined below

| X² | X⁵ | X⁶ | X⁷ | X⁸ | X⁹ | X¹⁰ |
|---|---|---|---|---|---|---|
| CH | CH | CH | CH | CH | CH | CH |
| CF | CH | CH | CH | CH | CH | CH |
| CCl | CH | CH | CH | CH | CH | CH |
| CCH₃ | CH | CH | CH | CH | CH | CH |
| CCH₃ | CCl | CH | CH | CH | CH | CH |
| CCH₃ | CH | CBr | CH | CH | CH | CH |
| CCH₃ | CH | CCl | CH | CH | CH | CH |
| CCH₃ | CH | CH | CBr | CH | CH | CH |
| CCH₃ | CH | CH | CCl | CH | CH | CH |
| CCH₃ | CH | CH | CH | CBr | CH | CH |
| CCH₃ | CH | CH | CH | CCl | CH | CH |
| CCH₃ | CH | CH | CH | CH | CBr | CH |
| CCH₃ | CH | CH | CH | CH | CCl | CH |
| CCH₃ | CH | CH | CH | CH | CH | CBr |
| CCH₃ | CH | CH | CH | CH | CH | CCl |

This disclosure also includes TABLES 103 through 110 wherein the specific variable listed in each TABLE replaces the corresponding variable in the Header Row Phrase of TABLE 102. For example, in TABLE 103 the Header Row Phrase is "W=O, R¹=CH₃, R²=CH₃, L-G=H, Y=S) and the remaining variables are defined below".

| TABLE | Header Row Variable |
|---|---|
| 103 | Y=S |
| 104 | Y=NCH₃ |
| 105 | R²=Cl |
| 106 | R²=Cl, Y=S |
| 107 | R²=Cl, Y=NCH₃ |
| 108 | R²=OCH₃ |
| 109 | R²=OCH₃, Y=S |
| 110 | R²=OCH₃, Y=NCH₃ |

TABLE 111

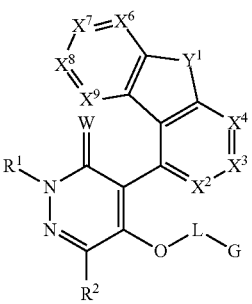

W=O, R¹=CH₃, R²=CH₃, L—G=H, Y¹=O and the remaining variables are defined below

| X² | X³ | X⁴ | X⁶ | X⁷ | X⁸ | X⁹ |
|---|---|---|---|---|---|---|
| CH | CH | CH | CH | CH | CH | CH |
| CF | CH | CH | CH | CH | CH | CH |
| CCl | CH | CH | CH | CH | CH | CH |
| CCH₃ | CH | CH | CH | CH | CH | CH |
| CH | CH | CH | CH | CH | CCl | CH |
| CF | CH | CH | CH | CH | CCl | CH |
| CCl | CH | CH | CH | CH | CCl | CH |
| CCH₃ | CH | CH | CH | CH | CCl | CH |
| CH | CH | CH | CH | CH | CBr | CH |
| CF | CH | CH | CH | CH | CBr | CH |
| CCl | CH | CH | CH | CH | CBr | CH |
| CCH₃ | CH | CH | CH | CH | CBr | CH |
| CCH₃ | CCH₃ | CH | CH | CH | CH | CH |
| CCH₃ | CH | CH | CH | CH | CCH₃ | CH |
| CCH₃ | CH | CH | CCH₃ | CH | CH | CH |
| CCH₃ | CH | CCH₃ | CH | CH | CH | CH |
| CCH₃ | CH | CBr | CH | CH | CH | CH |
| CCH₃ | CH | CCl | CH | CH | CH | CH |
| CCH₃ | CH | CH | CH | CBr | CH | CH |
| CCH₃ | CH | CH | CH | CCl | CH | CH |
| CCH₃ | CH | CH | CH | CCH₃ | CH | CH |
| CCH₃ | CH | CH | CH | CH | CH | CBr |
| CCH₃ | CH | CH | CH | CH | CH | CCl |
| CCH₃ | CH | CH | CH | CH | CH | CCH₃ |

This disclosure also includes TABLES 112 through 122 wherein the specific variable listed in each TABLE replaces the corresponding variable in the Header Row Phrase of TABLE 111. For example, the Header Row Phrase in TABLE 112 is "W=O, R¹=CH₃, R²=CH₃, L-G=H, Y¹=S and the remaining variables are defined below".

| TABLE | Header Row Variable |
|---|---|
| 112 | Y¹=S |
| 113 | Y¹=NCH₃ |
| 114 | Y¹=C(O) |
| 115 | R²=Cl |
| 116 | R²=Cl, Y¹=S |
| 117 | R²=Cl, Y¹=NCH₃ |
| 118 | R²=Cl, Y¹=C(O) |
| 119 | R²=OCH₃ |
| 120 | R²=OCH₃, Y¹=S |
| 121 | R²=OCH₃, Y¹=NCH₃ |
| 122 | R²=OCH₃, Y¹=C(O) |

TABLE 123

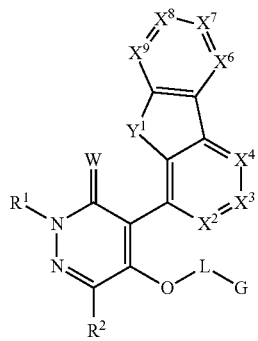

W=O, R$^1$=CH$_3$, R$^2$=CH$_3$, L—G=H, Y$^1$=O and
the remaining variables are defined below

| X$^2$ | X$^3$ | X$^4$ | X$^6$ | X$^7$ | X$^8$ | X$^9$ |
|---|---|---|---|---|---|---|
| CH | CH | CH | CH | CH | CH | CH |
| CF | CH | CH | CH | CH | CH | CH |
| CCl | CH | CH | CH | CH | CH | CH |
| CCH$_3$ | CH | CH | CH | CH | CH | CH |
| CH | CH | CH | CH | CH | CCl | CH |
| CF | CH | CH | CH | CH | CCl | CH |
| CCl | CH | CH | CH | CH | CCl | CH |
| CCH$_3$ | CH | CH | CH | CH | CCl | CH |
| CH | CH | CH | CH | CH | CBr | CH |
| CF | CH | CH | CH | CH | CBr | CH |
| CCl | CH | CH | CH | CH | CBr | CH |
| CCH$_3$ | CH | CH | CH | CH | CBr | CH |
| CCH$_3$ | CCH$_3$ | CH | CH | CH | CH | CH |
| CCH$_3$ | CH | CH | CH | CH | CCH$_3$ | CH |
| CCH$_3$ | CH | CH | CCH$_3$ | CH | CH | CH |
| CCH$_3$ | CH | CCH$_3$ | CH | CH | CH | CH |
| CCH$_3$ | CH | CBr | CH | CH | CH | CH |
| CCH$_3$ | CH | CCl | CH | CH | CH | CH |
| CCH$_3$ | CH | CH | CH | CBr | CH | CH |
| CCH$_3$ | CH | CH | CH | CCl | CH | CH |
| CCH$_3$ | CH | CH | CH | CCH$_3$ | CH | CH |
| CCH$_3$ | CH | CH | CH | CH | CH | CBr |
| CCH$_3$ | CH | CH | CH | CH | CH | CCl |
| CCH$_3$ | CH | CH | CH | CH | CH | CCH$_3$ |

This disclosure also includes TABLES 124 through 134 wherein the specific variable listed in each TABLE replaces the corresponding variable in the Header Row Phrase of TABLE 123. For example, the header Row in TABLE 124 is "W=O, R$^1$=CH$_3$, R$^2$=CH$_3$, L-G=H, Y$^1$=S and the remaining variables are defined below".

| TABLE | Header Row Variable |
|---|---|
| 124 | Y$^1$=S |
| 125 | Y$^1$=NCH$_3$ |
| 126 | Y$^1$=C(O) |
| 127 | R$^2$=Cl |
| 128 | R$^2$=Cl, Y$^1$=S |
| 129 | R$^2$=Cl, Y$^1$=NCH$_3$ |
| 130 | R$^2$=Cl, Y$^1$=C(O) |
| 131 | R$^2$=OCH$_3$ |
| 132 | R$^2$=OCH$_3$, Y$^1$=S |
| 133 | R$^2$=OCH$_3$, Y$^1$=NCH$_3$ |
| 134 | R$^2$=OCH$_3$, Y$^1$=C(O) |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents,* Chemical Publ. Co., Inc., New York, 1964; and A. S. Davidson and B. Milwidsky, *Synthetic Detergents,* Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook,* 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8th Ed., Blackwell Scientific Publications, Oxford, 1989; and *Developments in formulation technology,* PJB Publications, Richmond, UK, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
| --- | --- |
| Compound 1 | 98.5% |
| silica aerogel | 0.5% |
| synthetic amorphous fine silica | 1.0% |

Example B

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
| --- | --- |
| Compound 1 | 10.0% |
| attapulgite granules (low volatile matter, 0.71/0.30 mm; U.S.S. No. 25-50 sieves) | 90.0% |

Example D

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
| --- | --- |
| Compound 1 | 10.0% |
| polyoxyethylene sorbitol hexoleate | 20.0% |
| $C_6$-$C_{10}$ fatty acid methyl ester | 70.0% |

Example F

| Microemulsion | |
| --- | --- |
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Suspension Concentrate | |
| --- | --- |
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

| Emulsion in Water | |
| --- | --- |
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

| Oil Dispersion | |
| --- | --- |
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except that "Compound 1" is replaced with "Compound 2", "Compound 3", "Compound 4", "Compound 5", "Compound 6", "Compound 7", "Compound 8", "Compound 9" or "Compound 10".

Test results indicate that the compounds of the present invention are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation. Undesired vegetation includes at least one selected from the group consisting of grass weeds and broadleaf weeds. Undesired vegetation is selected from the group consisting of annual bluegrass, Benghal dayflower, blackgrass, black nightshade, broadleaf signalgrass, Canada thistle, cheat, common cocklebur (*Xanthium pensylvanicum*), common ragweed, corn poppies, field violet, giant foxtail, goosegrass, green foxtail, guinea grass, hairy beggarticks, herbicide-resistant black grass, horseweed, Italian rye grass, jimsonweed, Johnson grass (*Sorghum halepense*), large crabgrass, little seed canary grass, morning glory, Pennsylvania smartweed, pitted morning glory, prickly sida, quackgrass, redroot pigweed, shattercane, shepherd's purse, silky windgrass, sunflower (as weed in potato), wild buckwheat (*Polygonum convolvulus*), wild mustard (*Brassica kaber*), wild oat (*Avena fatua*), wild pointsettia, yellow foxtail, and yellow nutsedge (*Cyperus esculentus*).

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Although most typically, compounds of the invention are used to control undesired vegetation, contact of desired vegetation in the treated locus with compounds of the invention may result in super-additive or enhanced effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)methoxyl]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Preferred for better control of undesired vegetation (e.g., lower use rate such as from enhanced effects, broader spectrum of weeds controlled, or enhanced crop safety) or for preventing the development of resistant weeds are mixtures of a compound of this invention with a herbicide selected from the group consisting of atrazine, azimsulfuron, S-beflubutamid, benzisothiazolinone, carfentrazone-ethyl, chlorimuron-ethyl, chlorsulfuron-methyl, clomazone, clopyralid potassium, cloransulam-methyl, 2-[(2,4-dichlorophenyl)methyl]-4,4-dimethyl-3-isoxazolidinone, 2-[(2,5-dichlorophenyl)methyl]-4,4-dimethyl-3-isoxazolidinone, ethametsulfuron-methyl, flumetsulam, 4-(4-fluorophenyl)-6-[(2-hydroxy-6-oxo-1-cyclohexen-1-yl)carbonyl]-2-methyl-1,2,4-triazine-3,5-(2H,4H)-dione, flupyrsulfuron-methyl, fluthiacet-methyl, fomesafen, imazethapyr, lenacil, mesotrione, metribuzin, metsulfuron-methyl, pethoxamid, picloram, pyroxasulfone, quinclorac, rimsulfuron, S-metolachlor, sulfentrazone, thifensulfuron-methyl, triflusulfuron-methyl and tribenuron-methyl.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13*th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i e enhanced) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When the enhanced effects of herbicidal mixtures of active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]-benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]

sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention can also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from enhanced effects, broader spectrum of weeds controlled, or enhanced crop safety) or for preventing the development of resistant weeds are mixtures of a compound of this invention with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this invention against specific weeds. The weed control afforded by the compounds is not limited, however, to these species. See Index Table A for compound descriptions. The following abbreviations are used in the Index Table which follows: "Cmpd. No." stands for "Compound Number", "Ex." stands for "Example" and is followed by a number indicating in which example the compound is prepared. $^1$H NMR spectra are reported in ppm downfield from tetramethylsilane in DMSO-$d_6$ solution unless indicated otherwise; "s" means singlet, "d" means doublet, "t" means triplet and "m" means multiplet.

INDEX TABLE A

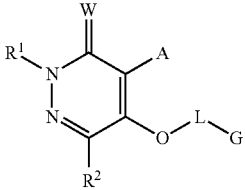

W is O

| Cmpd. No. | R$^1$ | R$^2$ | L | G | A | M.P (° C.) |
|---|---|---|---|---|---|---|
| 1 (Ex. 1) | Me | Cl | direct bond | H | 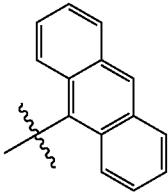 [SMILES: *c1c2ccccc2cc2ccccc12] | 236-238 * |
| 2 (Ex. 2) | Me | Cl | direct bond | H | 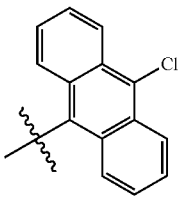 [SMILES: *c1c2ccccc2c(Cl)c2ccccc12] | * |
| 3 | Me | Cl | direct bond | H | 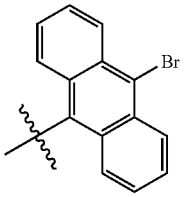 [SMILES: *c1c2ccccc2c(Br)c2ccccc12] | * |
| 4 | Me | Cl | direct bond | CH$_3$ | 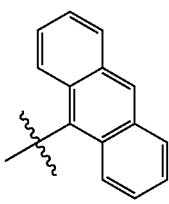 [SMILES: *c1c2ccccc2cc2ccccc12] | * |
| 5 | Me | Cl | direct bond | H | 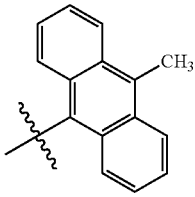 [SMILES: *c1c2ccccc2c(C)c2ccccc12] | * |

INDEX TABLE A-continued

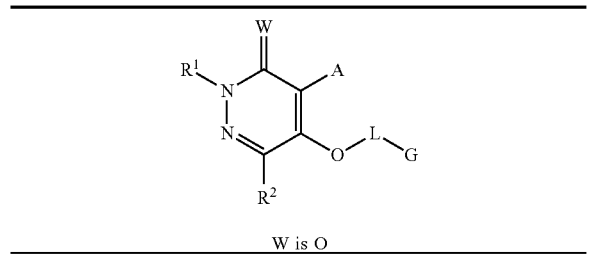

W is O

| Cmpd. No. | R¹ | R² | L | G | A | M.P (° C.) |
|---|---|---|---|---|---|---|
| 6 | Me | Cl | direct bond | C(=O)CH₃ | 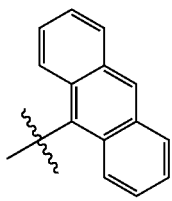 | * |
| 7 | Me | Cl | direct bond | H (morpholine salt) | 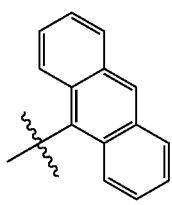 | * |
| 8 | Me | Me | direct bond | H | 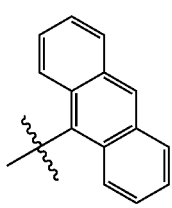 | * |

INDEX TABLE A-continued

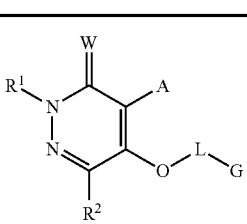

W is O

| Cmpd. No. | R¹ | R² | L | G | A | M.P (° C.) |
|---|---|---|---|---|---|---|
| 9 | Me | Me | direct bond | H | 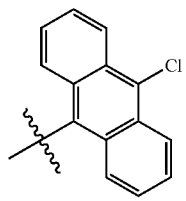 [SMILES: *c1c2ccccc2c(Cl)c2ccccc12] | * |
| 10 | Me | Me | direct bond | H | 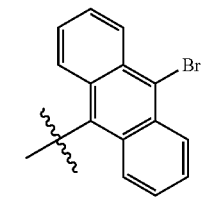 [SMILES: *c1c2ccccc2c(Br)c2ccccc12] | * |

\* See Index Table B for ¹H NMR or M.S. data.

INDEX TABLE B

Cmpd. No.   ¹H NMR Data (DMSO-d₆ solution unless indicated otherwise)[a] and M.S. data

| | |
|---|---|
| 1 | δ 8.70 (s, 1H), 8.15 (d, 2H), 7.68 (d, 2H), 7.52 (t, 2H), 7.45 (t, 2H), 5.75 (s, 1H), 3.67 (s, 3H). |
| 2 | δ 8.52 (d, 2H), 7.61 (d, 2H), 7.74 (distorted t, 2H), 7.56 (distorted t, 2H), 3.67 (s, 3H). |
| 3 | δ 8.53 (d, 2H), 7.80 (d, 2H), 7.74-7.71 (m, 2H), 7.56-7.53 (m, 2H), 3.67 (s, 3H). |
| 4 | (CDCl₃) δ 8.57 (s, 1H), 8.08-8.04 (m, 2H), 7.68-7.64 (m, 2H), 7.51-7.46 (m, 4H), 3.82 (s, 3H), 3.05 (s, 3H). |
| 5 | δ 11.05 (br s, 1H), 8.44 (d, 2H), 7.70 (d, 2H), 7.58 (t, 2H), 7.47 (t, 2H), 3.68 (s, 3H), 3.16 (s, 3H). |
| 6 | (CDCl₃) δ 8.55 (s, 1H), 8.03 (distorted d, 2H), 7.60 (distorted d, 2H), 7.49-7.42 (m, 4H), 3.91 (s, 3H), 1.68 (s, 3H). |
| 7 | 335 (M − 1). |
| 8 | δ 10.12 (s, 1H), 8.69 (s, 1H), 8.13 (d, 2H), 7.60 (d, 2H), 7.51 (t, 2H), 7.42 (t, 2H), 3.65 (s, 3H), 2.33 (s, 3H). |
| 9 | δ 10.23 (s, 1H), 8.52 (d, 2H), 7.74-7.70 (m, 4H), 7.57-7.52 (m, 2H), 3.65 (s, 3H), 2.32 (s, 3H). |
| 10 | δ 10.25 (s, 1H), 8.53 (d, 2H), 7.76-7.69 (m, 4H), 7.54 (dd, 2H), 3.65 (s, 3H), 2.32 (s, 3H). |

[a]¹H NMR data are in ppm downfield from tetramethylsilane.

Couplings are designated by (s)—singlet, (d)—doublet, (t)—triplet, (m)—multiplet.

BIOLOGICAL EXAMPLES OF THE INVENTION

Test A

Seeds of plant species selected from barnyardgrass (*Echinochloa crus-galli*), kochia (*Kochia scoparia*), ragweed (common ragweed, *Ambrosia elation*), ryegrass, Italian (Italian ryegrass, *Lolium multiflorum*), foxtail, green (green foxtail, *Setaria viridis*), and pigweed (*Amaranthus retroflexus*) were planted into a blend of loam soil and sand and treated preemergence with a directed soil spray using test chemicals formulated in a non-phytotoxic solvent mixture which included a surfactant.

At the same time, plants selected from these weed species and also wheat (*Triticum aestivum*), corn (*Zea mays*), blackgrass (*Alopecurus myosuroides*), and galium (catchweed bedstraw, *Galium aparine*) were planted in pots containing the same blend of loam soil and sand and treated with postemergence applications of test chemicals formulated in the same manner Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (—) response means no test result.

TABLE A

| Compounds | | | | | | | |
|---|---|---|---|---|---|---|---|
| 125 g ai/ha Postemergence | 1 | 2 | 3 | 5 | 6 | 7 | 8 |
| Barnyardgrass | 20 | 20 | 60 | 30 | 10 | 0 | 50 |
| Blackgrass | 10 | 60 | 70 | 0 | 0 | 10 | 30 |
| Corn | 0 | 0 | 10 | 20 | 0 | 10 | 10 |
| Foxtail, Giant | — | — | — | — | 20 | 10 | 60 |
| Foxtail, Green | 50 | 60 | 90 | 30 | — | — | — |
| Galium | 90 | 100 | 90 | 70 | 100 | 100 | 90 |
| Kochia | 20 | 70 | 50 | 0 | 20 | 10 | 10 |
| Pigweed | 100 | 100 | 100 | 90 | 100 | 100 | 100 |
| Ragweed | 90 | 90 | 90 | 20 | 90 | 100 | 90 |
| Ryegrass, Italian | 40 | 80 | 50 | 50 | 70 | 60 | 100 |
| Wheat | 10 | 30 | 60 | 0 | 10 | 0 | 0 |
| Compounds | | | | | | | |
| 31 g ai/ha Postemergence | 1 | 2 | 3 | 5 | 6 | 7 | 8 |
| Barnyardgrass | 0 | 0 | 20 | 0 | 0 | 0 | 10 |
| Blackgrass | 0 | 0 | 10 | 0 | 0 | 0 | 0 |
| Corn | 0 | 0 | 0 | 10 | 0 | 10 | 10 |
| Foxtail, Giant | — | — | — | — | 0 | 0 | 10 |
| Foxtail, Green | 10 | 10 | 40 | 0 | — | — | — |
| Galium | 70 | 20 | 90 | 20 | 80 | 70 | 80 |
| Kochia | 10 | 10 | 10 | 0 | 0 | 0 | 0 |
| Pigweed | 90 | 100 | 100 | 50 | 100 | 100 | 90 |
| Ragweed | 80 | 90 | 80 | 10 | 90 | 90 | 90 |
| Ryegrass, Italian | 20 | 50 | 40 | 0 | 20 | 10 | 90 |
| Wheat | 0 | 0 | 20 | 0 | 10 | 0 | 0 |
| Compounds | | | | | | | |
| 125 g ai/ha Preemergence | 1 | 2 | 3 | 5 | 6 | 7 | 8 |
| Barnyardgrass | 0 | 0 | 50 | 0 | 0 | 0 | 10 |
| Foxtail, Giant | — | — | — | — | 10 | 0 | 10 |
| Foxtail, Green | 0 | 90 | 80 | 0 | — | — | — |
| Kochia | 20 | 10 | 50 | 0 | 0 | 0 | 0 |
| Pigweed | 100 | 100 | 100 | 60 | 100 | 100 | 100 |
| Ragweed | 100 | 100 | 100 | 0 | 100 | 40 | 90 |
| Ryegrass, Italian | 30 | 70 | 80 | 0 | 30 | 0 | 50 |
| Compounds | | | | | | | |
| 31 g ai/ha Preemergence | 1 | 2 | 3 | 5 | 6 | 7 | 8 |
| Barnyardgrass | 0 | 0 | 0 | 0 | 0 | 0 | 0 |
| Foxtail, Giant | — | — | — | — | 0 | 0 | 0 |
| Foxtail, Green | 0 | 0 | 10 | 0 | — | — | — |
| Kochia | 0 | 0 | 0 | 0 | 0 | 0 | 0 |
| Pigweed | 100 | 100 | 100 | 0 | 80 | 60 | 100 |
| Ragweed | 70 | 80 | 20 | 0 | 40 | 0 | 40 |
| Ryegrass, Italian | 20 | 20 | 20 | 0 | 30 | 0 | 10 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At the time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (—) response means no test result.

TABLE B

| Compounds | | | | | | |
|---|---|---|---|---|---|---|
| 250 g ai/ha Flood | 1 | 2 | 5 | 6 | 7 | 8 |
| Barnyardgrass | 20 | 0 | 0 | 0 | 0 | 15 |
| Ducksalad | 85 | 80 | 90 | 85 | 100 | 90 |
| Rice | 0 | 0 | 0 | 0 | 0 | 15 |
| Sedge, Umbrella | 90 | 75 | 95 | 95 | 100 | 90 |

What is claimed is:

1. A compound of Formula 1, stereoisomers, N-oxides, and salts thereof

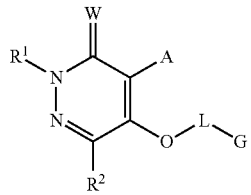

wherein
W is O or S;
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl; or a 5- or 6-membered saturated or partially saturated heterocyclic ring containing ring members selected from carbon and up to 1 O and 1 S;

$R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl; or phenyl optionally substituted by halogen, $C_1$-$C_4$ alkyl or $C_1$-$C_4$ haloalkyl;

L is a direct bond, $C_1$-$C_4$ alkanediyl or $C_2$-$C_4$ alkenediyl;

G is H, C(=O)$R^5$, C(=S)$R^5$, CO$_2$$R^6$, C(=O)SR$^6$, S(O)$_2$$R^5$, CONR$^7$$R^8$, S(O)$_2$NR$^7$$R^8$ or P(=O)$R^9$$R^{10}$; or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_3$-$C_6$ cycloalkyl or $C_4$-$C_7$ cycloalkylalkyl; or a 5- or 6-membered heterocyclic ring;

A is selected from

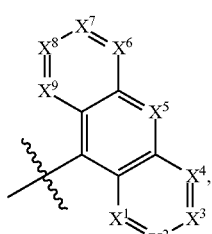
A-1

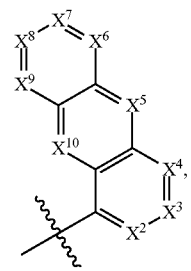
A-2

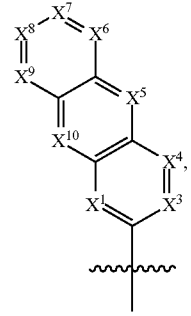
A-3

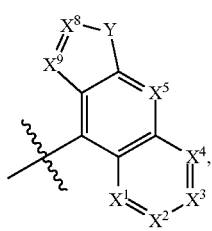
A-4

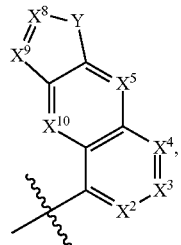
A-5

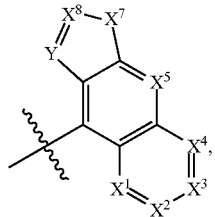
A-6

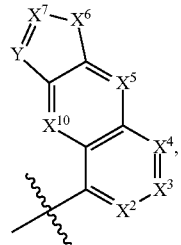
A-7

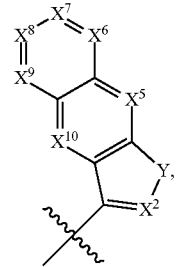
A-8

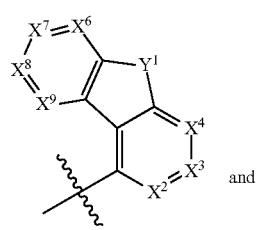
A-9 and

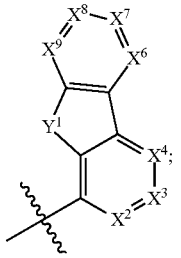
A-10

$X^1$, $X^2$, $X^3$, $X^4$, $X^5$, $X^6$, $X^7$, $X^8$, $X^9$ and $X^{10}$ are each independently N or CR$^3$; provided that no more than 4 of $X^1$, $X^2$, $X^3$, $X^4$, $X^5$, $X^6$, $X^7$, $X^8$, $X^9$ and $X^{10}$ are N;

Y is O, S or NR$^4$;

Y$^1$ is O, S, NR$^4$ or CR$^{3a}$R$^{3b}$;

each R$^3$ is independently H, halogen, cyano, nitro, C$_1$-C$_5$ alkyl, C$_2$-C$_5$ alkenyl, C$_2$-C$_5$ alkynyl, C$_3$-C$_5$ cycloalkyl, C$_4$-C$_5$ cycloalkylalkyl, C$_1$-C$_5$ haloalkyl, C$_3$-C$_5$ haloalkenyl, C$_3$-C$_5$ haloalkynyl, C$_2$-C$_5$ alkoxyalkyl, C$_1$-C$_5$ alkoxy, C$_1$-C$_5$ haloalkoxy, C$_1$-C$_5$ alkylthio, C$_1$-C$_4$ alkylsulfinyl, C$_1$-C$_4$ alkylsulfonyl, C$_1$-C$_5$ haloalkylthio or C$_2$-C$_5$ alkoxycarbonyl;

R$^{3a}$ is H, halogen, —CN, nitro, C$_1$-C$_5$ alkyl, C$_2$-C$_5$ alkenyl, C$_2$-C$_5$ alkynyl, C$_3$-C$_5$ cycloalkyl, C$_4$-C$_5$ cycloalkylalkyl, C$_1$-C$_5$ haloalkyl, C$_3$-C$_5$ haloalkenyl, C$_3$-C$_5$ haloalkynyl, C$_2$-C$_5$ alkoxyalkyl, C$_1$-C$_5$ alkoxy, C$_1$-C$_5$ haloalkoxy, C$_1$-C$_5$ alkylthio, C$_1$-C$_4$ alkylsulfinyl, C$_1$-C$_4$ alkylsulfonyl, C$_1$-C$_5$ haloalkylthio or C$_2$-C$_5$ alkoxycarbonyl;

R$^{3b}$ is H, halogen, —CN, nitro, C$_1$-C$_5$ alkyl, C$_2$-C$_5$ alkenyl, C$_2$-C$_5$ alkynyl, C$_3$-C$_5$ cycloalkyl, C$_4$-C$_5$ cycloalkylalkyl, C$_1$-C$_5$ haloalkyl, C$_3$-C$_5$ haloalkenyl, C$_3$-C$_5$ haloalkynyl, C$_2$-C$_5$ alkoxyalkyl, C$_1$-C$_5$ alkoxy, C$_1$-C$_5$ haloalkoxy, C$_1$-C$_5$ alkylthio, C$_1$-C$_4$ alkylsulfinyl, C$_1$-C$_4$ alkylsulfonyl, C$_1$-C$_5$ haloalkylthio or C$_2$-C$_5$ alkoxycarbonyl; or R$^{3a}$ and R$^{3b}$ are taken together as =O; or R$^{3a}$ and R$^{3b}$ are taken together with the carbon atom to which they are bonded to form an optionally substituted 3- to 7-membered carbocyclic ring;

R$^4$ is H, C$_1$-C$_3$ alkyl or C$_1$-C$_3$ haloalkyl;

R$^5$ and R$^7$ are independently H, C$_1$-C$_7$ alkyl, C$_3$-C$_7$ alkenyl, C$_3$-C$_7$ alkynyl, C$_3$-C$_7$ cycloalkyl, C$_1$-C$_7$ haloalkyl, C$_3$-C$_7$ haloalkenyl, C$_2$-C$_7$ alkoxyalkyl or C$_4$-C$_7$ cycloalkylalkyl; or phenyl, benzyl, or a 5- to 6-membered heterocyclic ring, each phenyl, benzyl or heterocyclic ring optionally substituted by halogen, C$_1$-C$_4$ alkyl or C$_1$-C$_4$ haloalkyl;

R$^6$ is C$_1$-C$_7$ alkyl, C$_3$-C$_7$ alkenyl, C$_3$-C$_7$ alkynyl, C$_3$-C$_7$ cycloalkyl, C$_2$-C$_7$ haloalkyl, C$_3$-C$_7$ haloalkenyl, C$_2$-C$_7$ alkoxyalkyl or C$_4$-C$_7$ cycloalkylalkyl; or phenyl, benzyl or a 5- to 6-membered heterocyclic ring, each phenyl, benzyl or heterocyclic ring optionally substituted by halogen, C$_1$-C$_4$ alkyl or C$_1$-C$_4$ haloalkyl;

R$^8$ is H, C$_1$-C$_7$ alkyl, C$_2$-C$_7$ alkenyl, C$_2$-C$_7$ alkynyl, C$_3$-C$_7$ cycloalkyl, C$_4$-C$_7$ cycloalkylalkyl, C$_1$-C$_7$ haloalkyl or C$_2$-C$_7$ alkoxyalkyl;

R$^9$ is C$_1$-C$_7$ alkyl or C$_1$-C$_7$ alkoxy; and

R$^{10}$ is C$_1$-C$_7$ alkyl or C$_1$-C$_7$ alkoxy.

2. The compound of claim 1 wherein

R$^1$ is H, C$_1$-C$_7$ alkyl, C$_3$-C$_8$ alkylcarbonylalkyl, C$_3$-C$_8$ alkoxycarbonylalkyl, C$_4$-C$_7$ alkylcycloalkyl, C$_3$-C$_7$ alkenyl, C$_3$-C$_7$ alkynyl, C$_3$-C$_7$ cycloalkyl, C$_4$-C$_7$ cycloalkylalkyl, C$_2$-C$_3$ cyanoalkyl, C$_1$-C$_4$ nitroalkyl, C$_2$-C$_7$ haloalkoxyalkyl, C$_1$-C$_7$ haloalkyl, C$_3$-C$_7$ haloalkenyl, C$_2$-C$_7$ alkoxyalkyl, C$_3$-C$_7$ alkylthioalkyl, C$_1$-C$_7$ alkoxy, benzyl or phenyl;

W is O;

A is selected from A-1, A-4 and A-6;

L is a direct bond;

G is H, C(=O)R$^5$, C(=S)R$^5$, CO$_2$R$^6$, C(=O)SR$^6$, CONR$^7$R$^8$ or P(=O)R$^9$R$^{10}$; or C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_2$-C$_4$ alkoxyalkyl, C$_3$-C$_6$ cycloalkyl or C$_4$-C$_7$ cycloalkylalkyl;

R$^2$ is H, halogen, cyano, formyl, C$_1$-C$_7$ alkyl, C$_3$-C$_8$ alkylcarbonylalkyl, C$_3$-C$_8$ alkoxycarbonylalkyl, C$_2$-C$_7$ alkylcarbonyloxy, C$_4$-C$_7$ alkylcycloalkyl, C$_3$-C$_7$ alkenyl, C$_3$-C$_7$ alkynyl, C$_1$-C$_4$ alkylsulfinyl, C$_1$-C$_4$ alkylsulfonyl, C$_1$-C$_4$ alkylamino, C$_2$-C$_8$ dialkylamino, C$_3$-C$_7$ cycloalkyl, C$_4$-C$_7$ cycloalkylalkyl, C$_2$-C$_3$ cyanoalkyl, C$_1$-C$_4$ nitroalkyl, C$_2$-C$_7$ haloalkoxyalkyl, C$_1$-C$_7$ haloalkyl, C$_3$-C$_7$ haloalkenyl, C$_2$-C$_7$ alkoxyalkyl, C$_1$-C$_7$ alkoxy or C$_1$-C$_5$ alkylthio; and each R$^3$ is independently H, halogen, C$_1$-C$_3$ alkyl, C$_3$-C$_4$ cycloalkyl, C$_1$-C$_3$ haloalkyl or C$_1$-C$_3$ alkoxy.

3. The compound of claim 2 wherein

R$^1$ is H, C$_1$-C$_7$ alkyl, C$_3$-C$_8$ alkoxycarbonylalkyl, C$_4$-C$_7$ alkylcycloalkyl, C$_3$-C$_7$ cycloalkyl, C$_4$-C$_7$ cycloalkylalkyl, C$_2$-C$_3$ cyanoalkyl, C$_1$-C$_4$ nitroalkyl, C$_2$-C$_7$ haloalkoxyalkyl, C$_1$-C$_7$ haloalkyl, C$_2$-C$_7$ alkoxyalkyl, C$_3$-C$_7$ alkylthioalkyl, C$_1$-C$_7$ alkoxy or benzyl;

A is A-1;

G is H, C(=O)R$^5$, CO$_2$R$^6$, CONR$^7$R$^8$ or P(=O)R$^9$R$^{10}$; or C$_1$-C$_4$ alkyl, C$_2$-C$_4$ alkenyl, C$_1$-C$_4$ haloalkyl, C$_2$-C$_4$ haloalkenyl, C$_2$-C$_4$ alkoxyalkyl, C$_3$-C$_6$ cycloalkyl or C$_4$-C$_7$ cycloalkylalkyl;

R$^2$ is H, halogen, cyano, formyl, C$_1$-C$_7$ alkyl, C$_2$-C$_4$ alkylcarbonyl, C$_2$-C$_7$ alkylcarbonyloxy, C$_4$-C$_7$ alkylcycloalkyl, C$_1$-C$_4$ alkylsulfinyl, C$_1$-C$_4$ alkylsulfonyl, C$_1$-C$_4$ alkylamino, C$_3$-C$_7$ cycloalkyl, C$_4$-C$_7$ cycloalkylalkyl, C$_2$-C$_3$ cyanoalkyl, C$_1$-C$_4$ nitroalkyl, C$_2$-C$_7$ haloalkoxyalkyl, C$_1$-C$_7$ haloalkyl, C$_2$-C$_7$ alkoxyalkyl or C$_1$-C$_7$ alkoxy; and each R$^3$ is independently H, halogen, C$_1$-C$_2$ alkyl, cyclopropyl or C$_1$-C$_2$ haloalkyl.

4. The compound of claim 3 wherein

R$^1$ is C$_1$-C$_4$ alkyl, C$_3$-C$_4$ cycloalkyl, C$_2$-C$_3$ cyanoalkyl, C$_1$-C$_3$ haloalkyl or C$_2$-C$_4$ alkoxyalkyl;

G is H, C(=O)R$^5$, CO$_2$R$^6$ or P(=O)R$^9$R$^{10}$; or C$_1$-C$_4$ alkyl, C$_1$-C$_4$ haloalkyl, C$_2$-C$_4$ alkoxyalkyl or C$_3$-C$_6$ cycloalkyl;

R$^2$ is H, halogen, cyano, C$_1$-C$_4$ alkyl, C$_3$-C$_5$ cycloalkyl, C$_1$-C$_3$ haloalkyl, C$_2$-C$_4$ alkoxyalkyl or C$_1$-C$_3$ alkoxy; and each R$^3$ is independently H, halogen, methyl, ethyl or CF$_3$.

5. The compound of claim 4 wherein

R$^1$ is methyl, ethyl, n-propyl or 2-methoxyethyl;

G is H, C(=O)R$^5$ or CO$_2$R$^6$; or C$_2$-C$_4$ alkoxyalkyl or C$_3$-C$_6$ cycloalkyl;

R$^2$ is H, Cl, Br, I, —CN, methyl or methoxy; and each R$^3$ is independently H, F, Cl, Br or methyl.

6. The compound of claim 1 selected from the group consisting of 4-(9-anthracenyl)-6-chloro-5-hydroxy-2-methyl-3(2H)-pyridazinone;

6-chloro-4-(10-chloro-9-anthracenyl)-5-hydroxy-2-methyl-3(2H)-pyridazinone; and 4-(10-bromo-9-anthracenyl)-6-chloro-5-hydroxy-2-methyl-3(2H)-pyridazinone.

7. A herbicidal composition comprising a compound of claim 1 and at least one component selected from the group consisting of surfactants, solid diluents and liquid diluents.

8. A herbicidal composition comprising a compound of claim 1, at least one additional active ingredient selected from the group consisting of other herbicides and herbicide safeners, and at least one component selected from the group consisting of surfactants, solid diluents and liquid diluents.

9. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solanesyl transferase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

10. A method for controlling the growth of undesired vegetation comprising contacting the vegetation or its environment with a herbicidally effective amount of a compound of claim 1.

* * * * *